US011584921B2

(12) United States Patent
Mandell et al.

(10) Patent No.: US 11,584,921 B2
(45) Date of Patent: Feb. 21, 2023

(54) NON-STANDARD AMINO ACID CONTAINING COMPOSITIONS AND USES THEREOF

(71) Applicant: GRO Biosciences Inc., Cambridge, MA (US)

(72) Inventors: Daniel J. Mandell, Brookline, MA (US); Christopher J. Gregg, Melrose, MA (US); Peter B. Stranges, Arlington, MA (US)

(73) Assignee: GRO Biosciences Inc., Cambridge, MA (US)

( * ) Notice: Subject to any disclaimer, the term of this patent is extended or adjusted under 35 U.S.C. 154(b) by 0 days.

(21) Appl. No.: 17/144,946

(22) Filed: Jan. 8, 2021

(65) Prior Publication Data

US 2021/0371838 A1    Dec. 2, 2021

Related U.S. Application Data

(63) Continuation of application No. PCT/US2019/041006, filed on Jul. 9, 2019.

(60) Provisional application No. 62/695,505, filed on Jul. 9, 2018.

(51) Int. Cl.
*C12N 9/22* (2006.01)

(52) U.S. Cl.
CPC ........ *C12N 9/22* (2013.01); *C12Y 301/21001* (2013.01)

(58) Field of Classification Search
CPC ... C12N 9/22; C12N 15/10; C12Y 301/21001
See application file for complete search history.

(56) References Cited

U.S. PATENT DOCUMENTS

| | | | |
|---|---|---|---|
| 6,277,614 B1 | 8/2001 | Komori et al. | |
| 2009/0047272 A1* | 2/2009 | Appelbaum | A61P 37/00 424/94.61 |
| 2012/0225467 A1 | 9/2012 | Ramaswamy et al. | |
| 2017/0209376 A1 | 7/2017 | Applebaum | |
| 2018/0105854 A1 | 4/2018 | Soll et al. | |
| 2018/0112201 A1 | 4/2018 | Chen Zeltsburg et al. | |
| 2018/0125937 A1 | 5/2018 | De Fougerolles et al. | |

FOREIGN PATENT DOCUMENTS

| | | |
|---|---|---|
| WO | WO-2018011276 A1 | 1/2018 |
| WO | WO-2018045018 A1 | 3/2018 |
| WO | WO-2020014226 A1 | 1/2020 |
| WO | WO-2020106709 A1 | 5/2020 |

OTHER PUBLICATIONS

Witkowski et al., Biochemistry 38:11643-11650, 1999.*
Tang et al., Phil Trans R Soc B 368:20120318, 1-10, 2013.*
Seffemick et al., J. Bacteriol. 183(8):2405-2410, 2001.*
Branden et al., Introduction to Protein Structure, Garland Publishing Inc., New York, p. 247, 1991.*
Sadowski et al., Current Opinion in Structural Biology 19:357-362, 2009.*
International Search Report and Written Opinion for corresponding PCT Application No. PCT/US2019/041006 dated Nov. 8, 2019.
Batzer, M. et al., "Enhanced evolutionary PCR using oligonucleotides with inosine at the 3'-terminus", Nucleic Acids Research, 1991, vol. 19, No. 18, p. 5081.
Database Geneseq [online] May 3, 2018, "Selenocysteine modified protein, SEQ1204", retrieved from EBI accession No. GS_PROT: BFD28961.
European Patent Application No. 19833109.2 Extended European Search Report dated Jun. 20, 2022.
International Preliminary Report on Patentability for corresponding PCT Application No. PCT/US2019/041006 dated Jan. 12, 2021.
Ohtsuka, E. et al., "An Alternative Approach to Deoxyoligonucleotides as Hybridization Probes by Insertion of Deoxyinosine at Ambiguous Codon Positions", The Journal of Biological Chemistry, 1985, vol. 260, No. 5, pp. 2605-2608.
Rossolini, G. M. et al., "Use of deoxyinosine-containing primers vs degenerate primers for polymerase chain reaction based on ambiguous sequence information", Molecular and Cellular Probes, 1994, vol. 8, pp. 91-98.
Thyer, R. et al., "Custom selenoprotein production enabled by laboratory evolution of recoded bacterial strains", Nature Biotechnology, 2018, vol. 36, No. 7, pp. 624-631.
Thyer, R. et al., "Supplementary Figures: Custom selenoprotein production enabled by laboratory evolution of recoded bacterial strains", Nature Biotechnology, 2018, vol. 36, No. 7, pp. 624-631.

* cited by examiner

*Primary Examiner* — Delia M Ramirez
(74) *Attorney, Agent, or Firm* — Wilson Sonsini Goodrich & Rosati

(57) ABSTRACT

Provided herein is a stabilized DNase I polypeptide containing a non-standard amino acid that maintains enzymatic activity even under harsh conditions, such as reducing environments. The stabilized DNase I polypeptide has enzymatic activity in reducing environments that is higher than a corresponding DNase I polypeptide without the non-standard amino acids under the same conditions. Also provided herein are polynucleotides encoding the stabilized DNase I polypeptide, cells for expressing and/or producing the stabilized DNase I polypeptide, and methods of use of the stabilized DNase I polypeptide.

18 Claims, 1 Drawing Sheet
Specification includes a Sequence Listing.

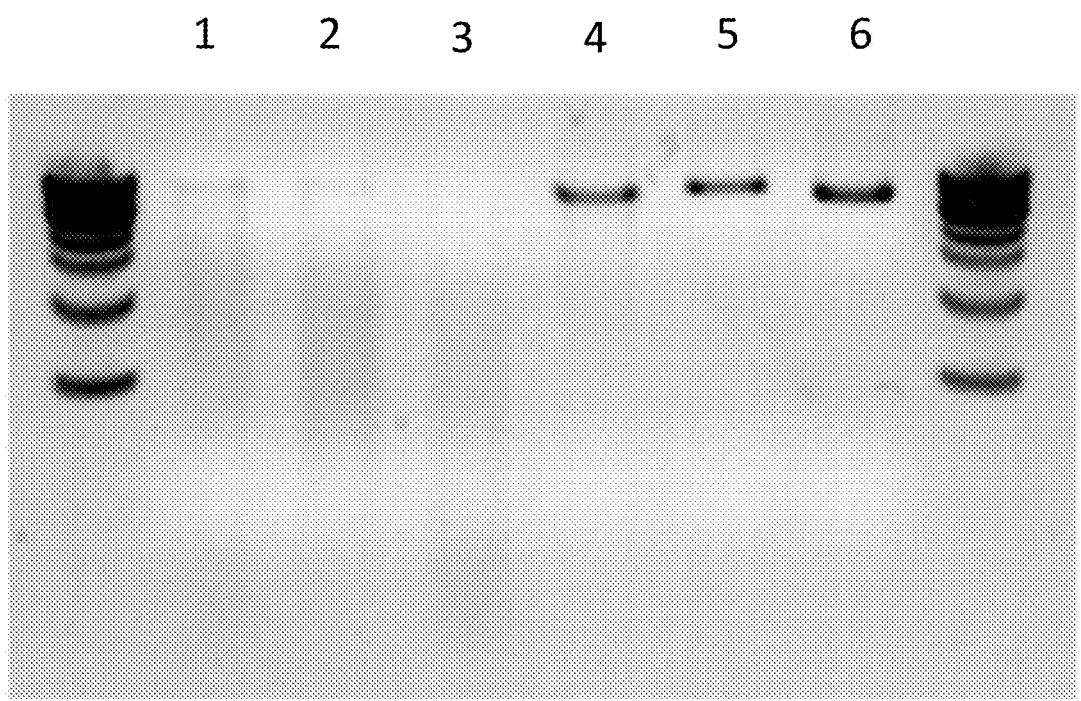
1 – seleno-DNase I (-DTT)
2 – disulfide-DNase I (-DTT)
3 – seleno-DNase I (+DTT)
4 – disulfide-DNase I (+DTT)
5 – Input DNA (-DTT)
6 – Input DNA (+DTT)

NON-STANDARD AMINO ACID CONTAINING COMPOSITIONS AND USES THEREOF

CROSS-REFERENCE

This application is a continuation of International Application No. PCT/US2019/041006, filed Jul. 9, 2019, which claims the benefit of U.S. Provisional Patent Application No. 62/695,505, filed Jul. 9, 2018, each of which is entirely incorporated herein by reference.

BACKGROUND

The activity of many enzymes depends on the environment in which they catalyze their respective reactions, for example, buffers with reducing conditions. Often, enzymes rely on certain structural features to maintain their activity and these structural features may be compromised by certain conditions. For example, under reducing conditions, the intermolecular and/or intramolecular disulfide bridges of enzymes may be reduced, leading to structural changes in the enzyme and ultimately, reduction or loss of activity. For example, many methods for single cell sequencing and single cell PCR require use of harsh lysis buffers to lyse cells within a droplet to extract or amplify polynucleotides (such as mRNA) or to extract proteins from the single cell. Following lysis, reactions including reverse transcription reactions, polymerase catalyzed reactions such as copying and/or synthesizing polynucleotides, ligation reactions, amplification reactions, nuclease catalyzed reactions, and protease mediated reactions are often employed. However, catalysis of these reactions is often reduced or not possible due to the harsh nature of the lysis buffer in which the enzymes catalyzing these reactions are present.

SUMMARY OF THE INVENTION

Provided herein are compositions and methods that overcome these problems. Provided herein are stabilized enzymes that maintain activity even in harsh conditions such as reducing environments. Provided herein are stabilized enzymes containing non-standard amino acids that have enzymatic activity in harsh conditions, such as reducing buffers, that is higher than a corresponding enzyme without the non-standard amino acids under the same conditions. Also provided herein are polynucleotides encoding these stabilized enzymes, cells for expressing and/or producing these stabilized enzymes, and methods of use of these stabilized enzymes. In some aspects, the stabilized enzymes comprise a stabilized deoxyribonuclease I (DNase I) polypeptide.

In some aspects, provided herein is a composition comprising a stabilized deoxyribonuclease I (DNase I) polypeptide comprising one or more non-standard amino acids, a functional fragment thereof, or a variant thereof.

In some aspects, provided herein is a composition comprising a stabilized deoxyribonuclease I (DNase I) polypeptide comprising one or more non-standard amino acids, a functional fragment thereof, or a variant thereof, wherein the stabilized DNase I polypeptide has a higher endonuclease activity for a DNA substrate in an environment than an endonuclease activity for the DNA substrate of a corresponding DNase I polypeptide, functional fragment thereof, or variant thereof that does not comprise the one or more non-standard amino acids.

In some aspects, provided herein is a composition comprising a stabilized deoxyribonuclease I (DNase I) polypeptide comprising one or more non-standard amino acids, a functional fragment thereof, or a variant thereof, wherein the stabilized DNase I polypeptide does not destabilize in an environment that a corresponding DNase I polypeptide, functional fragment thereof, or variant thereof that does not comprise the one or more non-standard amino acids does destabilize.

In some aspects, provided herein is a composition comprising a stabilized deoxyribonuclease I (DNase I) polypeptide comprising one or more non-standard amino acids, a functional fragment thereof, or a variant thereof, wherein the stabilized DNase I polypeptide has a melting temperature (Tm) that is at least 5° C. higher than a Tm of a corresponding DNase I polypeptide, functional fragment thereof, or variant thereof that does not comprise the one or more non-standard amino acids.

In some embodiments, the stabilized DNase I polypeptide, functional fragment thereof, or variant thereof, has a melting temperature (Tm) that is at least 5° C. higher than a Tm of a corresponding recombinant enzyme, functional fragment thereof, or variant thereof that does not comprise the one or more non-standard amino acids.

In some embodiments, the stabilized DNase I polypeptide, functional fragment thereof, or variant thereof, has a higher endonuclease activity for a DNA substrate in an environment than an endonuclease activity for the DNA substrate of a corresponding DNase I polypeptide, functional fragment thereof, or variant thereof that does not comprise the one or more non-standard amino acids.

In some embodiments, the stabilized DNase I polypeptide, functional fragment thereof, or variant thereof, does not destabilize in an environment that a corresponding DNase I polypeptide, functional fragment thereof, or variant thereof that does not comprise the one or more non-standard amino acids does destabilize.

In some embodiments, at least one, two, three, four or more of the one or more non-standard amino acids is selenocysteine.

In some embodiments, at least two of the one or more non-standard amino acids are directly linked by a bond.

In some embodiments, at least four of the one or more non-standard amino acids are directly linked by a bond, wherein a first pair of the at least four of the one or more non-standard amino acids is directly linked by a bond, and a second pair of at the least four of the one or more non-standard amino acids is directly linked by a bond.

In some embodiments, the bond is a diselenide bond.

In some embodiments, the diselenide bond is an intermolecular or an intramolecular bond.

In some embodiments, the stabilized DNase I polypeptide, functional fragment thereof, or variant thereof, has a half-life that is at least 1.1 fold higher than a half-life of a corresponding DNase I polypeptide, functional fragment thereof, or variant thereof that does not comprise the one or more non-standard amino acid.

In some embodiments, the stabilized DNase I polypeptide, functional fragment thereof, or variant thereof, has at least 70%, 75%, 80%, 85%, 90%, 95% sequence identity to SEQ ID NO:1.

In some embodiments, the stabilized DNase I polypeptide, functional fragment thereof, or variant thereof, comprises a sequence with at least 70%, 75%, 80%, 85%, 90%, 95% sequence identity to at least 25, 50, 75, 100, 125, 150, 175, 200, 225, 250, or 261 contiguous amino acids of SEQ ID NO: 1.

In some embodiments, the one or more non-standard amino acids is at position 102 of SEQ ID NO:1, position 105 of SEQ ID NO:1, position 174 of SEQ ID NO:1, or position 210 of SEQ ID NO:1.

In some embodiments, a non-standard amino acid at position 102 is directly linked by a bond to a non-standard amino acid at position 105.

In some embodiments, a non-standard amino acid at position 174 is directly linked by a bond to a non-standard amino acid at position 210.

In some embodiments, the bond is a diselenide bond.

In some embodiments, the diselenide bond is in a location of a disulfide bond in a corresponding recombinant enzyme without the one or more non-standard amino acids.

In some embodiments, the $T_m$ of the corresponding stabilized DNase I polypeptide, functional fragment thereof, or variant thereof, is less than 37° C.

In some embodiments, the $T_m$ of the stabilized DNase I polypeptide, functional fragment thereof, or variant thereof, is greater than 37° C., 40° C., 45° C., 50° C., 55° C., 60° C., or 65° C.

In some embodiments, the $T_m$ of the stabilized DNase I polypeptide, functional fragment thereof, or variant thereof, is at least 10° C. higher than the $T_m$ of the corresponding recombinant enzyme, functional fragment thereof, or variant thereof.

In some embodiments, the $T_m$ of the stabilized DNase I polypeptide, functional fragment thereof, or variant thereof, is at least 15° C. higher than the $T_m$ of the corresponding recombinant enzyme, functional fragment thereof, or variant thereof.

In some embodiments, the stabilized DNase I polypeptide, functional fragment thereof, or variant thereof, has a half-life in an environment that is at least 1.1 fold higher than a half-life of a corresponding DNase I polypeptide, functional fragment thereof, or variant thereof that does not comprise the one or more non-standard amino acids in the environment.

In some embodiments, the half-life of the DNase I polypeptide, functional fragment thereof, or variant thereof in the environment, is greater than 1, 2, 3, 4, 5, 6, 7, 8, 9, 10, 11, 12, 13, 14, 15, 16, 17, 18, 19, 20, 21, 22, 23, 24 or more hours.

In some embodiments, the half-life of the DNase I polypeptide, functional fragment thereof, or variant thereof in the environment, is greater than 1, 2, 3, 4, 5, 6, 7, 8, 9, 10, 11, 12, 13, 14, 15, 16, 17, 18, 19, 20, 21, 22, 23, 24 or more days.

In some embodiments, the stabilized DNase I polypeptide has at least a 1.1, 1.2, 1.3, 1.4, 1.5, 1.6, 1.7, 1.8, 1.9, 2, 3, 4, 5, 6, 7, 8, 10, 20, 30, 40, 50, 60, 70, 80, 90 or 100 fold higher endonuclease activity for a DNA substrate in an environment than an endonuclease activity for the DNA substrate of a corresponding DNase I polypeptide, functional fragment thereof, or variant thereof that does not comprise the one or more non-standard amino acids.

In some embodiments, the stabilized DNase I polypeptide has at least a 1.1, 1.2, 1.3, 1.4, 1.5, 1.6, 1.7, 1.8, 1.9, 2, 3, 4, 5, 6, 7, 8, 10, 20, 30, 40, 50, 60, 70, 80, 90 or 100 fold higher endonuclease activity for a DNA substrate after being present in an environment for at least 1, 2, 3, 4, 5, 6, 7, 8, 9, 10, 15, 20, 25, 30, 40, or 50 minutes than an endonuclease activity for the DNA substrate of a corresponding DNase I polypeptide, functional fragment thereof, or variant thereof that does not comprise the one or more non-standard amino acids after being present in the environment for at least 1, 2, 3, 4, 5, 6, 7, 8, 9, 10, 15, 20, 25, 30, 40, or 50 minutes.

In some embodiments, the stabilized DNase I polypeptide has at least a 1.1, 1.2, 1.3, 1.4, 1.5, 1.6, 1.7, 1.8, 1.9, 2, 3, 4, 5, 6, 7, 8, 10, 20, 30, 40, 50, 60, 70, 80, 90 or 100 fold higher endonuclease activity for a DNA substrate after being present in an environment for at least 1, 2, 3, 4, 5, 6, 7, 8, 9, 10, 12, 18, or 24 hours than an endonuclease activity for the DNA substrate of a corresponding DNase I polypeptide, functional fragment thereof, or variant thereof that does not comprise the one or more non-standard amino acids after being present in the environment for at least 1, 2, 3, 4, 5, 6, 7, 8, 9, 10, 12, 18, or 24 hours.

In some embodiments, the DNA substrate is genomic DNA.

In some embodiments, the environment is an environment with a temperature of from 4° C.-98° C.

In some embodiments, the environment is an environment with a lysis buffer.

In some embodiments, the environment is an environment with a detergent at a concentration of from 0.01% to 20%.

In some embodiments, the detergent is a non-ionic detergent.

In some embodiments, the detergent is an ionic detergent.

In some embodiments, the environment comprises a divalent cation at a concentration of from 0.01 mM to 100 mM.

In some embodiments, the divalent cation is selected from the group consisting of $Mg^{2+}$, $Mn^{2+}$, $Ca^{2+}$, $Co^{2+}$, and $Zn^{2+}$.

In some embodiments, the environment comprises a reducing agent at a concentration of from 0.01 mM to 100 mM.

In some embodiments, the environment has a pH of from 5-9.

In some embodiments, the environment has a pH of from 6-8.

In some embodiments, the environment has a pH of from 7-8.

In some embodiments, the environment has a salt concentration of from 10 mM to 1 M.

In some embodiments, the environment is within a droplet.

In some embodiments, the environment is a blood circulatory system.

In some embodiments, the environment has a reduction potential that is less than −150 mV, −160 mV, −170 mV, −180 mV, −190 mV, −200 mV, −210 mV, −220 mV, −230 mV, −240 mV, or −250 mV, −260 mV, −270 mV, −280 mV, −290 mV, −300 mV, −310 mV, −320 mV, −330 mV, −340 mV, or −350 mV, −360 mV, −370 mV, −380 mV, −390 mV, −400 mV, −410 mV, −420 mV, −430 mV, −440 mV, or −450 mV, −460 mV, −470 mV, −480 mV, −490 mV, −500 mV, −510 mV, −520 mV, −530 mV, −540 mV, or −550 mV, −560 mV, −570 mV, −580 mV, −590 mV, or −600 mV.

In some embodiments, the stabilized DNase I polypeptide, functional fragment thereof, or variant thereof, is recombinant.

In some embodiments, the stabilized DNase I polypeptide, functional fragment thereof, or variant thereof, is bovine DNase I.

In some embodiments, a composition comprising a polynucleotide encoding the composition disclosed herein.

In some embodiments, the polynucleotide is a vector.

In some embodiments, a bond directly linking two of the one or more non-standard amino acids of the stabilized DNase I polypeptide does not break in an environment, wherein the bond directly linking two of the one or more standard amino acids of the corresponding DNase I polypeptide does break in the same environment.

In some embodiments, the method of making the composition disclosed herein comprises expressing an amino acid sequence of the stabilized DNase I polypeptide.

In some embodiments, expressing comprises expressing in a cell or in vitro.

In some embodiments, the cell is a bacterial cell.

In some embodiments, the cell is a genomically recoded cell.

In some embodiments, the cell comprises a reassigned codon recognized by a stabilizing non-standard amino acid tRNA comprising an anticodon corresponding to the reassigned codon.

In some embodiments, the amino acid sequence of the stabilized DNase I polypeptide is encoded by a polynucleotide sequence comprising at least one codon of a natural amino acid that has been replaced by the reassigned codon.

In some embodiments, the stabilizing non-standard amino acid tRNA is a selenocysteine tRNA.

In some embodiments, the method comprises culturing the cell under conditions in which the amino acid sequence of the stabilized DNase I polypeptide is expressed.

In some embodiments, the reassigned codon is UAG, UAA, UGA, or a combination thereof.

In some aspects, provided herein is a method comprising contacting DNA substrate that is in a buffer, in reaction environment or on a solid surface to a stabilized deoxyribonuclease I (DNase I) polypeptide comprising one or more non-standard amino acids, a functional fragment thereof, or a variant thereof; wherein the stabilized DNase I polypeptide, functional fragment thereof, or variant thereof catalyzes cleavage or fragmentation of the DNA substrate at a higher rate than a corresponding DNase I polypeptide, functional fragment thereof, or variant thereof that does not comprise the one or more non-standard amino acids.

In some embodiments, the stabilized DNase I polypeptide, functional fragment thereof, or variant thereof is the stabilized DNase I polypeptide, functional fragment thereof, or variant disclosed elsewhere herein.

In some embodiments, the DNA substrate is genomic DNA.

In some embodiments, the DNA substrate is from a single cell.

In some embodiments, the method comprises forming a plurality of vessels each comprising a single cell of a plurality of cells; the stabilized DNase I polypeptide, functional fragment thereof, or variant thereof; and a lysis buffer.

In some embodiments, the method further comprises lysing the single cell, thereby releasing the DNA substrate from the single cell.

In some embodiments, the method further comprises barcoding the DNA substrate or fragments thereof.

In some embodiments, the method further comprises amplifying the DNA substrate or fragments thereof.

In some embodiments, the amplifying comprises clonal amplification.

In some embodiments, the method further comprises sequencing the DNA substrate or fragments thereof.

In some embodiments, the sequencing comprises whole genome sequencing.

In some embodiments, the sequencing comprises high throughput sequencing, massively parallel sequencing, Sanger sequencing, or next generation sequencing.

In some embodiments, the plurality of vessels comprises a solid support.

In some embodiments, the DNA substrate is not attached to a solid support in a vessel.

In some embodiments, the buffer, the reaction environment or the solid surface comprises primers specific to a sequence of the DNA substrate or fragments thereof.

In some embodiments, the plurality of cells comprises at least 2, 3, 4, 5, 5.5 6, 6.5 7, 8, 9, 10, 11, 12, 13, 14, 15, 16, 17, 18, 19, 20, 30, 40, 50, 60, 70, 80, 90, 100, 200, 300, 400, 500, 600, 700, 800, 900, 1000, 2000, 3000, 4000, 5000, 6000, 7000, 8000, 9000, 10,000, 15,000, 20,000, 25,000, 30,000, 35,000, 40,000, 45,000, 50,000, 60,000, 70,000, 80,000, 90,000, 100,000, 200,000, 300,000, 400,000, 500,000, 600,000, 700,000, 800,000, 900,000, $1\times10^6$, $2\times10^6$, $3\times10^6$, $4\times10^6$, $5\times10^6$, $6\times10^6$, $7\times10^6$, $8\times10^6$, $9\times10^6$, $1\times10^7$, $2\times10^7$, $3\times10^7$, $4\times10^7$, $5\times10^7$, $6\times10^7$, $7\times10^7$, $8\times10^7$, $9\times10^7$, $1\times10^8$, $2\times10^8$, $3\times10^8$, $4\times10^8$, $5\times10^8$, $6\times10^8$, $7\times10^8$, $8\times10^8$, $9\times10^8$, $1\times10^9$, $2\times10^9$, $3\times10^9$, $4\times10^9$, $5\times10^9$, $6\times10^9$, $7\times10^9$, $8\times10^9$, $9\times10^9$, $2\times10^{10}$, $3\times10^{10}$, $4\times10^{10}$, $5\times10^{10}$, $6\times10^{10}$, $7\times10^{10}$, $8\times10^{10}$, $9\times10^{10}$, $1\times10^{11}$, $2\times10^{11}$, $3\times10^{11}$, $4\times10^{11}$, $5\times10^{11}$, $6\times10^{11}$, $7\times10^{11}$, $8\times10^{11}$, $9\times10^{11}$, $1\times10^{12}$, $2\times10^{12}$, $3\times10^{12}$, $4\times10^{12}$, $5\times10^{12}$, $6\times10^{12}$, $7\times10^{12}$, $8\times10^{12}$, or $9\times10^{12}$ cells.

In some embodiments, the plurality of cells is from one or more biological samples.

In some embodiments, the one or more biological samples comprises at least 2, 3, 4, 5, 10, 20, 30, 40, 50, 60, 70, 80, 90 or 100 or more samples.

In some embodiments, the one or more biological sample is from a subject with a disease.

In some embodiments, the plurality of cells comprises a plurality of bacterial cells or a plurality of fungal cells.

In some embodiments, the plurality of cells comprises a plurality of immune cells.

In some embodiments, the plurality of cells comprises a plurality of diseased cells.

In some embodiments, the plurality of cells comprises a plurality of cancer cells.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The features of the present disclosure are set forth with particularity in the appended claims. A better understanding of the features and advantages of the present disclosure will be obtained by reference to the following detailed description that sets forth illustrative embodiments, in which the principles of the disclosure are utilized, and the accompanying drawings of which:

FIG. 1 depicts an agarose gel of 50 ng double stranded DNA added to a mixture of 0 mm DTT (lane 6), 50 mm DTT (lane 7), 30 ng of seleno-DNase (GST-seleno-DNase I fusion) or equimolar disulfide DNase (wild-type DNase I purified from bovine pancreas, Sigma DN25) after incubation of the DNase for 2 hours at 37° C. in reaction buffer (NEB B0303S) supplemented with either 0 mM DTT (−DTT, lanes 2 and 3) or 50 mM DTT (+DTT, lanes 4 and 5). The double stranded DNA was added to each mixture and digested for 30 min at 37° C. followed by 10 min of heat inactivation at 75° C. Both enzymes digested the DNA in 0 mM DTT but only seleno-DNase digested the DNA in 50 mM DTT.

DETAILED DESCRIPTION OF THE INVENTION

Definitions

The term "encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (e.g., rRNA, tRNA and mRNA) or a defined sequence of amino acids and the biological properties resulting therefrom. Thus, a gene, cDNA, or RNA, encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

The term "endogenous" refers to any material from or produced inside an organism, cell, tissue or system.

The term "exogenous" refers to any material introduced from or produced outside an organism, cell, tissue or system.

The term "expression" refers to the transcription and/or translation of a particular nucleotide sequence driven by a promoter.

The term "homologous" or "identity" refers to the subunit sequence identity between two polymeric molecules, e.g., between two nucleic acid molecules, such as, two DNA molecules or two RNA molecules, or between two polypeptide molecules. When a subunit position in both of the two molecules is occupied by the same monomeric subunit; e.g., if a position in each of two DNA molecules is occupied by adenine, then they are homologous or identical at that position. The homology between two sequences is a direct function of the number of matching or homologous positions; e.g., if half (e.g., five positions in a polymer ten subunits in length) of the positions in two sequences are homologous, the two sequences are 50% homologous; if 90% of the positions (e.g., 9 of 10), are matched or homologous, the two sequences are 90% homologous.

The term "isolated" means altered or removed from the natural state. For example, a nucleic acid or a peptide naturally present in a living animal is not "isolated," but the same nucleic acid or peptide partially or completely separated from the coexisting materials of its natural state is "isolated." An isolated nucleic acid or protein can exist in substantially purified form, or can exist in a non-native environment such as, for example, a host cell.

In the context of the present invention, the following abbreviations for the commonly occurring nucleic acid bases are used. "A" refers to adenosine, "C" refers to cytosine, "G" refers to guanosine, "T" refers to thymidine, and "U" refers to uridine.

The term "operably linked" or "transcriptional control" refers to functional linkage between a regulatory sequence and a heterologous nucleic acid sequence resulting in expression of the latter. For example, a first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Operably linked DNA sequences can be contiguous with each other and, e.g., where necessary to join two protein coding regions, are in the same reading frame.

The term "nucleic acid" or "polynucleotide" refers to deoxyribonucleic acids (DNA) or ribonucleic acids (RNA) and polymers thereof in either single- or double-stranded form. Unless specifically limited, the term encompasses nucleic acids containing known analogues of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions), alleles, orthologs, SNPs, and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., Nucleic Acid Res. 19:5081 (1991); Ohtsuka et al., J. Biol. Chem. 260:2605-2608 (1985); and Rossolini et al., Mol. Cell. Probes 8:91-98 (1994)).

The term "amino acid" as used herein refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, gamma-carboxyglutamate, and O-phosphoserine. The term "amino acid analogs" as used herein refers to compounds that have the same basic chemical structure as a naturally occurring amino acid, i.e., an alpha carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. The term "amino acid mimetics" as used herein refers to chemical compounds that have a structure that is different from the general chemical structure of an amino acid, but that functions in a manner similar to a naturally occurring amino acid.

The term "non-standard amino acid" refers to any amino acid other than the 20 standard amino acids (alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine, and valine). Selenocysteine is a non-standard amino acid (NSAA).

The terms "peptide," "polypeptide," and "protein" are used interchangeably, and refer to a compound comprised of amino acid residues covalently linked by peptide bonds. A protein or peptide must contain at least two amino acids, and no limitation is placed on the maximum number of amino acids that can comprise a protein's or peptide's sequence. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. A polypeptide includes a natural peptide, a recombinant peptide, or a combination thereof.

The term "promoter" refers to a DNA sequence recognized by the transcription machinery of the cell, or introduced synthetic machinery, required to initiate the specific transcription of a polynucleotide sequence.

The term "constitutive" promoter refers to a nucleotide sequence which, when operably linked with a polynucleotide which encodes or specifies a gene product, causes the gene product to be produced in a cell under most or all physiological conditions of the cell.

The term "inducible" promoter refers to a nucleotide sequence which, when operably linked with a polynucleotide which encodes or specifies a gene product, causes the gene product to be produced in a cell substantially only when an inducer which corresponds to the promoter is present in the cell.

The term "transfected" or "transformed" or "transduced" refers to a process by which exogenous nucleic acid is transferred or introduced into the host cell. A "transfected" or "transformed" or "transduced" cell is one which has been transfected, transformed or transduced with exogenous nucleic acid. The cell includes the primary subject cell and its progeny.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. As another example, a range such as 95-99% identity, includes something with 95%, 96%, 97%, 98% or 99% identity, and includes subranges such as 96-99%, 96-98%, 96-97%.

Unless defined otherwise, all technical and scientific terms used herein have the same meaning as is commonly understood by one of skill in the art to which the claimed subject matter belongs. It is to be understood that the foregoing general description and the following detailed description are exemplary and explanatory only and are not restrictive of any subject matter claimed. In this application, the use of the singular includes the plural unless specifically stated otherwise.

Non-Standard Amino Acid Containing Compositions

The use of non-standard amino acids in proteins offers the possibility of polypeptides having greatly expanded functionality that could be exploited for wide range of applications. For example, by incorporation of selenocysteine into polypeptides it may be possible to develop enzymes having enhanced levels of stability or activity and to produce highly active therapeutic polypeptides. However, these approaches have, to date, been hampered by the inability to produce organisms that stability retain translation pathways that predictable and reliably incorporate selenocysteine into encoded polypeptides. Studies detailed herein demonstrate a stable system for selection of tRNA molecules that can incorporate selenocysteine and for production of polypeptides that incorporate selenocysteine positions. Importantly, this system can be easily moved from one organism to another without the need of re-engineering.

Over 100 NSAAs with diverse chemistries have been synthesized and co-translationally incorporated into proteins using evolved orthogonal aminoacyl-tRNA synthetase (aaRSs)/tRNA pairs. Non-standard amino acids have been designed based on tyrosine or pyrrolysine. An aaRS/tRNA may be provided on a plasmid or into the genome of the genomically recoded organism. An orthogonal aaRS/tRNA pair can be used to bioorthogonally incorporate NSAAs into proteins. Vector-based overexpression systems may be used to outcompete natural codon function with its reassigned function. If one completely abolishes natural UAG translation function, far lower aaRS/tRNA function may be sufficient to achieve efficient NSAA incorporation. Genomically recoded organism (GRO)-based NSAA incorporation can use either vector- and/or genome-based aaRS/tRNA pairs. Genome-based aaRS/tRNA pairs have been used to reduce the mis-incorporation of standard amino acids in the absence of available NSAAs. Since the UAG codon function has been completely reassigned in the genomically recoded organism, NSAAs, such as selenocysteine, can be incorporated in the genomically recoded organism without any phenotypic consequences. NSAA incorporation in the genomically recoded organism may involve supplementing the growth media with the non-standard amino acid, such as selenocysteine, and an inducer for the aaRS. Alternatively, the aaRS may be expressed constitutively. Alternatively, as in the present disclosure, the endogenous seryl-tRNA synthetase may be used to serylate selenocysteine tRNA, which tRNA is acted upon by enzymes comprising SelA to produce tRNAsec (selenocysteine charged tRNA). Media may be supplemented with a selenium source like sodium selenite to improve production of tRNAsec. The desired protein can be overexpressed using any desired protein overexpression system (e.g., T7-RNAP, constitutive incorporation, or inducible expression based on IPTG/allolactose, anhydrotetracycline, arabinose, rhamnose, or other inducible systems). The protein cross-link (diselenide bond) may form spontaneously based on proximity-based geometric catalysis during protein folding, and the protein can be handled as any other over-expressed product.

The inventors have developed polypeptides and methods to produce polypeptides in genomically recoded organisms (GRO) that fold into biologics that, for example, are stabilized by diselenide bonds between selenocysteine amino acids. Whereas disulfide bonds between cysteine amino acids have a redox potential of about −220 mV, diselenide bonds have a redox potential of about −380 mV. Since the bacterial cytosol typically has a redox potential of about −280 to −300 mV, diselenides but not disulfides avoid reduction so that they form and persist in the cytosol. Since diselenides have the same geometric bond angles and torsions as disulfides, as well as very similar bond lengths, they can be substituted into polypeptides without disrupting the three-dimensional structure of the polypeptide. Further, since intended in vivo environments like blood contain reducing agents like glutathione, albumin, and thioredoxin, disulfides in polypeptides can be reduced, causing the polypeptide to unfold and, in the case of multiple disulfides, "scramble" the disulfides so that incorrect cysteines are bonded to each other. Both of these result in abrogation of the intended biological activity of the polypeptide. The lower redox potential of diselenides renders them resistant to reduction when exposed to blood serum or purified reducing components of blood serum, endowing them with a longer blood serum half-life than disulfide-bearing counterparts.

While peptides bearing diselenide-forming selenocysteines may be produced in vitro by solid phase peptide synthesis, the process does not scale tractably to the yields necessary for therapeutic applications, particularly for proteins. However, in vivo production of recombinant selenoproteins is limited by strict sequence requirements on where selenocysteine may appear in proteins. In particular, a selenocysteine insertion sequence (SECIS) element must appear in the coding DNA sequence at the selenocysteine incorporation site in order to recruit endogenous selenocysteine translation machinery, comprising a specialized elongation factor (SelB). Instead, a recoded strain of E. coli can be used, which has an unassigned codon, such as an amber stop codon, together with an engineered selenocysteine tRNA with an anti-amber anticodon that permits targeted placement of selenocysteine into polypeptides by introduction of the amber stop codon into the corresponding DNA coding sequence. The modified tRNA interacts with the endogenous elongation factor EF-Tu. Other codons can be recoded, typically rare codons, as is known in the art. A codon on an mRNA and an anti-codon on a tRNA are typically triplets of complementary base sequences.

Recoded proteins may be synthesized in bacteria, such as E. coli cells, or in vitro, in translation or linked transcription-translation systems. Genes or mRNA encoding such recoded proteins are non-naturally occurring, and are variants of naturally occurring coding sequences. Although many of the proteins that we show in the associated sequence listing have all cysteine residues which participate in disulfide bonds replaced with selenocysteine residues, all cysteine residues need not be replaced to gain the benefits of the substitution. Even one diselenide bond may improve the stability of a protein. Any number of diselenide bonds (selenocysteine pairs) may be substituted for disulfide bonds in the proteins. If a protein has N disulfide bonds, the protein may have anywhere from N, N minus 1, N minus 2, N minus 3, N minus 4, . . . down to 1 such bond. It is also possible to form a bond between cysteine and selenocysteine residues called a selenylsulfide. This bond has a lower redox potential (~−270 mv) than a disulfide (−220 mv) but not than bacterial cytoplasm (−280 mv). The selenylsulfide bond may be used to increase resistance to reduction in certain redox environments. Selenylsulfides may be used in place of diselenides using methods described here by substituting selenocysteine for a single disulfide bonded cysteine, or by substituting cysteine for a single diselenide bonded selenocysteine.

Sequences of disulfide-stabilized biologics with substituted selenocysteines can be produced in the cytosol of E. coli using our method at the mg/L scale in standard laboratory shaker flasks, and scaled to g/L production in microbial fermenters.

Enzymes with different combinations of diselenide bonds and disulfides include, but are not limited to, nucleases (such as DNases and RNases), polymerases, ligases, reverse transcriptases, proteases, restriction endonucleases, and carbon fixing enzymes (e.g., carbon capturing enzymes).

Any cysteine in an enzyme disclosed herein may be maintained as a selenocysteine so long as the presence of the selenocysteine does not interfere with the expression, folding, or intended function of the polypeptide. Methods are provided herein for producing and verifying the presence of selenocysteines participating in the intended diselenide bonds for various enzymes, including, but not limited to, nucleases (such as DNases and RNases), polymerases, ligases, reverse transcriptases, proteases, restriction endonucleases, and carbon fixing enzymes (e.g., carbon capturing enzymes).

Stabilized enzymes may be made and used according to the invention with diselenide bonds between two selenocysteine residues. This technique and modification can be useful for producing enzymes that maintain activity even in harsh conditions such as reducing environments. Provided herein are stabilized enzymes containing non-standard amino acids that have enzymatic activity in harsh conditions, such as reducing buffers or lysis buffers, that is higher than a corresponding enzyme without the non-standard amino acids under the same conditions. The stabilized enzymes can comprise a stabilized DNase I polypeptide. Also provided herein are polynucleotides encoding these stabilized enzymes, cells for expressing and/or producing these stabilized enzymes, and methods of use of these stabilized enzymes.

Enzymes with different combinations of diselenide bonds and disulfides include, but are not limited to, nucleases (such as DNases and RNases), polymerases, ligases, reverse transcriptases, proteases, restriction endonucleases, and carbon fixing enzymes (e.g., carbon capturing enzymes).

In some embodiments, a nuclease may be made and used according to the invention with diselenide bonds between two selenocysteine residues. Exemplary nucleases include, but are not limited to, DNases (e.g., bovine DNase I), RNases and the like. For example, DNase I has two disulfide bonds. For example, RNase A has 4 disulfide bonds. In some embodiments, a RNase A enzyme comprises 2, 4, 6, or 8 selenocysteine residues. In some embodiments, a RNase A enzyme comprises at least 1, 2, 3, or 4 diselenide bonds. For example, RNase 3 has 4 disulfide bonds. In some embodiments, a RNase 3 enzyme comprises at least 2, 4, 6, or 8 selenocysteine residues. In some embodiments, a RNase 3 enzyme comprises at least 1, 2, 3, or 4 diselenide bonds. For example, benzonase (e.g., Serratia marcescens nuclease) comprises at least two essential disulfide bonds and is a 30 kDa homodimer. In some embodiments, a benzonase comprises at least 2 or 4 selenocysteine residues. In some embodiments, a benzonase comprises at least 1 or 2 diselenide bonds.

In some embodiments, a nuclease can comprise one or more non-standard amino acids. In some embodiments, a nuclease can comprise one or more selenocysteine residues. In some embodiments, a nuclease can comprise a diselenide bond between two selenocysteine residues. The diselenide bonds may be intramolecular or intermolecular. In some embodiments, a nuclease can comprise one or more diselenide bonds. In some embodiments, a nuclease comprising one or more non-standard amino acids has enzymatic activity in harsh conditions, such as reducing buffers or lysis buffers, that is higher than a corresponding nuclease without the non-standard amino acids under the same conditions.

For example, a nuclease provided herein comprising one or more non-standard amino acids, such as one or more selenocysteine residues, can cleave a bond of a polynucleotide substrate with an activity that is at least 1.1, 1.2, 1.3, 1.4, 1.5, 1.6, 1.7, 1.8, 1.9, 2, 2.1, 2.2, 2.3, 2.4, 2.5, 3, 3.5, 4, 4.5, 5, 5.5, 6, 6.5, 7, 7.5, 8, 8.5, 9, 9.5, 10, 10.5, 11, 12, 13, 14, 15, 16, 17, 18, 19, 20, 25, 30, 35, 40, 45, 50, 55, 60, 65, 70, 75, 80, 85, 90, 95, 100, 200, 300, 400, 500, 600, 700, 800, 900, or 1000 times higher than a corresponding nuclease without the one or more non-standard amino acids.

For example, a nuclease provided herein comprising one or more non-standard amino acids, such as one or more selenocysteine residues, can cleave a bond of a polynucleotide substrate in a buffer with an activity that is at least 1.1, 1.2, 1.3, 1.4, 1.5, 1.6, 1.7, 1.8, 1.9, 2, 2.1, 2.2, 2.3, 2.4, 2.5, 3, 3.5, 4, 4.5, 5, 5.5, 6, 6.5, 7, 7.5, 8, 8.5, 9, 9.5, 10, 10.5, 11, 12, 13, 14, 15, 16, 17, 18, 19, 20, 25, 30, 35, 40, 45, 50, 55, 60, 65, 70, 75, 80, 85, 90, 95, 100, 200, 300, 400, 500, 600, 700, 800, 900, or 1000 times higher than a corresponding nuclease without the one or more non-standard amino acids in the same buffer.

For example, a nuclease provided herein comprising one or more non-standard amino acids, such as one or more selenocysteine residues, can cleave a bond of a polynucleotide substrate in a buffer comprising a detergent, a reducing reagent, and/or a reducing enzyme (e.g., a reductase) with an activity that is at least 1.1, 1.2, 1.3, 1.4, 1.5, 1.6, 1.7, 1.8, 1.9, 2, 2.1, 2.2, 2.3, 2.4, 2.5, 3, 3.5, 4, 4.5, 5, 5.5, 6, 6.5, 7, 7.5, 8, 8.5, 9, 9.5, 10, 10.5, 11, 12, 13, 14, 15, 16, 17, 18, 19, 20, 25, 30, 35, 40, 45, 50, 55, 60, 65, 70, 75, 80, 85, 90, 95, 100, 200, 300, 400, 500, 600, 700, 800, 900, or 1000 times higher than a corresponding nuclease without the one or more non-standard amino acids in the same buffer comprising the detergent, the reducing reagent, and/or the reducing enzyme (e.g., a reductase).

For example, a nuclease provided herein comprising one or more non-standard amino acids, such as one or more selenocysteine residues, can cleave a bond of a polynucleotide substrate in a buffer with a redox potential of less than about −150 mV, with an activity that is at least 1.1, 1.2, 1.3, 1.4, 1.5, 1.6, 1.7, 1.8, 1.9, 2, 2.1, 2.2, 2.3, 2.4, 2.5, 3, 3.5, 4, 4.5, 5, 5.5, 6, 6.5, 7, 7.5, 8, 8.5, 9, 9.5, 10, 10.5, 11, 12, 13, 14, 15, 16, 17, 18, 19, 20, 25, 30, 35, 40, 45, 50, 55, 60, 65, 70, 75, 80, 85, 90, 95, 100, 200, 300, 400, 500, 600, 700, 800, 900, or 1000 times higher than a corresponding nuclease without the one or more non-standard amino acids in a buffer with the same redox potential. For example, a nuclease provided herein comprising one or more non-standard amino acids, such as one or more selenocysteine residues, can cleave a bond of a polynucleotide substrate in a buffer with a redox potential of less than about −160 mV, less than about −170 mV, less than about −180 mV, less than about −190 mV, less than about −200 mV, less than about −210 mV, less than about −220 mV, less than about −230 mV, less than about −240 mV, or less than about −250 mV, less than about −260 mV, less than about −270 mV, less than about −280 mV, less than about −290 mV, less than about −300 mV, less than about −310 mV, less than about −320 mV, less than about −330 mV, less than about −340 mV, or less than about −350 mV, less than about −360 mV, less than about −370 mV, less than about −380 mV, less than about −390 mV, less than about −400 mV, less than about −410 mV, less than about −420 mV, less than about −430 mV, less than about −440 mV, or less than about −450 mV, less than about −460 mV, less than about −470 mV, less than about −480 mV, less than about −490 mV, less than about −500 mV, less than about −510 mV, less than about −520 mV, less than about −530 mV, less than about −540 mV, or less than about −550 mV, less than about −560 mV, less than about −570 mV, less than about −580 mV, less than about −590 mV, or less than about −600 mV, with an activity that is at least 1.1, 1.2, 1.3, 1.4, 1.5, 1.6, 1.7, 1.8, 1.9, 2, 2.1, 2.2, 2.3, 2.4, 2.5, 3, 3.5, 4, 4.5, 5, 5.5, 6, 6.5, 7, 7.5, 8, 8.5, 9, 9.5, 10, 10.5, 11, 12, 13, 14, 15, 16, 17, 18, 19, 20, 25, 30, 35, 40, 45, 50, 55, 60, 65, 70, 75, 80, 85, 90, 95, 100, 200, 300, 400, 500, 600, 700, 800, 900, or 1000 times higher than a corresponding nuclease without the one or more non-standard amino acids in a buffer with the same redox potential.

In some embodiments, a polymerase may be made and used according to the invention with diselenide bonds between two selenocysteine residues. In some embodiments, a polymerase can comprise one or more non-standard amino acids. In some embodiments, a polymerase can comprise one or more selenocysteine residues. In some embodiments, a polymerase can comprise a diselenide bond between two selenocysteine residues. The diselenide bonds may be intramolecular or intermolecular. In some embodiments, a polymerase can comprise one or more diselenide bonds. In some embodiments, a polymerase comprising one or more non-standard amino acids has enzymatic activity in harsh conditions, such as reducing buffers or lysis buffers, that is higher than a corresponding polymerase without the non-standard amino acids under the same conditions.

For example, a polymerase provided herein comprising one or more non-standard amino acids, such as one or more selenocysteine residues, can catalyze a polymerase reaction with an activity that is at least 1.1, 1.1, 1.2, 1.3, 1.4, 1.5, 1.6, 1.7, 1.8, 1.9, 2, 2.1, 2.2, 2.3, 2.4, 2.5, 3, 3.5, 4, 4.5, 5, 5.5, 6, 6.5, 7, 7.5, 8, 8.5, 9, 9.5, 10, 10.5, 11, 12, 13, 14, 15, 16, 17, 18, 19, 20, 25, 30, 35, 40, 45, 50, 55, 60, 65, 70, 75, 80, 85, 90, 95, 100, 200, 300, 400, 500, 600, 700, 800, 900, or 1000 times higher than a corresponding polymerase without the one or more non-standard amino acids.

For example, a polymerase provided herein comprising one or more non-standard amino acids, such as one or more selenocysteine residues, can catalyze a polymerase reaction in a buffer with an activity that is at least 1.1, 1.2, 1.3, 1.4, 1.5, 1.6, 1.7, 1.8, 1.9, 2, 2.1, 2.2, 2.3, 2.4, 2.5, 3, 3.5, 4, 4.5, 5, 5.5, 6, 6.5, 7, 7.5, 8, 8.5, 9, 9.5, 10, 10.5, 11, 12, 13, 14, 15, 16, 17, 18, 19, 20, 25, 30, 35, 40, 45, 50, 55, 60, 65, 70, 75, 80, 85, 90, 95, 100, 200, 300, 400, 500, 600, 700, 800, 900, or 1000 times higher than a corresponding polymerase without the one or more non-standard amino acids in the same buffer.

For example, a polymerase provided herein comprising one or more non-standard amino acids, such as one or more selenocysteine residues, can catalyze a polymerase reaction in a buffer comprising a detergent, a reducing reagent, and/or a reducing enzyme (e.g., a reductase) with an activity that is at least 1.1, 1.1, 1.2, 1.3, 1.4, 1.5, 1.6, 1.7, 1.8, 1.9, 2, 2.1, 2.2, 2.3, 2.4, 2.5, 3, 3.5, 4, 4.5, 5, 5.5, 6, 6.5, 7, 7.5, 8, 8.5, 9, 9.5, 10, 10.5, 11, 12, 13, 14, 15, 16, 17, 18, 19, 20, 25, 30, 35, 40, 45, 50, 55, 60, 65, 70, 75, 80, 85, 90, 95, 100, 200, 300, 400, 500, 600, 700, 800, 900, or 1000 times higher than a corresponding polymerase without the one or more non-standard amino acids in the same buffer comprising the detergent, the reducing reagent, and/or the reducing enzyme (e.g., a reductase).

For example, a polymerase provided herein comprising one or more non-standard amino acids, such as one or more selenocysteine residues, can catalyze a polymerase reaction in a buffer with a redox potential of less than about −150 mV, with an activity that is at least 1.1, 1.2, 1.3, 1.4, 1.5, 1.6, 1.7, 1.8, 1.9, 2, 2.1, 2.2, 2.3, 2.4, 2.5, 3, 3.5, 4, 4.5, 5, 5.5, 6, 6.5, 7, 7.5, 8, 8.5, 9, 9.5, 10, 10.5, 11, 12, 13, 14, 15, 16, 17, 18, 19, 20, 25, 30, 35, 40, 45, 50, 55, 60, 65, 70, 75, 80, 85, 90, 95, 100, 200, 300, 400, 500, 600, 700, 800, 900, or 1000 times higher than a corresponding polymerase without the one or more non-standard amino acids in a buffer with the same redox potential. For example, a polymerase provided herein comprising one or more non-standard amino acids, such as one or more selenocysteine residues, can catalyze a polymerase reaction in a buffer with a redox potential of less than about −160 mV, less than about −170 mV, less than about −180 mV, less than about −190 mV, less than about −200 mV, less than about −210 mV, less than about −220 mV, less than about −230 mV, less than about −240 mV, or less than about −250 mV, less than about −260 mV, less than about −270 mV, less than about −280 mV, less than about −290 mV, less than about −300 mV, less than about −310 mV, less than about −320 mV, less than about −330 mV, less than about −340 mV, or less than about −350 mV, less than about −360 mV, less than about −370 mV, less than about −380 mV, less than about −390 mV, less than about −400 mV, less than about −410 mV, less than about −420 mV, less than about −430 mV, less than about −440 mV, or less than about −450 mV, less than about −460 mV, less than about −470 mV, less than about −480 mV, less than about −490 mV, less than about −500 mV, less than about −510 mV, less than about −520 mV, less than about −530 mV, less than about −540 mV, or less than about −550 mV, less than about −560 mV, less than about −570 mV, less than about −580 mV, less than about −590 mV, or less than about −600 mV, with an activity that is at least 1.1, 1.2, 1.3, 1.4, 1.5, 1.6, 1.7, 1.8, 1.9, 2, 2.1, 2.2, 2.3, 2.4, 2.5, 3, 3.5, 4, 4.5, 5, 5.5, 6, 6.5, 7, 7.5, 8, 8.5, 9, 9.5, 10, 10.5, 11, 12, 13, 14, 15, 16, 17, 18, 19, 20, 25, 30, 35, 40, 45, 50, 55, 60, 65, 70, 75, 80, 85, 90, 95, 100, 200, 300, 400, 500, 600, 700, 800, 900, or 1000 times higher than a corresponding polymerase without the one or more non-standard amino acids in a buffer with the same redox potential.

In some embodiments, a ligase may be made and used according to the invention with diselenide bonds between two selenocysteine residues. In some embodiments, a ligase can comprise one or more non-standard amino acids. In some embodiments, a ligase can comprise one or more selenocysteine residues. In some embodiments, a ligase can comprise a diselenide bond between two selenocysteine residues. The diselenide bonds may be intramolecular or intermolecular. In some embodiments, a ligase can comprise one or more diselenide bonds. In some embodiments, a ligase comprising one or more non-standard amino acids has enzymatic activity in harsh conditions, such as reducing buffers or lysis buffers, that is higher than a corresponding ligase without the non-standard amino acids under the same conditions.

For example, a ligase provided herein comprising one or more non-standard amino acids, such as one or more selenocysteine residues, can ligate two or more nucleic acids together with an activity that is at least 1.1, 1.2, 1.3, 1.4, 1.5, 1.6, 1.7, 1.8, 1.9, 2, 2.1, 2.2, 2.3, 2.4, 2.5, 3, 3.5, 4, 4.5, 5, 5.5, 6, 6.5, 7, 7.5, 8, 8.5, 9, 9.5, 10, 10.5, 11, 12, 13, 14, 15, 16, 17, 18, 19, 20, 25, 30, 35, 40, 45, 50, 55, 60, 65, 70, 75, 80, 85, 90, 95, 100, 200, 300, 400, 500, 600, 700, 800, 900, or 1000 times higher than a corresponding ligase without the one or more non-standard amino acids.

For example, a ligase provided herein comprising one or more non-standard amino acids, such as one or more selenocysteine residues, can ligate two or more nucleic acids together in a buffer with an activity that is at least 1.1, 1.2, 1.3, 1.4, 1.5, 1.6, 1.7, 1.8, 1.9, 2, 2.1, 2.2, 2.3, 2.4, 2.5, 3, 3.5, 4, 4.5, 5, 5.5, 6, 6.5, 7, 7.5, 8, 8.5, 9, 9.5, 10, 10.5, 11, 12, 13, 14, 15, 16, 17, 18, 19, 20, 25, 30, 35, 40, 45, 50, 55, 60, 65, 70, 75, 80, 85, 90, 95, 100, 200, 300, 400, 500, 600, 700, 800, 900, or 1000 times higher than a corresponding ligase without the one or more non-standard amino acids in the same buffer.

For example, a ligase provided herein comprising one or more non-standard amino acids, such as one or more selenocysteine residues, can ligate two or more nucleic acids together in a buffer comprising a detergent, a reducing reagent, and/or a reducing enzyme (e.g., a reductase) with an activity that is at least 1.1, 1.2, 1.3, 1.4, 1.5, 1.6, 1.7, 1.8, 1.9, 2, 2.1, 2.2, 2.3, 2.4, 2.5, 3, 3.5, 4, 4.5, 5, 5.5, 6, 6.5, 7, 7.5, 8, 8.5, 9, 9.5, 10, 10.5, 11, 12, 13, 14, 15, 16, 17, 18, 19, 20, 25, 30, 35, 40, 45, 50, 55, 60, 65, 70, 75, 80, 85, 90, 95, 100, 200, 300, 400, 500, 600, 700, 800, 900, or 1000 times higher than a corresponding ligase without the one or more non-standard amino acids in the same buffer comprising the detergent, the reducing reagent, and/or the reducing enzyme (e.g., a reductase).

For example, a ligase provided herein comprising one or more non-standard amino acids, such as one or more selenocysteine residues, can ligate two or more nucleic acids together in a buffer with a redox potential of less than about −150 mV, with an activity that is at least 1.1, 1.2, 1.3, 1.4, 1.5, 1.6, 1.7, 1.8, 1.9, 2, 2.1, 2.2, 2.3, 2.4, 2.5, 3, 3.5, 4, 4.5, 5, 5.5, 6, 6.5, 7, 7.5, 8, 8.5, 9, 9.5, 10, 10.5, 11, 12, 13, 14, 15, 16, 17, 18, 19, 20, 25, 30, 35, 40, 45, 50, 55, 60, 65, 70, 75, 80, 85, 90, 95, 100, 200, 300, 400, 500, 600, 700, 800, 900, or 1000 times higher than a corresponding ligase without the one or more non-standard amino acids in a buffer with the same redox potential. For example, a ligase provided herein comprising one or more non-standard amino acids, such as one or more selenocysteine residues, can ligate two or more nucleic acids together in a buffer with a redox potential of less than about −160 mV, less than about −170 mV, less than about −180 mV, less than about −190 mV, less than about −200 mV, less than about −210 mV, less than about −220 mV, less than about −230 mV, less than about −240 mV, or less than about −250 mV, less than about −260 mV, less than about −270 mV, less than about −280 mV, less than about −290 mV, less than about −300 mV, less than about −310 mV, less than about −320 mV, less than about −330 mV, less than about −340 mV, or less than about −350 mV, less than about −360 mV, less than about −370 mV, less than about −380 mV, less than about −390 mV, less than about −400 mV, less than about −410 mV, less than about −420 mV, less than about −430 mV, less than about −440 mV, or less than about −450 mV, less than about −460 mV, less than about −470 mV, less than about −480 mV, less than about −490 mV, less than about −500 mV, less than about −510 mV, less than about −520 mV, less than about −530 mV, less than about −540 mV, or less than about −550 mV, less than about −560 mV, less than about −570 mV, less than about −580 mV, less than about −590 mV, or less than about −600 mV, with an activity that is at least 1.1, 1.2, 1.3, 1.4, 1.5, 1.6, 1.7, 1.8, 1.9, 2, 2.1, 2.2, 2.3, 2.4, 2.5, 3, 3.5, 4, 4.5, 5, 5.5, 6, 6.5, 7, 7.5, 8, 8.5, 9, 9.5, 10, 10.5, 11, 12, 13, 14, 15, 16, 17, 18, 19, 20, 25, 30, 35, 40, 45, 50, 55, 60, 65, 70, 75, 80, 85, 90, 95, 100, 200, 300, 400, 500, 600, 700, 800, 900, or 1000 times higher than a corresponding ligase without the one or more non-standard amino acids in a buffer with the same redox potential.

In some embodiments, a restriction endonuclease may be made and used according to the invention with diselenide bonds between two selenocysteine residues. In some embodiments, a restriction endonuclease can comprise one or more non-standard amino acids. In some embodiments, a restriction endonuclease can comprise one or more selenocysteine residues. In some embodiments, a restriction endonuclease can comprise a diselenide bond between two selenocysteine residues. The diselenide bonds may be intramolecular or intermolecular. In some embodiments, a restriction endonuclease can comprise one or more diselenide bonds. In some embodiments, a restriction endonuclease comprising one or more non-standard amino acids has enzymatic activity in harsh conditions, such as reducing buffers or lysis buffers, that is higher than a corresponding restriction endonuclease without the non-standard amino acids under the same conditions.

For example, a restriction endonuclease provided herein comprising one or more non-standard amino acids, such as one or more selenocysteine residues, can cleave one or more bonds of a polynucleotide substrate with an activity that is at least 1.1, 1.2, 1.3, 1.4, 1.5, 1.6, 1.7, 1.8, 1.9, 2, 2.1, 2.2, 2.3, 2.4, 2.5, 3, 3.5, 4, 4.5, 5, 5.5, 6, 6.5, 7, 7.5, 8, 8.5, 9, 9.5, 10, 10.5, 11, 12, 13, 14, 15, 16, 17, 18, 19, 20, 25, 30, 35, 40, 45, 50, 55, 60, 65, 70, 75, 80, 85, 90, 95, 100, 200, 300, 400, 500, 600, 700, 800, 900, or 1000 times higher than a corresponding restriction endonuclease without the one or more non-standard amino acids.

For example, a restriction endonuclease provided herein comprising one or more non-standard amino acids, such as one or more selenocysteine residues, can cleave one or more bonds of a polynucleotide substrate in a buffer with an activity that is at least 1.1, 1.2, 1.3, 1.4, 1.5, 1.6, 1.7, 1.8, 1.9, 2, 2.1, 2.2, 2.3, 2.4, 2.5, 3, 3.5, 4, 4.5, 5, 5.5, 6, 6.5, 7, 7.5, 8, 8.5, 9, 9.5, 10, 10.5, 11, 12, 13, 14, 15, 16, 17, 18, 19, 20, 25, 30, 35, 40, 45, 50, 55, 60, 65, 70, 75, 80, 85, 90, 95, 100, 200, 300, 400, 500, 600, 700, 800, 900, or 1000 times higher than a corresponding restriction endonuclease without the one or more non-standard amino acids in the same buffer.

For example, a restriction endonuclease provided herein comprising one or more non-standard amino acids, such as one or more selenocysteine residues, can cleave one or more bonds of a polynucleotide substrate in a buffer comprising a detergent, a reducing reagent, and/or a reducing enzyme (e.g., a reductase) with an activity that is at least 1.1, 1.2, 1.3, 1.4, 1.5, 1.6, 1.7, 1.8, 1.9, 2, 2.1, 2.2, 2.3, 2.4, 2.5, 3, 3.5, 4, 4.5, 5, 5.5, 6, 6.5, 7, 7.5, 8, 8.5, 9, 9.5, 10, 10.5, 11, 12, 13, 14, 15, 16, 17, 18, 19, 20, 25, 30, 35, 40, 45, 50, 55, 60, 65, 70, 75, 80, 85, 90, 95, 100, 200, 300, 400, 500, 600, 700, 800, 900, or 1000 times higher than a corresponding restriction endonuclease without the one or more non-standard amino acids in the same buffer comprising the detergent, the reducing reagent, and/or the reducing enzyme (e.g., a reductase).

For example, a restriction endonuclease provided herein comprising one or more non-standard amino acids, such as one or more selenocysteine residues, can cleave one or more bonds of a polynucleotide substrate in a buffer with a redox potential of less than about −150 mV, with an activity that is at least 1.1, 1.2, 1.3, 1.4, 1.5, 1.6, 1.7, 1.8, 1.9, 2, 2.1, 2.2, 2.3, 2.4, 2.5, 3, 3.5, 4, 4.5, 5, 5.5, 6, 6.5, 7, 7.5, 8, 8.5, 9, 9.5, 10, 10.5, 11, 12, 13, 14, 15, 16, 17, 18, 19, 20, 25, 30, 35, 40, 45, 50, 55, 60, 65, 70, 75, 80, 85, 90, 95, 100, 200, 300, 400, 500, 600, 700, 800, 900, or 1000 times higher than a corresponding restriction endonuclease without the one or more non-standard amino acids in a buffer with the same redox potential. For example, a restriction endonuclease provided herein comprising one or more non-standard amino acids, such as one or more selenocysteine residues, can cleave one or more bonds of a polynucleotide substrate in a buffer with a redox potential of less than about −160 mV, less than about −170 mV, less than about −180 mV, less than about −190 mV, less than about −200 mV, less than about −210 mV, less than about −220 mV, less than about −230 mV, less than about −240 mV, or less than about −250 mV, less than about −260 mV, less than about −270 mV, less than about −280 mV, less than about −290 mV, less than about −300 mV, less than about −310 mV, less than about −320 mV, less than about −330 mV, less than about −340 mV, or less than about −350 mV, less than about −360 mV, less than about −370 mV, less than about −380 mV, less than about −390 mV, less than about −400 mV, less than about −410 mV, less than about −420 mV, less than about −430 mV, less than about −440 mV, or less than about −450 mV, less than about −460 mV, less than about −470 mV, less than about −480 mV, less than about −490 mV, less than about −500 mV, less than about −510 mV, less than about −520 mV, less than about −530 mV, less than about −540 mV, or less than about −550 mV, less than about −560 mV, less than about −570 mV, less than about −580 mV, less than about −590 mV, or less than about −600 mV, with an activity that is at least 1.1, 1.2, 1.3, 1.4, 1.5, 1.6, 1.7, 1.8, 1.9, 2, 2.1, 2.2, 2.3, 2.4, 2.5, 3, 3.5, 4, 4.5, 5, 5.5, 6, 6.5, 7, 7.5, 8, 8.5, 9, 9.5, 10, 10.5, 11, 12, 13, 14, 15, 16, 17, 18, 19, 20, 25, 30, 35, 40, 45, 50, 55, 60, 65, 70, 75, 80, 85, 90, 95, 100, 200, 300, 400, 500, 600, 700, 800, 900, or 1000 times higher than a corresponding restriction endonuclease without the one or more non-standard amino acids in a buffer with the same redox potential.

In some embodiments, a reverse transcriptase may be made and used according to the invention with diselenide bonds between two selenocysteine residues. In some embodiments, a reverse transcriptase can comprise one or more non-standard amino acids. In some embodiments, a reverse transcriptase can comprise one or more selenocysteine residues. In some embodiments, a reverse transcriptase can comprise a diselenide bond between two selenocysteine residues. The diselenide bonds may be intramolecular or intermolecular. In some embodiments, a reverse transcriptase can comprise one or more diselenide bonds. In some embodiments, a reverse transcriptase comprising one or more non-standard amino acids has enzymatic activity in harsh conditions, such as reducing buffers or lysis buffers, that is higher than a corresponding reverse transcriptase without the non-standard amino acids under the same conditions.

For example, a reverse transcriptase provided herein comprising one or more non-standard amino acids, such as one or more selenocysteine residues, can synthesize a cDNA from an RNA with an activity that is at least 1.1, 1.2, 1.3, 1.4, 1.5, 1.6, 1.7, 1.8, 1.9, 2, 2.1, 2.2, 2.3, 2.4, 2.5, 3, 3.5, 4, 4.5, 5, 5.5, 6, 6.5, 7, 7.5, 8, 8.5, 9, 9.5, 10, 10.5, 11, 12, 13, 14, 15, 16, 17, 18, 19, 20, 25, 30, 35, 40, 45, 50, 55, 60, 65, 70, 75, 80, 85, 90, 95, 100, 200, 300, 400, 500, 600, 700, 800, 900, or 1000 times higher than a corresponding reverse transcriptase without the one or more non-standard amino acids.

For example, a reverse transcriptase provided herein comprising one or more non-standard amino acids, such as one or more selenocysteine residues, can synthesize a cDNA from an RNA in a buffer with an activity that is at least 1.1, 1.2, 1.3, 1.4, 1.5, 1.6, 1.7, 1.8, 1.9, 2, 2.1, 2.2, 2.3, 2.4, 2.5, 3, 3.5, 4, 4.5, 5, 5.5, 6, 6.5, 7, 7.5, 8, 8.5, 9, 9.5, 10, 10.5, 11, 12, 13, 14, 15, 16, 17, 18, 19, 20, 25, 30, 35, 40, 45, 50, 55, 60, 65, 70, 75, 80, 85, 90, 95, 100, 200, 300, 400, 500, 600, 700, 800, 900, or 1000 times higher than a corresponding reverse transcriptase without the one or more non-standard amino acids in the same buffer.

For example, a reverse transcriptase provided herein comprising one or more non-standard amino acids, such as one or more selenocysteine residues, can synthesize a cDNA from an RNA in a buffer comprising a detergent, a reducing reagent, and/or a reducing enzyme (e.g., a reductase) with an activity that is at least 1.1, 1.2, 1.3, 1.4, 1.5, 1.6, 1.7, 1.8, 1.9, 2, 2.1, 2.2, 2.3, 2.4, 2.5, 3, 3.5, 4, 4.5, 5, 5.5, 6, 6.5, 7, 7.5, 8, 8.5, 9, 9.5, 10, 10.5, 11, 12, 13, 14, 15, 16, 17, 18, 19, 20, 25, 30, 35, 40, 45, 50, 55, 60, 65, 70, 75, 80, 85, 90, 95, 100, 200, 300, 400, 500, 600, 700, 800, 900, or 1000 times higher than a corresponding reverse transcriptase without the one or more non-standard amino acids in the same buffer comprising the detergent, the reducing reagent, and/or the reducing enzyme (e.g., a reductase).

For example, a reverse transcriptase provided herein comprising one or more non-standard amino acids, such as one or more selenocysteine residues, can synthesize a cDNA from an RNA in a buffer with a redox potential of less than about −150 mV, with an activity that is at least 1.1, 1.2, 1.3, 1.4, 1.5, 1.6, 1.7, 1.8, 1.9, 2, 2.1, 2.2, 2.3, 2.4, 2.5, 3, 3.5, 4, 4.5, 5, 5.5, 6, 6.5, 7, 7.5, 8, 8.5, 9, 9.5, 10, 10.5, 11, 12, 13, 14, 15, 16, 17, 18, 19, 20, 25, 30, 35, 40, 45, 50, 55, 60, 65, 70, 75, 80, 85, 90, 95, 100, 200, 300, 400, 500, 600, 700, 800, 900, or 1000 times higher than a corresponding reverse transcriptase without the one or more non-standard amino acids in a buffer with the same redox potential. For example, a reverse transcriptase provided herein comprising one or more non-standard amino acids, such as one or more selenocysteine residues, can synthesize a cDNA from an RNA in a buffer with a redox potential of less than about −160 mV, less than about −170 mV, less than about −180 mV, less than about −190 mV, less than about −200 mV, less than about −210 mV, less than about −220 mV, less than about −230 mV, less than about −240 mV, or less than about −250 mV, less than about −260 mV, less than about −270 mV, less than about −280 mV, less than about −290 mV, less than about −300 mV, less than about −310 mV, less than about −320 mV, less than about −330 mV, less than about −340 mV, or less than about −350 mV, less than about −360 mV, less than about −370 mV, less than about −380 mV, less than about −390 mV, less than about −400 mV, less than about −410 mV, less than about −420 mV, less than about −430 mV, less than about −440 mV, or less than about −450 mV, less than about −460 mV, less than about −470 mV, less than about −480 mV, less than about −490 mV, less than about −500 mV, less than about −510 mV, less than about −520 mV, less than about −530 mV, less than about −540 mV, or less than about −550 mV, less than about −560 mV, less than about −570 mV, less than about −580 mV, less than about −590 mV, or less than about −600 mV, with an activity that is at least 1.1, 1.2, 1.3, 1.4, 1.5, 1.6, 1.7, 1.8, 1.9, 2, 2.1, 2.2, 2.3, 2.4, 2.5, 3, 3.5, 4, 4.5, 5, 5.5, 6, 6.5, 7, 7.5, 8, 8.5, 9, 9.5, 10, 10.5, 11, 12, 13, 14, 15, 16, 17, 18, 19, 20, 25, 30, 35, 40, 45, 50, 55, 60, 65, 70, 75, 80, 85, 90, 95, 100, 200, 300, 400, 500, 600, 700, 800, 900, or 1000 times higher than a corresponding reverse transcriptase without the one or more non-standard amino acids in a buffer with the same redox potential.

In some embodiments, a protease may be made and used according to the invention with diselenide bonds between two selenocysteine residues. In some embodiments, a protease can comprise one or more non-standard amino acids. In some embodiments, a protease can comprise one or more selenocysteine residues. In some embodiments, a protease can comprise a diselenide bond between two selenocysteine residues. The diselenide bonds may be intramolecular or intermolecular. In some embodiments, a protease can comprise one or more diselenide bonds. In some embodiments, a protease comprising one or more non-standard amino acids has enzymatic activity in harsh conditions, such as reducing buffers or lysis buffers, that is higher than a corresponding protease without the non-standard amino acids under the same conditions.

For example, a protease provided herein comprising one or more non-standard amino acids, such as one or more selenocysteine residues, can cleave a bond of a polypeptide substrate with an activity that is at least 1.1, 1.2, 1.3, 1.4, 1.5, 1.6, 1.7, 1.8, 1.9, 2, 2.1, 2.2, 2.3, 2.4, 2.5, 3, 3.5, 4, 4.5, 5, 5.5, 6, 6.5, 7, 7.5, 8, 8.5, 9, 9.5, 10, 10.5, 11, 12, 13, 14, 15, 16, 17, 18, 19, 20, 25, 30, 35, 40, 45, 50, 55, 60, 65, 70, 75, 80, 85, 90, 95, 100, 200, 300, 400, 500, 600, 700, 800, 900, or 1000 times higher than a corresponding protease without the one or more non-standard amino acids.

For example, a protease provided herein comprising one or more non-standard amino acids, such as one or more selenocysteine residues, can cleave a bond of a polypeptide substrate in a buffer with an activity that is at least 1.1, 1.2, 1.3, 1.4, 1.5, 1.6, 1.7, 1.8, 1.9, 2, 2.1, 2.2, 2.3, 2.4, 2.5, 3, 3.5, 4, 4.5, 5, 5.5, 6, 6.5, 7, 7.5, 8, 8.5, 9, 9.5, 10, 10.5, 11, 12, 13, 14, 15, 16, 17, 18, 19, 20, 25, 30, 35, 40, 45, 50, 55, 60, 65, 70, 75, 80, 85, 90, 95, 100, 200, 300, 400, 500, 600, 700, 800, 900, or 1000 times higher than a corresponding protease without the one or more non-standard amino acids in the same buffer.

For example, a protease provided herein comprising one or more non-standard amino acids, such as one or more selenocysteine residues, can cleave a bond of a polypeptide substrate in a buffer comprising a detergent, a reducing reagent, and/or a reducing enzyme (e.g., a reductase) with an activity that is at least 1.1, 1.2, 1.3, 1.4, 1.5, 1.6, 1.7, 1.8, 1.9, 2, 2.1, 2.2, 2.3, 2.4, 2.5, 3, 3.5, 4, 4.5, 5, 5.5, 6, 6.5, 7, 7.5, 8, 8.5, 9, 9.5, 10, 10.5, 11, 12, 13, 14, 15, 16, 17, 18, 19, 20, 25, 30, 35, 40, 45, 50, 55, 60, 65, 70, 75, 80, 85, 90, 95, 100, 200, 300, 400, 500, 600, 700, 800, 900, or 1000 times higher than a corresponding protease without the one or more non-standard amino acids in the same buffer comprising the detergent, the reducing reagent, and/or the reducing enzyme (e.g., a reductase).

For example, a protease provided herein comprising one or more non-standard amino acids, such as one or more selenocysteine residues, can cleave a bond of a polypeptide substrate in a buffer with a redox potential of less than about −150 mV, with an activity that is at least 1.1, 1.2, 1.3, 1.4, 1.5, 1.6, 1.7, 1.8, 1.9, 2, 2.1, 2.2, 2.3, 2.4, 2.5, 3, 3.5, 4, 4.5, 5, 5.5, 6, 6.5, 7, 7.5, 8, 8.5, 9, 9.5, 10, 10.5, 11, 12, 13, 14, 15, 16, 17, 18, 19, 20, 25, 30, 35, 40, 45, 50, 55, 60, 65, 70, 75, 80, 85, 90, 95, 100, 200, 300, 400, 500, 600, 700, 800, 900, or 1000 times higher than a corresponding protease without the one or more non-standard amino acids in a buffer with the same redox potential. For example, a protease provided herein comprising one or more non-standard amino acids, such as one or more selenocysteine residues, can cleave a bond of a polypeptide substrate in a buffer with a redox potential of less than about −160 mV, less than about −170 mV, less than about −180 mV, less than about −190 mV, less than about −200 mV, less than about −210 mV, less than about −220 mV, less than about −230 mV, less than about −240 mV, or less than about −250 mV, less than about −260 mV, less than about −270 mV, less than about −280 mV, less than about −290 mV, less than about −300 mV, less than about −310 mV, less than about −320 mV, less than about −330 mV, less than about −340 mV, or less than about −350 mV, less than about −360 mV, less than about −370 mV, less than about −380 mV, less than about −390 mV, less than about −400 mV, less than about −410 mV, less than about −420 mV, less than about −430 mV, less than about −440 mV, or less than about −450 mV, less than about −460 mV, less than about −470 mV, less than about −480 mV, less than about −490 mV, less than about −500 mV, less than about −510 mV, less than about −520 mV, less than about −530 mV, less than about −540 mV, or less than about −550 mV, less than about −560 mV, less than about −570 mV, less than about −580 mV, less than about −590 mV, or less than about −600 mV, with an activity that is at least 1.1, 1.2, 1.3, 1.4, 1.5, 1.6, 1.7, 1.8, 1.9, 2, 2.1, 2.2, 2.3, 2.4, 2.5, 3, 3.5, 4, 4.5, 5, 5.5, 6, 6.5, 7, 7.5, 8, 8.5, 9, 9.5, 10, 10.5, 11, 12, 13, 14, 15, 16, 17, 18, 19, 20, 25, 30, 35, 40, 45, 50, 55, 60, 65, 70, 75, 80, 85, 90, 95, 100, 200, 300, 400, 500, 600, 700, 800, 900, or 1000 times higher than a corresponding protease without the one or more non-standard amino acids in a buffer with the same redox potential.

In some embodiments, an enzyme containing one or more catalytic cysteine residues (i.e. a cysteine involved in a catalysis reaction, e.g., an active site cysteine) may be made and used according to the invention with one or more selenocysteine residue substitutions for these one or more catalytic cysteine residues. The one or more selenocysteine substitutions can increase or alter the enzyme activity in the reaction environment.

In some embodiments, a carbon capturing enzyme (e.g., a carbon fixing enzyme) may be made and used according to the invention with diselenide bonds between two selenocysteine residues. In some embodiments, a carbon capturing enzyme (e.g., a carbon fixing enzyme) can comprise one or more non-standard amino acids. In some embodiments, a carbon capturing enzyme (e.g., a carbon fixing enzyme) can comprise one or more selenocysteine residues. In some embodiments, a carbon capturing enzyme (e.g., a carbon fixing enzyme) can comprise a diselenide bond between two selenocysteine residues. The diselenide bonds may be intra-molecular or intermolecular. In some embodiments, a carbon capturing enzyme (e.g., a carbon fixing enzyme) can comprise one or more diselenide bonds. In some embodiments, a carbon capturing enzyme (e.g., a carbon fixing enzyme) comprising one or more non-standard amino acids has enzymatic activity in harsh conditions, such as reducing buffers or lysis buffers, that is higher than a corresponding carbon capturing enzyme (e.g., a carbon fixing enzyme) without the non-standard amino acids under the same conditions. For example, in some embodiments, a carbon capturing enzyme (e.g., a carbon fixing enzyme), such as an anhydrase enzyme (e.g., β-carbonic anhydrase) can comprise one or more catalytic selenocysteine substitutions.

For example, a carbon capturing enzyme (e.g., a carbon fixing enzyme) provided herein comprising one or more non-standard amino acids, such as one or more selenocysteine residues, can capture or fix carbon with an activity that is at least 1.1, 1.2, 1.3, 1.4, 1.5, 1.6, 1.7, 1.8, 1.9, 2, 2.1, 2.2, 2.3, 2.4, 2.5, 3, 3.5, 4, 4.5, 5, 5.5, 6, 6.5, 7, 7.5, 8, 8.5, 9, 9.5, 10, 10.5, 11, 12, 13, 14, 15, 16, 17, 18, 19, 20, 25, 30, 35, 40, 45, 50, 55, 60, 65, 70, 75, 80, 85, 90, 95, 100, 200, 300, 400, 500, 600, 700, 800, 900, or 1000 times higher than a corresponding carbon capturing enzyme (e.g., a carbon fixing enzyme) without the one or more non-standard amino acids. For example, an enzyme, such as a carbon capturing enzyme (e.g., a carbon fixing enzyme) provided herein comprising one or more non-standard active site amino acids, such as one or more active site selenocysteine residues can capture or fix carbon with an activity that is at least 1.1, 1.2, 1.3, 1.4, 1.5, 1.6, 1.7, 1.8, 1.9, 2, 2.1, 2.2, 2.3, 2.4, 2.5, 3, 3.5, 4, 4.5, 5, 5.5, 6, 6.5, 7, 7.5, 8, 8.5, 9, 9.5, 10, 10.5, 11, 12, 13, 14, 15, 16, 17, 18, 19, 20, 25, 30, 35, 40, 45, 50, 55, 60, 65, 70, 75, 80, 85, 90, 95, 100, 200, 300, 400, 500, 600, 700, 800, 900, or 1000 times higher than a corresponding enzyme, such as a carbon capturing enzyme (e.g., a carbon fixing enzyme) without the one or more non-standard active site amino acids.

For example, a carbon capturing enzyme (e.g., a carbon fixing enzyme) provided herein comprising one or more non-standard amino acids, such as one or more selenocysteine residues, can capture or fix carbon in a buffer or environment with an activity that is at least 1.1, 1.2, 1.3, 1.4, 1.5, 1.6, 1.7, 1.8, 1.9, 2, 2.1, 2.2, 2.3, 2.4, 2.5, 3, 3.5, 4, 4.5, 5, 5.5, 6, 6.5, 7, 7.5, 8, 8.5, 9, 9.5, 10, 10.5, 11, 12, 13, 14, 15, 16, 17, 18, 19, 20, 25, 30, 35, 40, 45, 50, 55, 60, 65, 70, 75, 80, 85, 90, 95, 100, 200, 300, 400, 500, 600, 700, 800, 900, or 1000 times higher than a corresponding carbon capturing enzyme (e.g., a carbon fixing enzyme) without the one or more non-standard amino acids in the same buffer or environment.

For example, a carbon capturing enzyme (e.g., a carbon fixing enzyme) provided herein comprising one or more non-standard amino acids, such as one or more selenocysteine residues, can capture or fix carbon in a buffer comprising a detergent, a reducing reagent, and/or a reducing enzyme (e.g., a reductase) or a reducing environment with an activity that is at least 1.1, 1.2, 1.3, 1.4, 1.5, 1.6, 1.7, 1.8, 1.9, 2, 2.1, 2.2, 2.3, 2.4, 2.5, 3, 3.5, 4, 4.5, 5, 5.5, 6, 6.5, 7, 7.5, 8, 8.5, 9, 9.5, 10, 10.5, 11, 12, 13, 14, 15, 16, 17, 18, 19, 20, 25, 30, 35, 40, 45, 50, 55, 60, 65, 70, 75, 80, 85, 90, 95, 100, 200, 300, 400, 500, 600, 700, 800, 900, or 1000 times higher than a corresponding carbon capturing enzyme (e.g., a carbon fixing enzyme) without the one or more non-standard amino acids in the same buffer comprising the detergent, the reducing reagent, and/or the reducing enzyme (e.g., a reductase) or in the same reducing environment.

For example, a carbon capturing enzyme (e.g., a carbon fixing enzyme) provided herein comprising one or more non-standard amino acids, such as one or more selenocysteine residues, can capture or fix carbon in a buffer or environment with a redox potential of less than about −150 mV, with an activity that is at least 1.1, 1.2, 1.3, 1.4, 1.5, 1.6, 1.7, 1.8, 1.9, 2, 2.1, 2.2, 2.3, 2.4, 2.5, 3, 3.5, 4, 4.5, 5, 5.5, 6, 6.5, 7, 7.5, 8, 8.5, 9, 9.5, 10, 10.5, 11, 12, 13, 14, 15, 16, 17, 18, 19, 20, 25, 30, 35, 40, 45, 50, 55, 60, 65, 70, 75, 80, 85, 90, 95, 100, 200, 300, 400, 500, 600, 700, 800, 900, or 1000 times higher than a corresponding carbon capturing enzyme (e.g., a carbon fixing enzyme) without the one or more non-standard amino acids in a buffer or environment with the same redox potential. For example, a carbon capturing enzyme (e.g., a carbon fixing enzyme) provided herein comprising one or more non-standard amino acids, such as one or more selenocysteine residues, can capture or fix carbon in a buffer or environment with a redox potential of less than about −160 mV, less than about −170 mV, less than about −180 mV, less than about −190 mV, less than about −200 mV, less than about −210 mV, less than about −220 mV, less than about −230 mV, less than about −240 mV, or less than about −250 mV, less than about −260 mV, less than about −270 mV, less than about −280 mV, less than about −290 mV, less than about −300 mV, less than about −310 mV, less than about −320 mV, less than about −330 mV, less than about −340 mV, or less than about −350 mV, less than about −360 mV, less than about −370 mV, less than about −380 mV, less than about −390 mV, less than about −400 mV, less than about −410 mV, less than about −420 mV, less than about −430 mV, less than about −440 mV, or less than about −450 mV, less than about −460 mV, less than about −470 mV, less than about −480 mV, less than about −490 mV, less than about −500 mV, less than about −510 mV, less than about −520 mV, less than about −530 mV, less than about −540 mV, or less than about −550 mV, less than about −560 mV, less than about −570 mV, less than about −580 mV, less than about −590 mV, or less than about −600 mV, with an activity that is at least 1.1, 1.2, 1.3, 1.4, 1.5, 1.6, 1.7, 1.8, 1.9, 2, 2.1, 2.2, 2.3, 2.4, 2.5, 3, 3.5, 4, 4.5, 5, 5.5, 6, 6.5, 7, 7.5, 8, 8.5, 9, 9.5, 10, 10.5, 11, 12, 13, 14, 15, 16, 17, 18, 19, 20, 25, 30, 35, 40, 45, 50, 55, 60, 65, 70, 75, 80, 85, 90, 95, 100, 200, 300, 400, 500, 600, 700, 800, 900, or 1000 times higher than a corresponding carbon capturing enzyme (e.g., a carbon fixing enzyme) without the one or more non-standard amino acids in a buffer or environment with the same redox potential.

In some aspects, provided herein is a composition comprising a stabilized deoxyribonuclease I (DNase I) polypeptide comprising one or more non-standard amino acids, a functional fragment thereof, or a variant thereof. In some embodiments, the stabilized DNase I polypeptide may be made and used according to the invention with diselenide bonds between two selenocysteine residues. In some embodiments, the stabilized DNase I polypeptide can comprise one or more non-standard amino acids. In some embodiments, the stabilized DNase I polypeptide can comprise one or more selenocysteine residues. In some embodiments, the stabilized DNase I polypeptide can comprise a diselenide bond between two selenocysteine residues. The diselenide bonds may be intramolecular or intermolecular. In some embodiments, the stabilized DNase I polypeptide can comprise one or more diselenide bonds. In some embodiments, the stabilized DNase I polypeptide can comprise one or more catalytic selenocysteine substitutions.

In some aspects, provided herein is a composition comprising a stabilized deoxyribonuclease I (DNase I) polypeptide comprising one or more non-standard amino acids, a functional fragment thereof, or a variant thereof, wherein the stabilized DNase I polypeptide has a higher endonuclease activity for a DNA substrate in an environment than an endonuclease activity for the DNA substrate of a corresponding DNase I polypeptide, functional fragment thereof, or variant thereof that does not comprise the one or more non-standard amino acids. For example, the stabilized DNase I polypeptide can have at least 1.1, 1.2, 1.3, 1.4, 1.5, 1.6, 1.7, 1.8, 1.9, 2, 2.1, 2.2, 2.3, 2.4, 2.5, 3, 3.5, 4, 4.5, 5, 5.5, 6, 6.5, 7, 7.5, 8, 8.5, 9, 9.5, 10, 10.5, 11, 12, 13, 14, 15, 16, 17, 18, 19, 20, 25, 30, 35, 40, 45, 50, 55, 60, 65, 70, 75, 80, 85, 90, 95, 100, 200, 300, 400, 500, 600, 700, 800, 900, or 1000 or greater fold higher endonuclease activity for a DNA substrate in an environment than an endonuclease activity for the DNA substrate of a corresponding DNase I polypeptide, functional fragment thereof, or variant thereof that does not comprise the one or more non-standard amino acids.

In some aspects, provided herein is a composition comprising a stabilized deoxyribonuclease I (DNase I) polypeptide comprising one or more non-standard amino acids, a functional fragment thereof, or a variant thereof, wherein the stabilized DNase I polypeptide does not destabilize in an environment that a corresponding DNase I polypeptide, functional fragment thereof, or variant thereof that does not comprise the one or more non-standard amino acids does destabilize. The destabilization can be obtained by contacting the corresponding DNase I polypeptide with one or more destabilization agents. The destabilization can be obtained by placing the corresponding DNase I polypeptide in a destabilization environment. The environment to destabilize the corresponding DNase I polypeptide is described elsewhere herein.

In some aspects, provided herein is a composition comprising a stabilized deoxyribonuclease I (DNase I) polypeptide comprising one or more non-standard amino acids, a functional fragment thereof, or a variant thereof, wherein the stabilized DNase I polypeptide has a melting temperature ($T_m$) that is at least 5° C. higher than a $T_m$ of a corresponding DNase I polypeptide, functional fragment thereof, or variant thereof that does not comprise the one or more non-standard amino acids.

In some embodiments, the composition can comprise a stabilized deoxyribonuclease I (DNase I) polypeptide comprising one or more non-standard amino acids, a functional fragment thereof, or a variant thereof, wherein the stabilized DNase I polypeptide can have a melting temperature ($T_m$) that can be at least 1° C., 2° C., 3° C., 4° C., 5° C., 6° C., 7° C., 8° C., 9° C., 10° C., 11° C., 12° C., 13° C., 14° C., 15° C., 16° C., 17° C., 18° C., 19° C., 20° C., 21° C., 22° C., 23° C., 24° C., 25° C., 26° C., 27° C., 28° C., 29° C., 30° C., 31° C., 32° C., 33° C., 34° C., 35° C. or 36° C. higher than a $T_m$ of a corresponding DNase I polypeptide, functional fragment thereof, or variant thereof that does not comprise the one or more non-standard amino acids. In some embodiments, the composition can comprise a stabilized deoxyribonuclease I (DNase I) polypeptide comprising one or more non-standard amino acids, a functional fragment thereof, or a variant thereof, wherein the stabilized DNase I polypeptide can have a melting temperature ($T_m$) that can be less than 1° C. higher than a $T_m$ of a corresponding DNase I polypeptide, functional fragment thereof, or variant thereof that does not comprise the one or more non-standard amino acids.

In some embodiments, at least one, two, three, four or more of the one or more non-standard amino acids is selenocysteine. In some embodiments, at least two of the one or more non-standard amino acids are directly linked by a bond.

In some embodiments, at least four of the one or more non-standard amino acids can be directly linked by a bond, wherein a first pair of the at least four of the one or more non-standard amino acids can be directly linked by a bond, and a second pair of at the least four of the one or more non-standard amino acids can be directly linked by a bond. In some embodiments, the bond is a diselenide bond. In some embodiments, the diselenide bond can be an intermolecular or an intramolecular bond.

In some embodiments, the stabilized DNase I polypeptide, functional fragment thereof, or variant thereof, can have a half-life that can be at least a 1.1 fold higher than a half-life of a corresponding DNase I polypeptide, functional fragment thereof, or variant thereof that does not comprise the one or more non-standard amino acid. In some embodiments, the stabilized DNase I polypeptide, functional fragment thereof, or variant thereof, can have a half-life that can be at least a 1.1, 1.2, 1.3, 1.4, 1.5, 1.6, 1.7, 1.8, 1.9, 2, 2.1, 2.2, 2.3, 2.4, 2.5, 3, 3.5, 4, 4.5, 5, 5.5, 6, 6.5, 7, 7.5, 8, 8.5, 9, 9.5, 10, 10.5, 11, 12, 13, 14, 15, 16, 17, 18, 19, 20, 25, 30, 35, 40, 45, 50, 55, 60, 65, 70, 75, 80, 85, 90, 95, 100, 200, 300, 400, 500, 600, 700, 800, 900, or 1000 or greater fold higher than a half-life of a corresponding DNase I polypeptide, functional fragment thereof, or variant thereof that does not comprise the one or more non-standard amino acid. In some embodiments, the stabilized DNase I polypeptide, functional fragment thereof, or variant thereof, can have a half-life that can be less than 1.1 fold higher than a half-life of a corresponding DNase I polypeptide, functional fragment thereof, or variant thereof that does not comprise the one or more non-standard amino acid.

In some embodiments, the stabilized DNase I polypeptide, functional fragment thereof, or variant thereof, can have at least 70%, 75%, 80%, 85%, 90%, 95% sequence identity to SEQ ID NO:1. In some embodiments, the stabilized DNase I polypeptide, functional fragment thereof, or variant thereof, can have at least 10%, 20%, 30%, 40%, 50%, 60%, 70%, 75%, 80%, 85%, 90%, 95% or greater sequence identity to SEQ ID NO:1. In some embodiments, the stabilized DNase I polypeptide, functional fragment thereof, or variant thereof, can have less than 10% sequence identity to SEQ ID NO:1.

In some embodiments, the stabilized DNase I polypeptide, functional fragment thereof, or variant thereof, can comprise a sequence with at least 70%, 75%, 80%, 85%, 90%, 95% sequence identity to at least 25, 50, 75, 100, 125, 150, 175, 200, 225, 250, or 261 contiguous amino acids of SEQ ID NO: 1. In some embodiments, the stabilized DNase I polypeptide, functional fragment thereof, or variant thereof, can comprise a sequence with at least 10%, 20%, 30%, 40%, 50%, 60%, 70%, 75%, 80%, 85%, 90%, 95% or greater sequence identity to at least 25, 50, 75, 100, 125, 150, 175, 200, 225, 250, or 261 contiguous amino acids of SEQ ID NO: 1. In some embodiments, the stabilized DNase I polypeptide, functional fragment thereof, or variant thereof, can comprise a sequence with less than 10% sequence identity to at least 25, 50, 75, 100, 125, 150, 175, 200, 225, 250, or 261 contiguous amino acids of SEQ ID NO: 1.

In some embodiments, the DNase I comprises an amino acid sequence with at least 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to at least 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 260, or 261 contiguous amino acids of (SEQ ID NO: 1)
ALKIAAFNIRTFGETKMSNATLASYIVRIVRRYDIVLIQEVRDSHLVAVG

KLLDYLNQDDPNTYHYVVSEPLGRNSYKERYLFLFRPNKVSVLDTYQYDD

GUESUGNDSFSREPAVVKFSSHSTKVKEFAIVALHSAPSDAVAEINSLYD

VYLDVQQKWHLNDVMLMGDFNADUSYVTSSQWSSIRLRTSSTFQWLIPDS

ADTTATSTNUAYDRIVVAGSLLQSSVVPGSAAPFDFQAAYGLSNEMALAI

SDHYPVEVTLT, where U is a non-standard amino acid such as selenocysteine.

In some embodiments, the DNase I comprises an amino acid sequence with at least 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to at least (SEQ ID NO: 1)
ALKIAAFNIRTFGETKMSNATLASYIVRIVRRYDIVLIQEVRDSHLVAVG

KLLDYLNQDDPNTYHYVVSEPLGRNSYKERYLFLFRPNKVSVLDTYQYDD

GUESUGNDSFSREPAVVKFSSHSTKVKEFAIVALHSAPSDAVAEINSLYD

VYLDVQQKWHLNDVMLMGDFNADUSYVTSSQWSSIRLRTSSTFQWLIPDS

-continued
ADTTATSTNUAYDRIVVAGSLLQSSVVPGSAAPFDFQAAYGLSNEMALAI

SDHYPVEVTLT, where U is a non-standard amino acid such as selenocysteine.

In some embodiments, the DNase I comprises an amino acid sequence with at least 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to (SEQ ID NO: 2)
RGTRLMGLLLALAGLLQLGLSLKIAAFNIRTFGETKMSNATLASYIVRIV

RRYDIVLIQEVRDSHLVAVGKLLDYLNQDDPNTYHYVVSEPLGRNSYKER

YLFLFRPNKVSVLDTYQYDDGCESCGNDSFSREPAVVKFSSHSTKVKEFA

IVALHSAPSDAVAEINSLYDVYLDVQQKWHLNDVMLMGDFNADCSYVTSS

QWSSIRLRTSSTFQWLIPDSADTTATSTNCAYDRIVVAGSLLQSSVVPGS

AAPFDFQAAYGLSNEMALAISDHYPVEVTLT.

where U is a non-standard amino acid such as selenocysteine

In some embodiments, the DNase I comprises an amino acid sequence with at least 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to at least 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 260, 261, 262, 263, 264, 265, 266, 267, 268, 269, 270, 271, 272, 273, 274, 275, 276, 277, 278, 279, 280 or 281 contiguous amino acids of (SEQ ID NO: 2)
RGTRLMGLLLALAGLLQLGLSLKIAAFNIRTFGETKMSNATLASYIVRIV

RRYDIVLIQEVRDSHLVAVGKLLDYLNQDDPNTYHYVVSEPLGRNSYKER

YLFLFRPNKVSVLDTYQYDDGCESCGNDSFSREPAVVKFSSHSTKVKEFA

IVALHSAPSDAVAEINSLYDVYLDVQQKWHLNDVMLMGDFNADCSYVTSS

QWSSIRLRTSSTFQWLIPDSADTTATSTNCAYDRIVVAGSLLQSSVVPGS

AAPFDFQAAYGLSNEMALAISDHYPVEVTLT, where U is a non-standard amino acid such as selenocysteine.

In some embodiments, the DNase I further comprises at least one affinity tag. In some embodiments, an affinity tag of a DNase I is a C-terminal affinity tag. In some embodiments, an affinity tag of a DNase I is an N-terminal affinity tag. In some embodiments, a first affinity tag of a DNase I is an N-terminal affinity tag and a second affinity tag of a DNase I is a C-terminal affinity tag. In some embodiments, a first affinity tag of a DNase I is a first N-terminal affinity tag and a second affinity tag of a DNase I is a second N-terminal affinity tag. In some embodiments, a first affinity tag of a DNase I is a first C-terminal affinity tag and a second affinity tag of a DNase I is a second C-terminal affinity tag.

For example, the DNase I can comprise a poly-histidine tag, poly-histidine-glycine tag, poly-arginine tag, poly-aspartate tag, poly-cysteine tag, poly-phenylalanine, c-myc tag, Herpes simplex virus glycoprotein D (gD) tag, FLAG tag, KT3 epitope tag, tubulin epitope tag, T7 gene 10 protein peptide tag, streptavidin tag, streptavidin binding peptide (SPB) tag, Strep-tag, Strep-tag II, albumin-binding protein (ABP) tag, alkaline phosphatase (AP) tag, bluetongue virus tag (B-tag), calmodulin binding peptide (CBP) tag, chloramphenicol acetyl transferase (CAT) tag, choline-binding domain (CBD) tag, chitin binding domain (CBD) tag, cellulose binding domain (CBP) tag, dihydrofolate reductase (DHFR) tag, galactose-binding protein (GBP) tag, maltose binding protein (MBP), glutathione-S-transferase (GST), Glu-Glu (EE) tag, human influenza hemagglutinin (HA) tag, horseradish peroxidase (HRP) tag, NE-tag, HSV tag, ketosteroid isomerase (KSI) tag, KT3 tag, LacZ tag, luciferase tag, NusA tag, PDZ domain tag, AviTag, Calmodulin-tag, E-tag, S-tag, SBP-tag, Softag 1, Softag 3, TC tag, VSV-tag, Xpress tag, Isopeptag, SpyTag, SnoopTag, Profinity eXact tag, Protein C tag, S1-tag, S-tag, biotin-carboxy carrier protein (BCCP) tag, green fluorescent protein (GFP) tag, small ubiquitin-like modifier (SUMO) tag, tandem affinity purification (TAP) tag, HaloTag, Nus-tag, Thioredoxin-tag, Fc-tag, CYD tag, HPC tag, TrpE tag, ubiquitin tag, VSV-G epitope tag, V5 tag, or a combination thereof.

In some embodiments, the DNase I further comprises at least two affinity tags. For example, the DNase I can comprise at least two affinity tags selected from a poly-histidine tag, poly-histidine-glycine tag, poly-arginine tag, poly-aspartate tag, poly-cysteine tag, poly-phenylalanine, c-myc tag, Herpes simplex virus glycoprotein D (gD) tag, FLAG tag, KT3 epitope tag, tubulin epitope tag, T7 gene 10 protein peptide tag, streptavidin tag, streptavidin binding peptide (SPB) tag, Strep-tag, Strep-tag II, albumin-binding protein (ABP) tag, alkaline phosphatase (AP) tag, bluetongue virus tag (B-tag), calmodulin binding peptide (CBP) tag, chloramphenicol acetyl transferase (CAT) tag, choline-binding domain (CBD) tag, chitin binding domain (CBD) tag, cellulose binding domain (CBP) tag, dihydrofolate reductase (DHFR) tag, galactose-binding protein (GBP) tag, maltose binding protein (MBP), glutathione-S-transferase (GST), Glu-Glu (EE) tag, human influenza hemagglutinin (HA) tag, horseradish peroxidase (HRP) tag, NE-tag, HSV tag, ketosteroid isomerase (KSI) tag, KT3 tag, LacZ tag, luciferase tag, NusA tag, PDZ domain tag, AviTag, Calmodulin-tag, E-tag, S-tag, SBP-tag, Softag 1, Softag 3, TC tag, VSV-tag, Xpress tag, Isopeptag, SpyTag, SnoopTag, Profinity eXact tag, Protein C tag, S1-tag, S-tag, biotin-carboxy carrier protein (BCCP) tag, green fluorescent protein (GFP) tag, small ubiquitin-like modifier (SUMO) tag, tandem affinity purification (TAP) tag, HaloTag, Nus-tag, Thioredoxin-tag, Fc-tag, CYD tag, HPC tag, TrpE tag, ubiquitin tag, VSV-G epitope tag, and V5 tag.

In some embodiments, the DNase I comprises an affinity tag that is GST. In some embodiments, the DNase I comprises an affinity tag that is a poly-histidine tag, such as a 6x-His tag. In some embodiments, the DNase I comprises an affinity tag that is MBP. In some embodiments, the DNase I comprises an affinity tag that is a strep-tag, such as two strep tags.

In some embodiments, the DNase I comprises a first affinity tag that is GST and a second affinity tag that is a poly-histidine tag, such as a 6x-His tag. In some embodiments, the DNase I comprises a first affinity tag that is GST and a second affinity tag that is a strep tag. In some embodiments, the DNase I comprises a first affinity tag that is a strep tag, such as two strep tags, and a second affinity tag that is a poly-histidine tag, such as a 6x-His tag. In some embodiments, the DNase I comprises a first affinity tag that is MBP and a second affinity tag that is a poly-histidine tag, such as a 6x-His tag. In some embodiments, the DNase I comprises a first affinity tag that is MBP and a second affinity tag that is a strep tag, such as two strep tags.

In some embodiments, the DNase I comprises a first affinity tag that is GST, a second affinity tag that is a poly-histidine tag, such as a 6x-His tag, and a third affinity tag that is a strep tag, such as two strep tags. In some embodiments, the DNase I comprises a GST tag, a His tag, and two strep tags. In some embodiments, the DNase I comprises a first affinity tag that is MBP, a second affinity tag that is a poly-histidine tag, such as a 6x-His tag, and a third affinity tag that is a strep tag, such as two strep tags. In some embodiments, the DNase I comprises a MBP tag, a His tag, and two strep tags.

In some embodiments, the DNase I comprises an amino acid sequence with at least 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to (SEQ ID NO: 3)
MSPILGYWKIKGLVQPTRLLLEYLEEKYEEHLYERDEGDKWRNKKFELGL

EFPNLPYYIDGDVKLTQSMAIIRYIADKHNMLGGCPKERAEISMLEGAVL

DIRYGVSRIAYSKDFETLKVDFLSKLPEMLKMFEDRLCHKTYLNGDHVTH

PDFMLYDALDVVLYMDPMCLDAFPKLVCFKKRIEAIPQIDKYLKSSKYIA

WPLQGWQATFGGGDHPPKSDGGSGSAALKIAAFNIRTFGETKMSNATLAS

YIVRIVRRYDIVLIQEVRDSHLVAVGKLLDYLNQDDPNTYHYVVSEPLGR

NSYKERYLFLFRPNKVSVLDTYQYDDGUESUGNDSFSREPAVVKFSSHST

KVKEFAIVALHSAPSDAVAEINSLYDVYLDVQQKWHLNDVMLMGDFNADU

SYVTSSQWSSIRLRTSSTFQWLIPDSADTTATSTNUAYDRIVVAGSLLQS

SVVPGSAAPFDFQAAYGLSNEMALAISDHYPVEVTLT.

In some embodiments, the DNase I comprises an amino acid sequence with at least 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to (SEQ ID NO: 4)
ALKIAAFNIRTFGETKMSNATLASYIVRIVRRYDIVLIQEVRDSHLVAVG

KLLDYLNQDDPNTYHYVVSEPLGRNSYKERYLFLFRPNKVSVLDTYQYDD

GUESUGNDSFSREPAVVKFSSHSTKVKEFAIVALHSAPSDAVAEINSLYD

VYLDVQQKWHLNDVMLMGDFNADUSYVTSSQWSSIRLRTSSTFQWLIPDS

-continued

ADTTATSTNUAYDRIVVAGSLLQSSVVPGSAAPFDFQAAYGLSNEMALAI

SDHYPVEVTLTGSHHHHHHGSGGGSGGSAWSHPQFEKGGGSGGGSGGSAW

SHPQFEK.

In some embodiments, the DNase I comprises an amino acid sequence with at least 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to (SEQ ID NO: 5)
MSPILGYWKIKGLVQPTRLLLEYLEEKYEEHLYERDEGDKWRNKKFELGL

EFPNLPYYIDGDVKLTQSMAIIRYIADKHNMLGGCPKERAEISMLEGAVL

DIRYGVSRIAYSKDFETLKVDFLSKLPEMLKMFEDRLCHKTYLNGDHVTH

PDFMLYDALDVVLYMDPMCLDAFPKLVCFKKRIEAIPQIDKYLKSSKYIA

WPLQGWQATFGGGDHPPKSDGGSGSAALKIAAFNIRTFGETKMSNATLAS

YIVRIVRRYDIVLIQEVRDSHLVAVGKLLDYLNQDDPNTYHYVVSEPLGR

NSYKERYLFLFRPNKVSVLDTYQYDDGUESUGNDSFSREPAVVKFSSHST

KVKEFAIVALHSAPSDAVAEINSLYDVYLDVQQKWHLNDVMLMGDFNADU

SYVTSSQWSSIRLRTSSTFQWLIPDSADTTATSTNUAYDRIVVAGSLLQS

SVVPGSAAPFDFQAAYGLSNEMALAISDHYPVEVTLTGSHHHHHHGSGGG

SGGSAWSHPQFEKGGGSGGGSGGSAWSHPQFEK.

In some embodiments, the DNase I comprises an affinity tag comprising an amino acid sequence with at least 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to (SEQ ID NO: 6)
MSPILGYWKIKGLVQPTRLLLEYLEEKYEEHLYERDEGDKWRNKKFELGL

EFPNLPYYIDGDVKLTQSMAIIRYIADKHNMLGGCPKERAEISMLEGAVL

DIRYGVSRIAYSKDFETLKVDFLSKLPEMLKMFEDRLCHKTYLNGDHVTH

PDFMLYDALDVVLYMDPMCLDAFPKLVCFKKRIEAIPQIDKYLKSSKYIA

WPLQGWQATFGGGDHPPKSD.

In some embodiments, the DNase I comprises an affinity tag comprising an amino acid sequence with at least 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to (SEQ ID NO: 7)
GSHHHHHHGSGGGSGGSAWSHPQFEKGGGSGGGSGGSAWSHPQFEK.

In some embodiments, the DNase I comprises an affinity tag comprising an amino acid sequence HHHHHH (SEQ ID NO: 8). In some embodiments, the DNase I comprises an affinity tag comprising an amino acid sequence AWSHPQFEK (SEQ ID NO 9).

In some embodiments, the DNase I comprises an affinity tag, wherein the DNase and affinity tag are separated by a linker. In some embodiments, the DNase I comprises a first affinity tag and a second affinity tag, wherein the DNase and the first affinity tag are separated by a linker, and wherein the DNase and the second affinity tag are separated by a linker. In some embodiments, the DNase I comprises a first affinity tag and a second affinity tag, wherein the first and second affinity tags are separated by a linker. In some embodiments, the DNase I comprises a first affinity tag, a second affinity tag and a third affinity tag, wherein the first, second and third affinity tags are each separated by a linker. In some embodiments, the DNase I comprises a first affinity tag, a second affinity tag, a third affinity tag and a fourth affinity tag, wherein the first, second, third and fourth affinity tags are each separated by a linker. In some embodiments, a linker comprises and amino acid sequence of (GS)n, (GGS)n, or (GGGS)n or a combination thereof, where n is an integer of rom 1-10. In some embodiments, a linker comprises and amino acid sequence of GSGGGSGGS (SEQ ID NO: 10). In some embodiments, a linker comprises and amino acid sequence of GGGSGGGSGGS (SEQ ID NO: 11). In some embodiments, a linker comprises and amino acid sequence of GS (SEQ ID NO: 12). In some embodiments, a linker comprises and amino acid sequence of GGSGSA (SEQ ID NO 13). In some embodiments, a linker comprises and amino acid sequence of GGSGSAA (SEQ ID NO 14).

In some embodiments, the one or more non-standard amino acids can be at position 102 of SEQ ID NO:1, position 105 of SEQ ID NO:1, position 174 of SEQ ID NO:1, or position 210 of SEQ ID NO:1. In some embodiments, the one or more non-standard amino acids can be at position 102 of SEQ ID NO:1, position 105 of SEQ ID NO:1, position 174 of SEQ ID NO:1, and position 210 of SEQ ID NO:1. In some embodiments, the one or more non-standard amino acids can be at position 102 of SEQ ID NO:1 and position 105 of SEQ ID NO:1. In some embodiments, the one or more non-standard amino acids can be at position 102 of SEQ ID NO:1 and position 174 of SEQ ID NO:1. In some embodiments, the one or more non-standard amino acids can be at position 102 of SEQ ID NO:1 and position 210 of SEQ ID NO:1. In some embodiments, the one or more non-standard amino acids can be at position 105 of SEQ ID NO:1 and position 174 of SEQ ID NO:1. In some embodiments, the one or more non-standard amino acids can be at position 105 of SEQ ID NO:1 and position 210 of SEQ ID NO:1. In some embodiments, the one or more non-standard amino acids can be at position 174 of SEQ ID NO:1 and position 210 of SEQ ID NO:1. In some embodiments, the one or more non-standard amino acids can be at position 102 of SEQ ID NO:1, position 105 of SEQ ID NO:1 and position 174 of SEQ ID NO:1. In some embodiments, the one or more non-standard amino acids can be at position 102 of SEQ ID NO:1, position 174 of SEQ ID NO:1, and position 210 of SEQ ID NO:1. In some embodiments, the one or more non-standard amino acids can be at position 102 of SEQ ID NO:1, position 105 of SEQ ID NO:1, and position 210 of SEQ ID NO:1. In some embodiments, the one or more non-standard amino acids can be at position 105 of SEQ ID NO:1, position 174 of SEQ ID NO:1, and position 210 of SEQ ID NO:1.

In some embodiments, a non-standard amino acid at position 102 can be directly linked by a bond to a non-standard amino acid at position 105. In some embodiments, a non-standard amino acid at position 174 can be directly linked by a bond to a non-standard amino acid at position 210. In some embodiments, a non-standard amino acid at position 102 can be directly linked by a bond to a non-standard amino acid at position 174. In some embodiments, a non-standard amino acid at position 102 can be directly linked by a bond to a non-standard amino acid at position 210. In some embodiments, a non-standard amino acid at position 105 can be directly linked by a bond to a non-standard amino acid at position 174. In some embodiments, a non-standard amino acid at position 105 can be directly linked by a bond to a non-standard amino acid at position 210.

In some embodiments, the bond can be a diselenide bond. In some embodiments, the diselenide bond can be in a location of a disulfide bond in a corresponding recombinant enzyme without the one or more non-standard amino acids.

In some embodiments, the $T_m$ of the corresponding stabilized DNase I polypeptide, functional fragment thereof, or variant thereof, can be less than 37° C. In some embodiments, the $T_m$ of the stabilized DNase I polypeptide, functional fragment thereof, or variant thereof, can be greater than 37° C., 40° C., 45° C., 50° C., 55° C., 60° C., or 65° C. In some embodiments, the $T_m$ of the stabilized DNase I polypeptide, functional fragment thereof, or variant thereof, can be at least 37° C., 40° C., 45° C., 50° C., 55° C., 60° C., 65° C. or greater.

In some embodiments, the $T_m$ of the stabilized DNase I polypeptide, functional fragment thereof, or variant thereof, can be at least 10° C. higher than the $T_m$ of the corresponding recombinant enzyme, functional fragment thereof, or variant thereof. In some embodiments, the $T_m$ of the stabilized DNase I polypeptide, functional fragment thereof, or variant thereof, can be at least 15° C. higher than the $T_m$ of the corresponding recombinant enzyme, functional fragment thereof, or variant thereof. In some embodiments, the $T_m$ of the stabilized DNase I polypeptide, functional fragment thereof, or variant thereof, can be at least 15° C., 20° C., 25° C., 30° C., 35° C., 40° C., 45° C., 50° C., 55° C., 60° C., 65° C. or greater higher than the $T_m$ of the corresponding recombinant enzyme, functional fragment thereof, or variant thereof. In some embodiments, the $T_m$ of the stabilized DNase I polypeptide, functional fragment thereof, or variant thereof, can be less than 10° C. higher than the $T_m$ of the corresponding recombinant enzyme, functional fragment thereof, or variant thereof.

In some embodiments, the stabilized DNase I polypeptide, functional fragment thereof, or variant thereof, can have a half-life in an environment that can be at least a 1.1, 1.2, 1.3, 1.4, 1.5, 1.6, 1.7, 1.8, 1.9, 2, 2.1, 2.2, 2.3, 2.4, 2.5, 3, 3.5, 4, 4.5, 5, 5.5, 6, 6.5, 7, 7.5, 8, 8.5, 9, 9.5, 10, 10.5, 11, 12, 13, 14, 15, 16, 17, 18, 19, 20, 25, 30, 35, 40, 45, 50, 55, 60, 65, 70, 75, 80, 85, 90, 95, 100, 200, 300, 400, 500, 600, 700, 800, 900, or 1000 or greater fold higher than a half-life of a corresponding DNase I polypeptide, functional fragment thereof, or variant thereof that does not comprise the one or more non-standard amino acids in the environment.

In some embodiments, the half-life of the DNase I polypeptide, functional fragment thereof, or variant thereof in the environment, can be greater than 1, 2, 3, 4, 5, 6, 7, 8, 9, 10, 11, 12, 13, 14, 15, 16, 17, 18, 19, 20, 21, 22, 23, 24 or more hours. In some embodiments, the half-life of the DNase I polypeptide, functional fragment thereof, or variant thereof in the environment, can be less than 1 hour.

In some embodiments, the half-life of the DNase I polypeptide, functional fragment thereof, or variant thereof in the environment, can be greater than 1, 2, 3, 4, 5, 6, 7, 8, 9, 10, 11, 12, 13, 14, 15, 16, 17, 18, 19, 20, 21, 22, 23, 24 or more days. In some embodiments, the half-life of the DNase I polypeptide, functional fragment thereof, or variant thereof in the environment, can be less than 1 day.

In some embodiments, the stabilized DNase I polypeptide can have at least a 1.1, 1.2, 1.3, 1.4, 1.5, 1.6, 1.7, 1.8, 1.9, 2, 3, 4, 5, 6, 7, 8, 10, 20, 30, 40, 50, 60, 70, 80, 90 or 100 fold higher endonuclease activity for a DNA substrate in an environment than an endonuclease activity for the DNA substrate of a corresponding DNase I polypeptide, functional fragment thereof, or variant thereof that does not comprise the one or more non-standard amino acids. In some embodiments, the stabilized DNase I polypeptide can have less than a 1.1 fold higher endonuclease activity for a DNA substrate in an environment than an endonuclease activity for the DNA substrate of a corresponding DNase I polypeptide, functional fragment thereof, or variant thereof that does not comprise the one or more non-standard amino acids.

In some embodiments, the stabilized DNase I polypeptide can have at least a 1.1, 1.2, 1.3, 1.4, 1.5, 1.6, 1.7, 1.8, 1.9, 2, 3, 4, 5, 6, 7, 8, 10, 20, 30, 40, 50, 60, 70, 80, 90 or 100 fold higher endonuclease activity for a DNA substrate after being present in an environment for at least 1, 2, 3, 4, 5, 6, 7, 8, 9, 10, 15, 20, 25, 30, 40, or 50 minutes than an endonuclease activity for the DNA substrate of a corresponding DNase I polypeptide, functional fragment thereof, or variant thereof that does not comprise the one or more non-standard amino acids after being present in the environment for at least 1, 2, 3, 4, 5, 6, 7, 8, 9, 10, 15, 20, 25, 30, 40, or 50 minutes. In some embodiments, the stabilized DNase I polypeptide can have less than a 1.1 fold higher endonuclease activity for a DNA substrate after being present in an environment for at least 1, 2, 3, 4, 5, 6, 7, 8, 9, 10, 15, 20, 25, 30, 40, or 50 minutes than an endonuclease activity for the DNA substrate of a corresponding DNase I polypeptide, functional fragment thereof, or variant thereof that does not comprise the one or more non-standard amino acids after being present in the environment for at least 1, 2, 3, 4, 5, 6, 7, 8, 9, 10, 15, 20, 25, 30, 40, or 50 minutes.

In some embodiments, the stabilized DNase I polypeptide can have at least a 1.1, 1.2, 1.3, 1.4, 1.5, 1.6, 1.7, 1.8, 1.9, 2, 3, 4, 5, 6, 7, 8, 10, 20, 30, 40, 50, 60, 70, 80, 90 or 100 fold higher endonuclease activity for a DNA substrate after being present in an environment for at least 1, 2, 3, 4, 5, 6, 7, 8, 9, 10, 12, 18, or 24 hours than an endonuclease activity for the DNA substrate of a corresponding DNase I polypeptide, functional fragment thereof, or variant thereof that does not comprise the one or more non-standard amino acids after being present in the environment for at least 1, 2, 3, 4, 5, 6, 7, 8, 9, 10, 12, 18, or 24 hours. In some embodiments, the stabilized DNase I polypeptide can have less than a 1.1 fold higher endonuclease activity for a DNA substrate after being present in an environment for at least 1, 2, 3, 4, 5, 6, 7, 8, 9, 10, 12, 18, or 24 hours than an endonuclease activity for the DNA substrate of a corresponding DNase I polypeptide, functional fragment thereof, or variant thereof that does not comprise the one or more non-standard amino acids after being present in the environment for at least 1, 2, 3, 4, 5, 6, 7, 8, 9, 10, 12, 18, or 24 hours.

In some embodiments, the DNA substrate can be genomic DNA. In some embodiments, the DNA substrate can be single-stranded DNA, double-stranded DNA, circular DNA, or cell free DNA.

In some embodiments, the environment can be an environment with a temperature of from 4° C.-98° C. In some embodiments, the environment can be an environment with a temperature of from 5° C.-97° C., 6° C.-96° C., 7° C.-95° C., 8° C.-94° C., 9° C.-93° C., 10° C.-92° C., 11° C.-91° C., 12° C.-90° C., 13° C.-89° C., 14° C.-88° C. 15° C.-85° C., 20° C.-75° C., 25° C.-70° C., 30° C.-65° C., 35° C.-60° C., 40° C.-55° C., or 45° C.-50° C. In some embodiments, the environment can be an environment with a temperature of at least 4° C., 5° C., 6° C., 7° C., 8° C., 9° C., 10° C., 11° C., 12° C., 13° C., 14° C., 15° C., 16° C., 17° C., 18° C., 19° C., 20° C., 21° C., 22° C., 23° C., 24° C., 25° C., 26° C., 27° C., 28° C., 29° C., 30° C., 35° C., 40° C., 45° C., 50° C., 55° C., 60° C., 65° C., 70° C., 75° C., 80° C. or greater. In some embodiments, the environment can be an environment with a temperature of less than 4° C.

In some embodiments, the environment can be an environment with a lysis buffer. In some embodiments, the lysis buffer can be NP-40 lysis buffer, RIPA (RadioImmunoPrecipitation Assay) lysis buffer, SDS (sodium dodecyl sulfate) lysis buffer, or ACK (Ammonium-Chloride-Potassium) lysing buffer.

In some embodiments, the environment can be an environment with a detergent at a concentration of from 0.01% to 20%. In some embodiments, the environment can be an environment with a detergent at a concentration of from 0.01% to 20%, 0.05% to 19.5%, 0.1% to 19%, 0.2% to 18.5%, 0.3% to 18%, 0.4% to 17.5%, 0.5% to 17%, 0.6% to 16.5%, 0.7% to 16%, 0.8% to 15%, 0.8% to 14%, 0.9% to 13%, or 1% to 12%. In some embodiments, the environment can be an environment with a detergent at a concentration of less than 0.01%. In some embodiments, the environment can be an environment with a detergent at a concentration of more than 20%.

In some embodiments, the detergent can be a non-ionic detergent. The non-ionic detergent can comprise Triton X-100, Triton X-114, NP-40, Brij-35, Brij-58, Tween 20, Tween 80, octyl glucoside, and octyl thioglucoside. In some embodiments, the detergent can be an ionic detergent. The ionic detergent can comprise sodium dodecyl sulfate (SDS). In some embodiment, the detergent can be a cationic detergent. The cationic detergent can be ethyl trimethyl ammonium bromide. In some embodiment, the detergent can be a zwitterionic detergent. The zwitterionic detergent can be CHAPS (3-[(3-cholamidopropyl)dimethylammonio]-1-propanesulfonate).

In some embodiments, the environment can comprise a divalent cation at a concentration of from 0.01 mM to 100 mM. In some embodiments, the environment can comprise a divalent cation at a concentration of from 0.01 mM to 100 mM, 0.05 mM to 95 mM, 0.1 mM to 90 mM, 0.5 mM to 85 mM, 1 mM to 80 mM, 5 mM to 75 mM, 10 mM to 70 mM, 15 mM to 65 mM, 20 mM to 60 mM, 25 mM to 55 mM, 30 mM to 50 mM, or 35 mM to 45 mM. In some embodiments, the environment can comprise a divalent cation at a concentration of less than 0.01 mM. In some embodiments, the environment can comprise a divalent cation at a concentration of more than 100 mM. In some embodiments, the divalent cation can be selected from the group consisting of $Mg^{2+}$, $Mn^{2+}$, $Ca^{2+}$, $Co^{2+}$, and $Zn^{2+}$.

In some embodiments, the environment can comprise a reducing agent at a concentration of from 0.01 mM to 100 mM. The reducing agent can be glutathione, albumin, or thioredoxin. In some embodiments, the environment can comprise a reducing agent at a concentration of from 0.01 mM to 100 mM, 0.05 mM to 95 mM, 0.1 mM to 90 mM, 0.5 mM to 85 mM, 1 mM to 80 mM, 5 mM to 75 mM, 10 mM to 70 mM, 15 mM to 65 mM, 20 mM to 60 mM, 25 mM to 55 mM, 30 mM to 50 mM, or 35 mM to 45 mM. In some embodiments, the environment can comprise a reducing agent at a concentration of less than 0.01 mM. In some embodiments, the environment can comprise a reducing agent at a concentration of more than 100 mM.

In some embodiments, the environment can have a pH of from 5-9. In some embodiments, the environment have a pH of from 6-8. In some embodiments, the environment can have a pH of from 7-8. In some embodiments, the environment can have a pH of less than 5. In some embodiments, the environment can have a pH of more than 9.

In some embodiments, the environment can have a salt concentration of from 10 mM to 1 M. In some embodiments, the environment can have a salt concentration of from 15 mM to 950 mM, 20 mM to 900 mM, 30 mM to 850 mM, 40 mM to 800 mM, 50 mM to 750 mM, 60 mM to 700 mM, 70 mM to 650 mM, 80 mM to 600 mM, 90 mM to 550 mM, 100 mM to 500 mM, 150 mM to 450 mM, or 200 mM to 400 mM. In some embodiments, the environment can have a salt concentration of less than 10 mM. In some embodiments, the environment can have a salt concentration of more than 1 M.

In some embodiments, the environment can be within a droplet. In some embodiments, the environment can be a blood circulatory system. In some embodiments, the environment can be any environment where the stabilized DNase I polypeptide, functional fragment thereof, or variant thereof can have the enzyme activity.

In some embodiments, the environment can have a reduction potential that is less than −150 mV, −160 mV, −170 mV, −180 mV, −190 mV, −200 mV, −210 mV, −220 mV, −230 mV, −240 mV, or −250 mV, −260 mV, −270 mV, −280 mV, −290 mV, −300 mV, −310 mV, −320 mV, −330 mV, −340 mV, or −350 mV, −360 mV, −370 mV, −380 mV, −390 mV, −400 mV, −410 mV, −420 mV, −430 mV, −440 mV, or −450 mV, −460 mV, −470 mV, −480 mV, −490 mV, −500 mV, −510 mV, −520 mV, −530 mV, −540 mV, or −550 mV, −560 mV, −570 mV, −580 mV, −590 mV, or −600 mV. In some embodiments, the environment can have a reduction potential that is more than −150 mV.

In some embodiments, the stabilized DNase I polypeptide, functional fragment thereof, or variant thereof, can be recombinant. In some embodiments, the recombinant can be generated using recombinant DNA technology, such as, for example, the stabilized DNase I polypeptide, functional fragment thereof, or variant thereof expressed by a bacteriophage or yeast expression system. In other embodiments, the recombinant can be generated by the synthesis of a DNA molecule encoding the stabilized DNase I polypeptide, functional fragment thereof, or variant thereof.

In some embodiments, the stabilized DNase I polypeptide, functional fragment thereof, or variant thereof, can be bovine DNase I. The stabilized DNase I polypeptide, functional fragment thereof, or variant thereof, can be any other kinds of DNases I, including, but not limited to, *E. coli* DNase I, *Microcella alkaliphila* DNase I, *Lactobacillus algidus* DNase I, *Vibrio cholerae* DNase I, *Bifidobacterium longum* DNase I, *Homo sapiens* DNase I, and *Raoultella ornithinolytica* DNase I.

In some embodiments, a composition can comprise a polynucleotide encoding the composition disclosed herein. In some embodiments, the polynucleotide can be a vector. The vector can be a fragment of nucleic acid molecules. The vector can be taken from a virus, a plasmid, or the cell of a higher organism. The vector can be stably maintained in an organism. The vector can be inserted with a foreign nucleic acid fragment for cloning purposes. The vector can comprise features that allow for the convenient insertion or removal of a nucleic acid fragment to or from vector. The vector can be genetically engineered plasmids.

In some embodiments, a bond directly linking two of the one or more non-standard amino acids of the stabilized DNase I polypeptide may not break in an environment, when the bond directly linking two of the one or more standard amino acids of the corresponding DNase I polypeptide may break in the same environment.

In some embodiments, the method of making the composition disclosed herein can comprise expressing an amino acid sequence of the stabilized DNase I polypeptide. In some embodiments, expressing can comprise expressing in a cell or in vitro.

In some embodiments, the cell can be a bacterial cell. In some embodiments, the cell can be a genomically recoded cell. In some embodiments, the cell may not be a bacterial cell. The cell can be obtained or isolated from a subject. The cell can be obtained or isolated from a tissue. The subject may be an animal such as a human, a mouse, a rat, a pig, a dog, a rabbit, a sheep, a horse, a chicken or other animal A cell may be a neuron. The cell may be one of the cells of a blood-brain barrier system. The cell may be a cell line, such as a neuronal cell line. The cell may be a primary cell, such as cells obtained from a brain of a subject. The cell may be a population of cells that may be isolated from a subject, such as a tissue biopsy, a cytology specimen, a blood sample, a fine needle aspirate (FNA) sample, or any combination thereof. The cell may be obtained from a bodily fluid such as urine, milk, sweat, lymph, blood, sputum, amniotic fluid, aqueous humour, vitreous humour, bile, cerebrospinal fluid, chyle, chyme, exudates, endolymph, perilymph, gastric acid, mucus, pericardial fluid, peritoneal fluid, pleural fluid, pus, rheum, saliva, sebum, serous fluid, smegma, sputum, tears, vomit, or other bodily fluid. The cell may comprise cancerous cells, non-cancerous cells, tumor cells, non-tumor cells, healthy cells, or any combination thereof.

In some embodiments, the cell can comprise a reassigned codon recognized by a stabilizing non-standard amino acid tRNA comprising an anticodon corresponding to the reassigned codon.

In some embodiments, the amino acid sequence of the stabilized DNase I polypeptide can be encoded by a polynucleotide sequence comprising at least one codon of a natural amino acid that can have been replaced by the reassigned codon. In some embodiments, the amino acid sequence of the stabilized DNase I polypeptide can be encoded by a polynucleotide sequence comprising at least one, two, or three codons of a natural amino acid that can be replaced by the reassigned codon.

In some embodiments, the stabilizing non-standard amino acid tRNA can be a selenocysteine tRNA.

In some embodiments, the method can comprise culturing the cell under conditions in which the amino acid sequence of the stabilized DNase I polypeptide can be expressed. In some embodiments, the reassigned codon can be UAG, UAA, UGA, or a combination thereof.

In some aspects, provided herein is a method comprising contacting DNA substrate that can be in a buffer, in reaction environment or on a solid surface to a stabilized deoxyribonuclease I (DNase I) polypeptide comprising one or more non-standard amino acids, a functional fragment thereof, or a variant thereof; wherein the stabilized DNase I polypeptide, functional fragment thereof, or variant thereof can catalyze cleavage or fragmentation of the DNA substrate at a higher rate than a corresponding DNase I polypeptide, functional fragment thereof, or variant thereof that does not comprise the one or more non-standard amino acids. In some embodiments, the stabilized DNase I polypeptide, functional fragment thereof, or variant thereof can catalyze cleavage or fragmentation of the DNA substrate at a 1.1, 1.2, 1.3, 1.4, 1.5, 1.6, 1.7, 1.8, 1.9, 2, 2.1, 2.2, 2.3, 2.4, 2.5, 3, 3.5, 4, 4.5, 5, 5.5, 6, 6.5, 7, 7.5, 8, 8.5, 9, 9.5, 10, 10.5, 11, 12, 13, 14, 15, 16, 17, 18, 19, 20, 25, 30, 35, 40, 45, 50, 55, 60, 65, 70, 75, 80, 85, 90, 95, 100, 200, 300, 400, 500, 600, 700, 800, 900, or 1000 or greater fold higher rate than a corresponding DNase I polypeptide, functional fragment thereof, or variant thereof that does not comprise the one or more non-standard amino acids.

In some embodiments, the stabilized DNase I polypeptide, functional fragment thereof, or variant thereof can be the stabilized DNase I polypeptide, functional fragment thereof, or variant thereof disclosed elsewhere herein. In some embodiments, the DNA substrate can be genomic DNA. In some embodiments, the DNA substrate is from a single cell. The single cell (or cell) is described elsewhere herein. In some embodiments, the method can comprise forming a plurality of vessels each comprising a single cell of a plurality of cells; the stabilized DNase I polypeptide, functional fragment thereof, or variant thereof; and a lysis buffer. In some embodiments, the method can further comprise lysing the single cell, thereby releasing the DNA substrate from the single cell.

In some embodiments, the method can further comprise barcoding the DNA substrate or fragments thereof. The barcode on the DNA substrate can be a natural or synthetic nucleic acid sequence comprised by a polynucleotide allowing for unambiguous identification of the polynucleotide and other sequences comprised by the polynucleotide having said barcode sequence. The barcode may uniquely identify a subject, a sample (such as a cell-free sample), a nucleic acid sequence (such as a sequence having one or more epigenetically modified bases), or any combination thereof. The barcode may be associated with a DNA substrate or a complementary strand. The DNA substrate can comprise a single barcode. The DNA substrate may comprise one or more barcodes, such as a first barcode and a second barcode. In some cases, the first barcode can be different from the second barcode. In some cases, each barcode of a plurality of barcodes may be a unique barcode. In some cases, a barcode may comprise a sample identification barcode. For example, a first barcode may comprise a unique barcode and a second barcode may comprise a sample identification barcode.

In some embodiments, the method can further comprise amplifying the DNA substrate or fragments thereof. The amplification can comprise amplification by polymerase chain reaction (PCR), loop mediated isothermal amplification, nucleic acid sequence based amplification, strand displacement amplification, multiple displacement amplification, rolling circle amplification, ligase chain reaction, helicase dependent amplification, ramification amplification method, clonal amplification, or any combination thereof. In some cases, the amplification can comprise at least 2, 3, 4, 5, 6, 7, 8, 9, 10, 11, 12, 13 or greater cycles of amplification. In some embodiments, the amplifying can comprise clonal amplification. In some cases, individual DNA substrate or fragment can be amplified in situ on a support. In some cases, the amplification generates no more than about $10^2$, $10^3$, $10^4$, $10^5$, $10^6$, $10^7$, $10^8$, $10^9$, $10^{10}$, $10^{11}$, $10^{12}$, $10^{15}$, or $10^{20}$ amplicons from a single amplified template.

In some embodiments, the method further comprises sequencing the DNA substrate or fragments thereof. The sequencing can comprise bisulfite-free sequencing, bisulfite sequencing, TET-assisted bisulfite (TAB) sequencing, ACE-sequencing, high-throughput sequencing, Maxam-Gilbert sequencing, massively parallel signature sequencing, Polony sequencing, 454 pyrosequencing, Sanger sequencing, Illumina sequencing, SOLiD sequencing, Ion Torrent semiconductor sequencing, DNA nanoball sequencing, Heliscope single molecule sequencing, single molecule real time (SMRT) sequencing, nanopore DNA sequencing, shot gun sequencing, RNA sequencing, Enigma sequencing, or any combination thereof. In some embodiments, the sequencing comprises whole genome sequencing. In some embodiments, the sequencing comprises high throughput sequencing, massively parallel sequencing, Sanger sequencing, or next generation sequencing.

In some embodiments, the plurality of vessels comprises a solid support. In some embodiments, DNA substrate is not attached to the solid support in a vessel. In some embodiments, the DNA substrate can be attached to the solid support in a vessel. The support can be any solid or semi-solid article on which reagents such as nucleic acids can be immobilized. Nucleic acids may be immobilized on the solid support by any method including but not limited to physical adsorption, by ionic or covalent bond formation, or combinations thereof. A solid support may include a polymeric, a glass, or a metallic material. Examples of solid supports include a membrane, a planar surface, a microtiter plate, a bead, a filter, a test strip, a slide, a cover slip, and a test tube, means any solid phase material upon which an oligomer is synthesized, attached, ligated or otherwise immobilized. The support may be composed of organic polymers such as polystyrene, polyethylene, polypropylene, polyfluoroethylene, polyethyleneoxy, and polyacrylamide, as well as co-polymers and grafts thereof. The support may also be inorganic, such as glass, silica, controlled-pore-glass (CPG), or reverse-phase silica. The configuration of a support may be in the form of beads, spheres, particles, granules, a gel, or a surface. Surfaces may be planar, substantially planar, or non-planar. Supports may be porous or non-porous, and may have swelling or non-swelling characteristics. The support can be shaped to comprise one or more wells, depressions or other containers, vessels, features or locations. A plurality of supports may be configured in an array at various locations.

In some embodiments, the buffer, the reaction environment or the solid surface can comprise primers specific to a sequence of the DNA substrate or fragments thereof. The primer may be a nucleic acid with known or unknown sequence. The primer may be single-stranded. In some cases, a primer can comprise a barcode (e.g. unique identifier sequence). The primer may be an amplification primer that hybridizes to the adapter and be extended using a target nucleic acid as a template in an amplification reaction. The primer can be a sequencing primer that hybridizes to the adapter and be extended using the target nucleic acid as a template in a sequencing reaction.

In some embodiments, the plurality of cells can comprise at least 2, 3, 4, 5, 5.5 6, 6.5 7, 8, 9, 10, 11, 12, 13, 14, 15, 16, 17, 18, 19, 20, 30, 40, 50, 60, 70, 80, 90, 100, 200, 300, 400, 500, 600, 700, 800, 900, 1000, 2000, 3000, 4000, 5000, 6000, 7000, 8000, 9000, 10,000, 15,000, 20,000, 25,000, 30,000, 35,000, 40,000, 45,000, 50,000, 60,000, 70,000, 80,000, 90,000, 100,000, 200,000, 300,000, 400,000, 500,000, 600,000, 700,000, 800,000, 900,000, $1\times10^6$, $2\times10^6$, $3\times10^6$, $4\times10^6$, $5\times10^6$, $6\times10^6$, $7\times10^6$, $8\times10^6$, $9\times10^6$, $1\times10^7$, $2\times10^7$, $3\times10^7$, $4\times10^7$, $5\times10^7$, $6\times10^7$, $7\times10^7$, $8\times10^7$, $9\times10^7$, $1\times10^8$, $2\times10^8$, $3\times10^8$, $4\times10^8$, $5\times10^8$, $6\times10^8$, $7\times10^8$, $8\times10^8$, $9\times10^8$, $1\times10^9$, $2\times10^9$, $3\times10^9$, $4\times10^9$, $5\times10^9$, $6\times10^9$, $7\times10^9$, $8\times10^9$, $9\times10^9$, $1\times10^{10}$, $2\times10^{10}$, $3\times10^{10}$, $4\times10^{10}$, $5\times10^{10}$, $6\times10^{10}$, $7\times10^{10}$, $8\times10^{10}$, $9\times10^{10}$, $1\times10^{11}$, $2\times10^{11}$, $3\times10^{11}$, $4\times10^{11}$, $5\times10^{11}$, $6\times10^{11}$, $7\times10^{11}$, $8\times10^{11}$, $9\times10^{11}$, $1\times10^{12}$, $2\times10^{12}$, $3\times10^{12}$, $4\times10^{12}$, $5\times10^{12}$, $6\times10^{12}$, $7\times10^{12}$, $8\times10^{12}$, or $9\times10^{12}$ cells.

In some embodiments, the plurality of cells can be from one or more biological samples. The biological samples can be from a subject, such as a tissue biopsy, a cytology specimen, a blood sample, a fine needle aspirate (FNA) sample, or any combination thereof. The biological sample may be obtained from a bodily fluid such as urine, milk, sweat, lymph, blood, sputum, amniotic fluid, aqueous humour, vitreous humour, bile, cerebrospinal fluid, chyle, chyme, exudates, endolymph, perilymph, gastric acid, mucus, pericardial fluid, peritoneal fluid, pleural fluid, pus, rheum, saliva, sebum, serous fluid, smegma, sputum, tears, vomit, or other bodily fluid.

In some embodiments, the one or more biological samples comprises at least 2, 3, 4, 5, 10, 20, 30, 40, 50, 60, 70, 80, 90 or 100 or more samples. In some embodiments, the one or more biological samples can comprise samples from different subjects. In some embodiments, the one or more biological samples can comprise samples from the same subject.

In some embodiments, the one or more biological sample is from a subject with a disease. The disease can include a cancer, a neurological disorder, or an autoimmune disease. In some embodiments, a disease may comprise a neurological disorder. In some cases, a neurological disorder may comprise Acquired Epileptiform Aphasia, Acute Disseminated Encephalomyelitis, Adrenoleukodystrophy, Agenesis of the corpus callosum, Agnosia, Aicardi syndrome, Alexander disease, Alpers' disease, Alternating hemiplegia, Alzheimer's disease, Amyotrophic lateral sclerosis (see Motor Neuron Disease), Anencephaly, Angelman syndrome, Angiomatosis, Anoxia, Aphasia, Apraxia, Arachnoid cysts, Arachnoiditis, Arnold-Chiari malformation, Arteriovenous malformation, Asperger's syndrome, Ataxia Telangiectasia, Attention Deficit Hyperactivity Disorder, Autism, Auditory processing disorder, Autonomic Dysfunction, Back Pain, Batten disease, Behcet's disease, Bell's palsy, Benign Essential Blepharospasm, Benign Focal Amyotrophy, Benign Intracranial Hypertension, Bilateral frontoparietal polymicrogyria, Binswanger's disease, Blepharospasm, Bloch-Sulzberger syndrome, Brachial plexus injury, Brain abscess, Brain damage, Brain injury, Brain tumor, Brown-Sequard syndrome, Canavan disease, Carpal tunnel syndrome (CTS), Causalgia, Central pain syndrome, Central pontine myelinolysis, Centronuclear myopathy, Cephalic disorder, Cerebral aneurysm, Cerebral arteriosclerosis, Cerebral atrophy, Cerebral gigantism, Cerebral palsy, Charcot-Marie-Tooth disease, Chiari malformation, Chorea, Chronic inflammatory demyelinating polyneuropathy (CIDP), Chronic pain, Chronic regional pain syndrome, Coffin Lowry syndrome, Coma, including Persistent Vegetative State, Congenital facial diplegia, Corticobasal degeneration, Cranial arteritis, Craniosynostosis, Creutzfeldt-Jakob disease, Cumulative trauma disorders, Cushing's syndrome, Cytomegalic inclusion body disease (CIBD), Cytomegalovirus Infection, Dandy-Walker syndrome, Dawson disease, De Morsier's syndrome, Dejerine-Klumpke palsy, Dejerine-Sottas disease, Delayed sleep phase syndrome, Dementia, Dermatomyositis, Neurological Dyspraxia, Diabetic neuropathy, Diffuse sclerosis, Dysautonomia, Dyscalculia, Dysgraphia, Dyslexia, Dystonia, Early infantile epileptic encephalopathy, Empty sella syndrome, Encephalitis, Encephalocele, Encephalotrigeminal angiomatosis, Encopresis, Epilepsy, Erb's palsy, Erythromelalgia, Essential tremor, Fabry's disease, Fahr's syndrome, Fainting, Familial spastic paralysis, Febrile seizures, Fisher syndrome, Friedreich's ataxia, FART Syndrome, Gaucher's disease, Gerstmann's syndrome, Giant cell arteritis, Giant cell inclusion disease, Globoid cell Leukodystrophy, Gray matter heterotopia, Guillain-Barre syndrome, HTLV-1 associated myelopathy, Hallervorden-Spatz disease, Head injury, Headache, Hemifacial Spasm, Hereditary Spastic Paraplegia, Heredopathia atactica polyneuritiformis, Herpes zoster oticus, Herpes zoster, Hirayama syndrome, Holoprosencephaly, Huntington's disease, Hydranencephaly, Hydrocephalus, Hypercortisolism, Hypoxia, Immune-Mediated encephalomyelitis, Inclusion body myositis, Incontinentia pigmenti, Infantile phytanic acid storage disease, Infantile Refsum disease, Infantile spasms, Inflammatory myopathy, Intracranial cyst, Intracranial hypertension, Joubert syndrome, Kearns-Sayre syndrome, Kennedy disease, Kinsbourne syndrome, Klippel Feil syndrome, Krabbe disease, Kugelberg-Welander disease, Kuru, Lafora disease, Lambert-Eaton myasthenic syndrome, Landau-Kleffner syndrome, Lateral medullary (Wallenberg) syndrome, Learning disabilities, Leigh's disease, Lennox-Gastaut syndrome, Lesch-Nyhan syndrome, Leukodystrophy, Lewy body dementia, Lissencephaly, Locked-In syndrome, Lou Gehrig's disease, Lumbar disc disease, Lyme disease—Neurological Sequelae, Machado-Joseph disease (Spinocerebellar ataxia type 3), Macrencephaly, Maple Syrup Urine Disease, Megalencephaly, Melkersson-Rosenthal syndrome, Menieres disease, Meningitis, Menkes disease, Metachromatic leukodystrophy, Microcephaly, Migraine, Miller Fisher syndrome, Mini-Strokes, Mitochondrial Myopathies, Mobius syndrome, Monomelic amyotrophy, Motor Neuron Disease, Motor skills disorder, Moyamoya disease, Mucopolysaccharidoses, Multi-Infarct Dementia, Multifocal motor neuropathy, Multiple sclerosis, Multiple system atrophy, Muscular dystrophy, Myalgic encephalomyelitis, Myasthenia gravis, Myelinoclastic diffuse sclerosis, Myoclonic Encephalopathy of infants, Myoclonus, Myopathy, Myotubular myopathy, Myotonia congenita, Narcolepsy, Neurofibromatosis, Neuroleptic malignant syndrome, Neurological manifestations of AIDS, Neurological sequelae of lupus, Neuromyotonia, Neuronal ceroid lipofuscinosis, Neuronal migration disorders, Niemann-Pick disease, Non 24-hour sleep-wake syndrome, Nonverbal learning disorder, O'Sullivan-McLeod syndrome, Occipital Neuralgia, Occult Spinal Dysraphism Sequence, Ohtahara syndrome, Olivopontocerebellar atrophy, Opsoclonus myoclonus syndrome, Optic neuritis, Orthostatic Hypotension, Overuse syndrome, Palinopsia, Paresthesia, Parkinson's disease, Paramyotonia Congenita, Paraneoplastic diseases, Paroxysmal attacks, Parry-Romberg syndrome, Rombergs Syndrome, Pelizaeus-Merzbacher disease, Periodic Paralyses, Peripheral neuropathy, Persistent Vegetative State, Pervasive neurological disorders, Photic sneeze reflex, Phytanic Acid Storage disease, Pick's disease, Pinched Nerve, Pituitary Tumors, PMG, Polio, Polymicrogyria, Polymyositis, Porencephaly, Post-Polio syndrome, Postherpetic Neuralgia (PHN), Postinfectious Encephalomyelitis, Postural Hypotension, Prader-Willi syndrome, Primary Lateral Sclerosis, Prion diseases, Progressive Hemifacial Atrophy also known as Rombergs Syndrome, Progressive multifocal leukoencephalopathy, Progressive Sclerosing Poliodystrophy, Progressive Supranuclear Palsy, Pseudotumor cerebri, Ramsay-Hunt syndrome (Type I and Type II), Rasmussen's encephalitis, Reflex sympathetic dystrophy syndrome, Refsum disease, Repetitive motion disorders, Repetitive stress injury, Restless legs syndrome, Retrovirus-associated myelopathy, Rett syndrome, Reye's syndrome, Rombergs Syndrome, Rabies, Saint Vitus dance, Sandhoff disease, Schytsophrenia, Schilder's disease, Schizencephaly, Sensory Integration Dysfunction, Septo-optic dysplasia, Shaken baby syndrome, Shingles, Shy-Drager syndrome, Sjogren's syndrome, Sleep apnea, Sleeping sickness, Snatiation, Sotos syndrome, Spasticity, Spina bifida, Spinal cord injury, Spinal cord tumors, Spinal muscular atrophy, Spinal stenosis, Steele-Richardson-Olszewski syndrome, see Progressive Supranuclear Palsy, Spinocerebellar ataxia, Stiff-person syndrome, Stroke, Sturge-Weber syndrome, Subacute sclerosing panencephalitis, Subcortical arteriosclerotic encephalopathy, Superficial siderosis, Sydenham's chorea, Syncope, Synesthesia, Syringomyelia, Tardive dyskinesia, Tay-Sachs disease, Temporal arteritis, Tethered spinal cord syndrome, Thomsen disease, Thoracic outlet syndrome, Tic Douloureux, Todd's paralysis, Tourette syndrome, Transient ischemic attack, Transmissible spongiform encephalopathies, Transverse myelitis, Traumatic brain injury, Tremor, Trigeminal neuralgia, Tropical spastic paraparesis, Trypanosomiasis, Tuberous sclerosis, Vasculitis including temporal arteritis, Von Hippel-Lindau disease (VHL), Viliuisk Encephalomyelitis (VE), Wallenberg's syndrome, Werdnig-Hoffman disease, West syndrome, Whiplash, Williams syndrome, Wilson's disease, X-Linked Spinal and Bulbar Muscular Atrophy, and Zellweger syndrome.

In some cases, the disease may comprise an autoimmune disease. In some cases, an autoimmune disease may comprise acute disseminated encephalomyelitis (ADEM), acute necrotizing hemorrhagic leukoencephalitis, Addison's disease, agammaglobulinemia, allergic asthma, allergic rhinitis, alopecia areata, amyloidosis, ankylosing spondylitis, anti-GBM/anti-TBM nephritis, antiphospholipid syndrome (APS), autoimmune aplastic anemia, autoimmune dysautonomia, autoimmune hepatitius, autoimmune hyperlipidemia, autoimmune immunodeficiency, autoimmune inner ear disease (AIED), autoimmune myocarditis, autoimmune pancreatitis, autoimmune retinopathy, autoimmune thrombocytopenic purpura (ATP), autoimmune thyroid disease, axonal & neuronal neuropathies, Balo disease, Behcet's disease, bullous pemphigoid, cardiomyopathy, Castlemen disease, celiac sprue (non-tropical), Chagas disease, chronic fatigue syndrome, chronic inflammatory demyelinating polyneuropathy (CIDP), chronic recurrent multifocal ostomyelitis (CRMO), Churg-Strauss syndrome, cicatricial pemphigoid/benign mucosal pemphigoid, Crohn's disease, Cogan's syndrome, cold agglutinin disease, congenital heart block, coxsackie myocarditis, CREST disease, essential mixed cryoglobulinemia, demyelinating neuropathies, dermatomyositis, Devic's disease (neuromyelitis optica), discoid lupus, Dressler's syndrome, endometriosis, eosinophillic fasciitis, erythema nodosum, experimental allergic encephalomyelitis, Evan's syndrome, fibromyalgia, fibrosing alveolitis, giant cell arteritis (temporal arteritis), glomerulonephritis, Goodpasture's syndrome, Grave's disease, Guillain-Barre syndrome, Hashimoto's encephalitis, Hashimoto's thyroiditis, hemolytic anemia, Henock-Schoniein purpura, herpes gestationis, hypogammaglobulinemia, idiopathic thrombocytopenic purpura (ITP), IgA nephropathy, immunoregulatory lipoproteins, inclusion body myositis, insulin-dependent diabetes (type 1), interstitial cystitis, juvenile arthritis, juvenile diabetes, Kawasaki syndrome, Lambert-Eaton syndrome, leukocytoclastic vasculitis, lichen planus, lichen sclerosus, ligneous conjunctivitis, linear IgA disease (LAD), Lupus (SLE), Lyme disease, Meniere's disease, microscopic polyangitis, mixed connective tissue disease (MCTD), Mooren's ulcer, Mucha-Habermann disease, multiple sclerosis, myasthenia gravis, myositis, narcolepsy, neuromyelitis optica (Devic's), neutropenia, ocular cicatricial pemphigoid, optic neuritis, palindromic rheumatism, PANDAS (Pediatric Autoimmune Neuropsychiatric Disorders Associated with *Streptococcus*), paraneoplastic cerebellar degeneration, paroxysmal nocturnal hemoglobinuria (PNH), Parry Romberg syndrome, Parsonnage-Turner syndrome, pars plantis (peripheral uveitis), *pemphigus*, peripheral neuropathy, perivenous encephalomyelitis, pernicious anemia, POEMS syndrome, polyarteritis nodosa, type I, II & III autoimmune polyglandular syndromes, polymyalgia rheumatic, polymyositis, postmyocardial infarction syndrome, postpericardiotomy syndrome, progesterone dermatitis, primary biliary cirrhosis, primary sclerosing cholangitis, psoriasis, psoriatic arthritis, idiopathic pulmonary fibrosis, pyoderma gangrenosum, pure red cell aplasia, Raynaud's phenomena, reflex sympathetic dystrophy, Reiter's syndrome, relapsing polychondritis, restless legs syndrome, retroperitoneal fibrosis, rheumatic fever, rheumatoid arthritis, sarcoidosis, Schmidt syndrome, scleritis, scleroderma, Slogren's syndrome, sperm and testicular autoimmunity, stiff person syndrome, subacute bacterial endocarditis (SBE), sympathetic ophthalmia, Takayasu's arteritis, temporal arteritis/giant cell arteries, thrombocytopenic purpura (TPP), Tolosa-Hunt syndrome, transverse myelitis, ulcerative colitis, undifferentiated connective tissue disease (UCTD), uveitis, vasculitis, vesiculobullous dermatosis, vitiligo or Wegener's granulomatosis, chronic active hepatitis, primary biliary cirrhosis, cadilated cardiomyopathy, myocarditis, autoimmune polyendocrine syndrome type I (APS-I), cystic fibrosis vasculitides, acquired hypoparathyroidism, coronary artery disease, *Pemphigus foliaceus, Pemphigus vulgaris*, Rasmussen encephalitis, autoimmune gastritis, insulin hypoglycemic syndrome (Hirata disease), Type B insulin resistance, acanthosis, systemic lupus erythematosus (SLE), pernicious anemia, treatment-resistant Lyme arthritis, polyneuropathy, demyelinating diseases, atopic dermatitis, autoimmune hypothyroidism, vitiligo, thyroid associated ophthalmopathy, autoimmune coeliac disease, ACTH deficiency, dermatomyositis, Sjogren syndrome, systemic sclerosis, progressive systemic sclerosis, morphea, primary antiphospholipid syndrome, chronic idiopathic urticaria, connective tissue syndromes, necrotizing and crescentic glomerulonephritis (NCGN), systemic vasculitis, Raynaud syndrome, chronic liver disease, visceral leishmaniasis, autoimmune C1 deficiency, membrane proliferative glomerulonephritis (MPGN), prolonged coagulation time, immunodeficiency, atherosclerosis, neuronopathy, paraneoplastic *pemphigus*, paraneoplastic stiff man syndrome, paraneoplastic encephalomyelitis, subacute autonomic neuropathy, cancer-associated retinopathy, paraneoplastic opsoclonus myoclonus ataxia, lower motor neuron syndrome and Lambert-Eaton myasthenic syndrome.

In some cases, a disease may comprise AIDS, anthrax, botulism, brucellosis, chancroid, chlamydial infection, cholera, coccidioidomycosis, cryptosporidiosis, cyclosporiasis, dipheheria, ehrlichiosis, arboviral encephalitis, enterohemorrhagic *Escherichia coli*, giardiasis, gonorrhea, dengue fever, *Haemophilus influenza*, Hansen's disease (Leprosy), hantavirus pulmonary syndrome, hemolytic uremic syndrome, hepatitis A, hepatitis B, hepatitis C, human immunodeficiency virus, legionellosis, listeriosis, lyme disease, malaria, measles. Meningococcal disease, mumps, pertussis (whooping cough), plague, paralytic poliomyelitis, psittacosis, Q fever, rabies, rocky mountain spotted fever, rubella, congenital rubella syndrome (SARS), shigellosis, smallpox, streptococcal disease (invasive group A), streptococcal toxic shock syndrome, *Streptococcus pneumonia*, syphilis, tetanus, toxic shock syndrome, trichinosis, tuberculosis, tularemia, typhoid fever, vancomycin intermediate resistant staphylocossus aureus, varicella, yellow fever, variant Creutzfeldt-Jakob disease (vCJD), Eblola hemorrhagic fever, Echinococcosis, Hendra virus infection, human monkeypox, influenza A, H5N1, lassa fever, Margurg hemorrhagic fever, Nipah virus, O'nyong fever, Rift valley fever, Venezuelan equine encephalitis and West Nile virus.

In some cases, a disease may comprise a cancer. In some cases, a cancer may comprise thyroid cancer, adrenal cortical cancer, anal cancer, aplastic anemia, bile duct cancer, bladder cancer, bone cancer, bone metastasis, central nervous system (CNS) cancers, peripheral nervous system (PNS) cancers, breast cancer, Castleman's disease, cervical cancer, childhood Non-Hodgkin's lymphoma, lymphoma, colon and rectum cancer, endometrial cancer, esophagus cancer, Ewing's family of tumors (e.g. Ewing's sarcoma), eye cancer, gallbladder cancer, gastrointestinal carcinoid tumors, gastrointestinal stromal tumors, gestational trophoblastic disease, hairy cell leukemia, Hodgkin's disease, Kaposi's sarcoma, kidney cancer, laryngeal and hypopharyngeal cancer, acute lymphocytic leukemia, acute myeloid leukemia, children's leukemia, chronic lymphocytic leukemia, chronic myeloid leukemia, liver cancer, lung cancer, lung carcinoid tumors, Non-Hodgkin's lymphoma, male breast cancer, malignant mesothelioma, multiple myeloma, myelodysplastic syndrome, myeloproliferative disorders, nasal cavity and paranasal cancer, nasopharyngeal cancer, neuroblastoma, oral cavity and oropharyngeal cancer, osteosarcoma, ovarian cancer, pancreatic cancer, penile cancer, pituitary tumor, prostate cancer, retinoblastoma, rhabdomyosarcoma, salivary gland cancer, sarcoma (adult soft tissue cancer), melanoma skin cancer, non-melanoma skin cancer, stomach cancer, testicular cancer, thymus cancer, uterine cancer (e.g. uterine sarcoma), vaginal cancer, vulvar cancer, or Waldenstrom's macroglobulinemia.

In some cases, a disease can include hyperproliferative disorders. Malignant hyperproliferative disorders can be stratified into risk groups, such as a low risk group and a medium-to-high risk group. Hyperproliferative disorders can include but may not be limited to cancers, hyperplasia, or neoplasia. In some cases, the hyperproliferative cancer can be breast cancer such as a ductal carcinoma in duct tissue of a mammary gland, medullary carcinomas, colloid carcinomas, tubular carcinomas, and inflammatory breast cancer; ovarian cancer, including epithelial ovarian tumors such as adenocarcinoma in the ovary and an adenocarcinoma that has migrated from the ovary into the abdominal cavity; uterine cancer; cervical cancer such as adenocarcinoma in the cervix epithelial including squamous cell carcinoma and adenocarcinomas; prostate cancer, such as a prostate cancer selected from the following: an adenocarcinoma or an adenocarcinoma that has migrated to the bone; pancreatic cancer such as epithelioid carcinoma in the pancreatic duct tissue and an adenocarcinoma in a pancreatic duct; bladder cancer such as a transitional cell carcinoma in urinary bladder, urothelial carcinomas (transitional cell carcinomas), tumors in the urothelial cells that line the bladder, squamous cell carcinomas, adenocarcinomas, and small cell cancers; leukemia such as acute myeloid leukemia (AML), acute lymphocytic leukemia, chronic lymphocytic leukemia, chronic myeloid leukemia, hairy cell leukemia, myelodysplasia, myeloproliferative disorders, acute myelogenous leukemia (AML), chronic myelogenous leukemia (CML), mastocytosis, chronic lymphocytic leukemia (CLL), multiple myeloma (MM), and myelodysplastic syndrome (MDS); bone cancer; lung cancer such as non-small cell lung cancer (NSCLC), which may be divided into squamous cell carcinomas, adenocarcinomas, and large cell undifferentiated carcinomas, and small cell lung cancer; skin cancer such as basal cell carcinoma, melanoma, squamous cell carcinoma and actinic keratosis, which may be a skin condition that sometimes develops into squamous cell carcinoma; eye retinoblastoma; cutaneous or intraocular (eye) melanoma; primary liver cancer (cancer that begins in the liver); kidney cancer; autoimmune deficiency syndrome (AIDS)-related lymphoma such as diffuse large B-cell lymphoma, B-cell immunoblastic lymphoma and small non-cleaved cell lymphoma; Kaposi's Sarcoma; viral-induced cancers including hepatitis B virus (HBV), hepatitis C virus (HCV), and hepatocellular carcinoma; human lymphotropic virus-type 1 (HTLV-1) and adult T-cell leukemia/lymphoma; and human papilloma virus (HPV) and cervical cancer; central nervous system (CNS) cancers such as primary brain tumor, which includes gliomas (astrocytoma, anaplastic astrocytoma, or glioblastoma multiforme), oligodendrogliomas, ependymomas, meningiomas, lymphomas, schwannomas, and medulloblastomas; peripheral nervous system (PNS) cancers such as acoustic neuromas and malignant peripheral nerve sheath tumors (MPNST) including neurofibromas and schwannomas, malignant fibrous cytomas, malignant fibrous histiocytomas, malignant meningiomas, malignant mesotheliomas, and malignant mixed Müllerian tumors; oral cavity and oropharyngeal cancer such as hypopharyngeal cancer, laryngeal cancer, nasopharyngeal cancer, and oropharyngeal cancer; stomach cancer such as lymphomas, gastric stromal tumors, and carcinoid tumors; testicular cancer such as germ cell tumors (GCTs), which include seminomas and nonseminomas, and gonadal stromal tumors, which include Leydig cell tumors and Sertoli cell tumors; thymus cancer such as to thymomas, thymic carcinomas, Hodgkin disease, non-Hodgkin lymphomas carcinoids or carcinoid tumors; rectal cancer; and colon cancer. In some cases, the diseases stratified, classified, characterized, or diagnosed by the methods of the present disclosure include but may not be limited to thyroid disorders such as for example benign thyroid disorders including but not limited to follicular adenomas, Hurthle cell adenomas, lymphocytic thyroiditis, and thyroid hyperplasia. In some cases, the diseases stratified, classified, characterized, or diagnosed by the methods of the present disclosure include but may not be limited to malignant thyroid disorders such as for example follicular carcinomas, follicular variant of papillary thyroid carcinomas, medullary carcinomas, and papillary carcinomas.

The disease can include a genetic disorder. A genetic disorder may be an illness caused by abnormalities in genes or chromosomes. Genetic disorders can be grouped into two categories: single gene disorders and multifactorial and polygenic (complex) disorders. A single gene disorder can be the result of a single mutated gene. Inheriting a single gene disorder can include but not be limited to autosomal dominant, autosomal recessive, X-linked dominant, X-linked recessive, Y-linked and mitochondrial inheritance. Only one mutated copy of the gene can be necessary for a person to be affected by an autosomal dominant disorder. Examples of autosomal dominant type of disorder can include but may not be limited to Huntington's disease, Neurofibromatosis 1, Marfan Syndrome, Hereditary non-polyposis colorectal cancer, or Hereditary multiple exostoses. In autosomal recessive disorders, two copies of the gene must be mutated for a subject to be affected by an autosomal recessive disorder. Examples of this type of disorder can include but may not be limited to cystic fibrosis, sickle-cell disease (also partial sickle-cell disease), Tay-Sachs disease, Niemann-Pick disease, or spinal muscular atrophy. X-linked dominant disorders are caused by mutations in genes on the X chromosome such as X-linked hypophosphatemic rickets. Some X-linked dominant conditions such as Rett syndrome, Incontinentia Pigmenti type 2 and Aicardi Syndrome can be fatal. X-linked recessive disorders are also caused by mutations in genes on the X chromosome. Examples of this type of disorder can include but are not limited to Hemophilia A, Duchenne muscular dystrophy, red-green color blindness, muscular dystrophy and Androgenetic alopecia. Y-linked disorders are caused by mutations on the Y chromosome. Examples can include but are not limited to Male Infertility and hypertrichosis pinnae. The genetic disorder of mitochondrial inheritance, also known as maternal inheritance, can apply to genes in mitochondrial DNA such as in Leber's Hereditary Optic Neuropathy.

In some embodiments, plurality of cells can comprise a plurality of bacterial cells or a plurality of fungal cells. In some embodiments, the plurality of bacterial cells or the plurality of fungal cells can comprise at least 2, 3, 4, 5, 5.5 6, 6.5 7, 8, 9, 10, 11, 12, 13, 14, 15, 16, 17, 18, 19, 20, 30, 40, 50, 60, 70, 80, 90, 100, 200, 300, 400, 500, 600, 700, 800, 900, 1000, 2000, 3000, 4000, 5000, 6000, 7000, 8000, 9000, 10,000, 15,000, 20,000, 25,000, 30,000, 35,000, 40,000, 45,000, 50,000, 60,000, 70,000, 80,000, 90,000, 100,000, 200,000, 300,000, 400,000, 500,000, 600,000, 700, 000, 800,000, 900,000, $1\times10^6$, $2\times10^6$, $3\times10^6$, $4\times10^6$, $5\times10^6$, $6\times10^6$, $7\times10^6$, $8\times10^6$, $9\times10^6$, $1\times10^7$, $2\times10^7$, $3\times10^7$, $4\times10^7$, $5\times10^7$, $6\times10^7$, $7\times10^7$, $8\times10^7$, $9\times10^7$, $1\times10^8$, $2\times10^8$, $3\times10^8$, $4\times10^8$, $5\times10^8$, $6\times10^8$, $7\times10^8$, $8\times10^8$, $9\times10^8$, $1\times10^9$, $2\times10^9$, $3\times10^9$, $4\times10^9$, $5\times10^9$, $6\times10^9$, $7\times10^9$, $8\times10^9$, $9\times10^9$, $1\times10^{10}$, $2\times10^{10}$, $3\times10^{10}$, $4\times10^{10}$, $5\times10^{10}$, $6\times10^{10}$, $7\times10^{10}$, $8\times10^{10}$, $9\times10^{10}$, $1\times10^{11}$, $2\times10^{11}$, $3\times10^{11}$, $4\times10^{11}$, $5\times10^{11}$, $6\times10^{11}$, $7\times10^{11}$, $8\times10^{11}$, $9\times10^{11}$, $1\times10^{12}$, $2\times10^{12}$, $3\times10^{12}$, $4\times10^{12}$, $5\times10^{12}$, $6\times10^{12}$, $7\times10^{12}$, $8\times10^{12}$, or $9\times10^{12}$ cells.

In some embodiments, plurality of cells comprises a plurality of immune cells. In some embodiments, the plurality of immune cells can comprise at least 2, 3, 4, 5, 5.5, 6, 6.5, 7, 8, 9, 10, 11, 12, 13, 14, 15, 16, 17, 18, 19, 20, 30, 40, 50, 60, 70, 80, 90, 100, 200, 300, 400, 500, 600, 700, 800, 900, 1000, 2000, 3000, 4000, 5000, 6000, 7000, 8000, 9000, 10,000, 15,000, 20,000, 25,000, 30,000, 35,000, 40,000, 45,000, 50,000, 60,000, 70,000, 80,000, 90,000, 100,000, 200,000, 300,000, 400,000, 500,000, 600,000, 700, 000, 800,000, 900,000, $1\times10^6$, $2\times10^6$, $3\times10^6$, $4\times10^6$, $5\times10^6$, $6\times10^6$, $7\times10^6$, $8\times10^6$, $9\times10^6$, $1\times10^7$, $2\times10^7$, $3\times10^7$, $4\times10^7$, $5\times10^7$, $6\times10^7$, $7\times10^7$, $8\times10^7$, $9\times10^7$, $1\times10^8$, $2\times10^8$, $3\times10^8$, $4\times10^8$, $5\times10^8$, $6\times10^8$, $7\times10^8$, $8\times10^8$, $9\times10^8$, $1\times10^9$, $2\times10^9$, $3\times10^9$, $4\times10^9$, $5\times10^9$, $6\times10^9$, $7\times10^9$, $8\times10^9$, $9\times10^9$, $1\times10^{10}$, $2\times10^{10}$, $3\times10^{10}$, $4\times10^{10}$, $5\times10^{10}$, $6\times10^{10}$, $7\times10^{10}$, $8\times10^{10}$, $9\times10^{10}$, $1\times10^{11}$, $2\times10^{11}$, $3\times10^{11}$, $4\times10^{11}$, $5\times10^{11}$, $6\times10^{11}$, $7\times10^{11}$, $8\times10^{11}$, $9\times10^{11}$, $1\times10^{12}$, $2\times10^{12}$, $3\times10^{12}$, $4\times10^{12}$, $5\times10^{12}$, $6\times10^{12}$, $7\times10^{12}$, $8\times10^{12}$, or $9\times10^{12}$ cells.

In some embodiments, plurality of cells comprises a plurality of diseased cells. In some embodiments, the plurality of diseased cells can comprise at least 2, 3, 4, 5, 5.5, 6, 6.5, 7, 8, 9, 10, 11, 12, 13, 14, 15, 16, 17, 18, 19, 20, 30, 40, 50, 60, 70, 80, 90, 100, 200, 300, 400, 500, 600, 700, 800, 900, 1000, 2000, 3000, 4000, 5000, 6000, 7000, 8000, 9000, 10,000, 15,000, 20,000, 25,000, 30,000, 35,000, 40,000, 45,000, 50,000, 60,000, 70,000, 80,000, 90,000, 100,000, 200,000, 300,000, 400,000, 500,000, 600,000, 700, 000, 800,000, 900,000, $1\times10^6$, $2\times10^6$, $3\times10^6$, $4\times10^6$, $5\times10^6$, $6\times10^6$, $7\times10^6$, $8\times10^6$, $9\times10^6$, $1\times10^7$, $2\times10^7$, $3\times10^7$, $4\times10^7$, $5\times10^7$, $6\times10^7$, $7\times10^7$, $8\times10^7$, $9\times10^7$, $1\times10^8$, $2\times10^8$, $3\times10^8$, $4\times10^8$, $5\times10^8$, $6\times10^8$, $7\times10^8$, $8\times10^8$, $9\times10^8$, $1\times10^9$, $2\times10^9$, $3\times10^9$, $4\times10^9$, $5\times10^9$, $6\times10^9$, $7\times10^9$, $8\times10^9$, $9\times10^9$, $1\times10^{10}$, $2\times10^{10}$, $3\times10^{10}$, $4\times10^{10}$, $5\times10^{10}$, $6\times10^{10}$, $7\times10^{10}$, $8\times10^{10}$, $9\times10^{10}$, $1\times10^{11}$, $2\times10^{11}$, $3\times10^{11}$, $4\times10^{11}$, $5\times10^{11}$, $6\times10^{11}$, $7 \times 10^{11}$, $8 \times 10^{11}$, $9 \times 10^{11}$, $1 \times 10^{12}$, $2 \times 10^{12}$, $3 \times 10^{12}$, $4 \times 10^{12}$, $5 \times 10^{12}$, $6 \times 10^{12}$, $7 \times 10^{12}$, $8 \times 10^{12}$, or $9 \times 10^{12}$ cells.

In some embodiments, plurality of cells comprises a plurality of cancer cells. In some embodiments, the plurality of cancer cells can comprise at least 2, 3, 4, 5, 5.5 6, 6.5 7, 8, 9, 10, 11, 12, 13, 14, 15, 16, 17, 18, 19, 20, 30, 40, 50, 60, 70, 80, 90, 100, 200, 300, 400, 500, 600, 700, 800, 900, 1000, 2000, 3000, 4000, 5000, 6000, 7000, 8000, 9000, 10,000, 15,000, 20,000, 25,000, 30,000, 35,000, 40,000, 45,000, 50,000, 60,000, 70,000, 80,000, 90,000, 100,000, 200,000, 300,000, 400,000, 500,000, 600,000, 700,000, 800,000, 900,000, $1 \times 10^6$, $2 \times 10^6$, $3 \times 10^6$, $4 \times 10^6$, $5 \times 10^6$, $6 \times 10^6$, $7 \times 10^6$, $8 \times 10^6$, $9 \times 10^6$, $1 \times 10^7$, $2 \times 10^7$, $3 \times 10^7$, $4 \times 10^7$, $5 \times 10^7$, $6 \times 10^7$, $7 \times 10^7$, $8 \times 10^7$, $9 \times 10^7$, $1 \times 10^8$, $2 \times 10^8$, $3 \times 10^8$, $4 \times 10^8$, $5 \times 10^8$, $6 \times 10^8$, $7 \times 10^8$, $8 \times 10^8$, $9 \times 10^8$, $1 \times 10^9$, $2 \times 10^9$, $3 \times 10^9$, $4 \times 10^9$, $5 \times 10^9$, $6 \times 10^9$, $7 \times 10^9$, $8 \times 10^9$, $9 \times 10^9$, $1 \times 10^{10}$, $2 \times 10^{10}$, $3 \times 10^{10}$, $4 \times 10^{10}$, $5 \times 10^{10}$, $6 \times 10^{10}$, $7 \times 10^{10}$, $8 \times 10^{10}$, $9 \times 10^{10}$, $1 \times 10^{11}$, $2 \times 10^{11}$, $3 \times 10^{11}$, $4 \times 10^{11}$, $5 \times 10^{11}$, $6 \times 10^{11}$, $7 \times 10^{11}$, $8 \times 10^{11}$, $9 \times 10^{11}$, $1 \times 10^{12}$, $2 \times 10^{12}$, $3 \times 10^{12}$, $4 \times 10^{12}$, $5 \times 10^{12}$, $6 \times 10^{12}$, $7 \times 10^{12}$, $8 \times 10^{12}$, or $9 \times 10^{12}$ cells.

The enzymes described herein can be made in a host cell, or in vitro, in cell-free synthetic systems. Host cells may be any that can be robustly recoded. These can be bacterial cells that have well developed genetic systems, of which *E. coli* is exemplary. Other bacterial species can also be used. Cell-free systems for producing the proteins may be coupled transcription/translation systems or only translation systems. A notable aspect of the methods of the invention is the use of biological syntheses rather than chemical synthesis means.

Culturing of recoded cells with the constructed nucleic acid sequences may be by any means known in the art. The culturing may be batch or continuous, in shaker flasks or in fermenters or immobilized on solid surfaces, such as small particles contained in larger vessels. Typically the culture medium will be supplemented with a source of selenium, such as $Na_2SeO_3$. As is known in the art, production of the desired protein variant may be under the control of an inducer or a repressor. Any such systems which are known in the art may be selected for convenience of construction and protein production.

The above disclosure generally describes the present invention. All references disclosed herein are expressly incorporated by reference. A more complete understanding can be obtained by reference to the following specific examples which are provided herein for purposes of illustration only, and are not intended to limit the scope of the invention.

EXAMPLES

Example 1—Expression and Purification

RTΔA 2X310K cells transformed with plasmid pUC-TetO-GST-DNase_Sec-HisAltStrep bearing a gene encoding DNase I with UAG codons directing selenocysteine incorporation substituted in place of all cysteine codons will be diluted 1/250 in 1 L of terrific broth supplemented with 1000 µg/mL carbenicillin, 12.5 µg/mL tetracycline and 25 µM Na2SeO3 and will be induced with (1 mM) 3,4-dihydroxybenzoic acid during mid log phase followed by growth O/N at 37° C. Cells will be harvested by centrifugation at 8000×g for 10 min and resuspended in 25 mL of wash buffer (50 mM K2HPO4, 300 mM NaCl, 20 mM imidazole and 10% glycerol at pH 8.0) with protease inhibitor cocktail (cOmplete, mini EDTA free, Roche) and lysozyme (0.5 mg/mL). Following a 20 min incubation at 4° C. with gentle agitation cells will be lysed by sonication (Model 500, Fisher Scientific) and clarified three times by centrifugation at 35000×g for 30 min. Lysate will be filtered through a 0.2 µm membrane and protein will be recovered by IMAC using Ni-NTA resin and gravity flow columns Eluate will be concentrated to 3 mL and dialyzed against TBS pH 7.5 followed by purification to apparent homogeneity by size exclusion FPLC. A significant proportion of the sample may be precipitated during dialysis and an additional proportion of the sample may be present in the less stable/soluble dimer form. Final yield of soluble enzyme will be determined.

RTΔA 2X310K-T7 cells transformed with plasmid pUC-TetO-GST-DNase_Sec-HisAltStrep bearing a gene encoding a DNase I UAG codons directing selenocysteine incorporation substituted in place of all cysteine codons will be diluted 1/250 in 1 L of terrific broth supplemented with 1000 µg/mL carbenicillin, 33 µg/mL chloramphenicol and 25 µM Na2SeO3 and induced with 200 ng/mL anhydrotetracycline during mid log phase followed by growth O/N at 30° C. Cells will be harvested and purified by IMAC as previously described. To reduce precipitation, samples will be dialyzed in larger volumes (>6 mL). Protein samples will be purified to homogeneity by either size exclusion FPLC or anion exchange chromatography (HiTrap Q HP column). Final yield of soluble enzyme will be determined.

Example 2—Mass Spectrometry

Intact protein samples will be analyzed using methods described previously. Selenoprotein samples will be buffer exchanged into LC-MS grade water using 10 kDa molecular weight cut-off filters. Once the buffer exchange is complete the samples will be diluted to 20 µM in a methanol/water/formic acid (50/49/1) solution. After dilution, protein solutions will be infused into an Orbitrap Elite mass spectrometer (Thermo Fisher Scientific Instruments, Bremen, Germany) at a rate of 3 µL/min via electrospray ionization. In order to confirm the incorporation of selenocysteine, intact mass analysis will be carried out at 240 k resolution and averaging 20 scans. Characterization of the protein sequences will be undertaken by ultraviolet photodissociation (UVPD) using a 193 nm excimer laser (Coherent, Inc.) which will be interfaced to the Orbitrap mass spectrometer as described previously. For each UVPD spectrum, two laser pulses of 2.5 mJ will be used and 250 scans will be averaged. MS1 spectra will be deconvoluted using the Xtract deconvolution algorithm (Thermo Fisher Scientific). UVPD mass spectra will also be deconvoluted using Xtract and then analyzed using ProsightPC 3.0. Proteins containing selenocysteine will be searched by adding a modification of 61.9146 Da to serine residues at the incorporation sites (including the subtraction of one hydrogen atom due to formation of diselenide bonds). Incorporation efficiencies will be calculated by dividing the area of the modified protein peak by the summed areas of the unmodified protein peak and the modified protein peak. The peak area used for each protein will be the sum of the integrated areas of the five most abundant peaks from each isotope cluster.

Example 3—UAG Genomically Recoded Organism Suitable for Expressing Polypeptides with Non-Standard Amino Acids A Genomically Recoded Organism (GRO) in which the UAG codon translational function is completely removed will be used to unambiguously incorporate non-standard amino acids (NSAAs) at UAG. A genomically recoded organism may include one or more reassigned triplet codons to facilitate the incorporation of non-standard amino acids (NSAAa), such as selenocysteine. Triplet codons can be reassigned to incorporate non-standard amino acids, such as selenocysteine, using methods known to those of skill in the art. Alternatively, quadruplet codons can be used to incorporate non-standard amino acids, using methods known to those of skill in the art. An orthogonal aminoacyl-tRNA synthetase (aaRS)/tRNA pair is developed that specifically and efficiently decodes the quadruplet UAGA codon based on the non-functional UAG triplet resulting in unambiguous incorporation of non-standard amino acids, such as selenocysteine, at UAGA codons producing high protein yields. Such quadruplet codons may be used in the present methods.

Example 4—Selection of tRNAs

A method of genetic selection capable of discriminating different levels of selenocysteine incorporation was developed. To specifically 'addict' a reporter protein to selenocysteine rather than serine, the NMC-A β-lactamase from *Enterobacter cloacae* will be used. This enzyme has high sequence similarity to the SME-1 β-lactamase from *Serratia marcescens*, an enzyme that has previously been shown to require a disulfide bond adjacent to the active site serine residue for activity, but that confers a significant fitness cost on *E. coli*. First, a C69S mutant was constructed of NMC-A, which failed to confer resistance to ampicillin (MIC<50 µg/mL), indicating that the disulfide bond was essential for activity. Then cysteine 69 was replaced with an amber stop codon (X69) for library selection, hypothesizing that the incorporation of selenocysteine and the formation of a selenyl-sulfhydryl bond would restore activity.

To eliminate any crosstalk between the tRNASec library and the endogenous selenocysteine incorporation machinery, the selA, selB and selC genes (encoding SelA, SelB and tRNASec respectively) were deleted from *E. coli* DH10B (designated DHΔabc). Cells containing the reporter plasmid pNMC-A C69X and the accessory plasmid pRSF-eSelA (expressing SelA) were transformed with plasmid pMB1-ZU containing the tRNASec antideterminant library. Transformants were plated on media containing a gradient of ampicillin concentrations for selection of mutants capable of selenocysteine-specific suppression. The single colonies that arose covered a range of ampicillin concentrations. Some 12 colonies from each plate were sequenced and revealed three distinct tRNASec mutants:

G7-C66:U49-
G65:C50-U64
(GGAAGAT$\underline{G}^7$GTCGTCTCCGGTGAGGCGGCTGGACTCTAAATCCAGTTGG GGCCGCCAGCGGTCCCGG$\underline{T}^{49}\underline{C}^{50}$AGGTTCGACTCC$\underline{T}^{64}\underline{G}^{65}\underline{C}^{66}$ATCTT

CCGCCA (SEQ ID NO:15)),

C7-G66:U49-G65:C50-U64
(GGAAGAT$\underline{C}^7$GTCGTCTCCGGTGAGGCGGCTGGACTCTAAATCCAGTTGG GGCCGCCAGCGGTCCCGG$\underline{T}^{49}\underline{C}^{50}$AGGTTCGACTCCT$^{64}\underline{G}^{65}\underline{G}^{66}$ATCTT CCGCCA(SEQ ID NO:16))
and C7-U66:U49-A65:A50-A64
(GGAAGAT$\underline{C}^7$GTCGTCTCCGGTGAGGCGGCTGGACTCTAAATCCAGTTGG GGCCGCCAGCGGTCCCGG$\underline{T}^{49}\underline{A}^{50}$AGGTTCGACTCCT$\underline{A}^{65}\underline{T}^{66}$ATCTTC

CGCCA(SEQ ID NO:17))

(where underlined bases represent changes from the parental antideterminant sequence). Of these tRNASec variants, only G7-C66:U49-G65:C50-U64 was detected at the two highest ampicillin concentration (200 and 250 µg/mL).

The tRNASec variant containing the G7-C66:U49-G65: C50-U64 antideterminant sequence was designated tRNASecUx and was compared with the previously designed chimera (tRNAUTu) and with a tRNASec derivative designed to have an antideterminant region that should tightly bind EF-Tu (tRNAUG). The parental tRNASec containing a CUA anticodon and tRNAUG failed to produce active β-lactamase. The hybrid tRNAUTu incorporated selenocysteine and could grow on 75 µg/mL. In contrast, expression of tRNASecUx resulted in significantly higher β-lactamase activity (up to 400 µg/mL), but only when co-expressed with SelA, confirming activity was selenocysteine dependent. To further confirm tRNASecUx incorporated selenocysteine in response to amber stop codons, a standard colorimetric assay was employed based on the activity of the endogenous *E. coli* selenoprotein formate dehydrogenase H (FdhH). FdhH is expressed under anaerobic conditions and catalyzes the oxidation of formate to produce $CO_2$ with the concomitant reduction of the electron acceptor benzyl viologen resulting in the development of a deep purple color. Formate oxidation by FdhH is strictly dependent on the selenocysteine residue at position 140; the mutant FdhH U140S was completely inactive. Only tRNASecUx and tRNAUTu when co-expressed with SelA produced active FdhH.

The selected tRNA contained a non-standard sequence in the junction that normally interacts with EF-Tu. Given that neither the base of the acceptor stem nor the adjoining T-arm base pairs are believed to play a role in the interaction between tRNASec and SelA, the results suggest that the selected U:C leads to stronger binding to EF-Tu than the wild-type tRNASec sequence. The unusual C50-U64 base pair is not predicted to bind strongly to EF-Tu based on models developed for canonical tRNAs, and expression of a hybrid tRNAUG containing the strong EF-Tu binding region from the major *E. coli* tRNAGly did not lead to the production of active β-lactamase, suggesting that the non-standard sequence was functionally important. Thus, it is possible that portions of the engineered tRNASec bind to EF-Tu differently than do canonical tRNAs, which would not necessarily be surprising given that tRNASec normally interacts with SelB.

The development of engineered *E. coli* strains lacking the prfA gene encoding release factor 1 (RF1) has allowed efficient incorporation of a range of unnatural amino acids and the development of the genome-engineered Amberless *E. coli* C321.ΔA provided an excellent opportunity to determine whether proteins that efficiently incorporated selenocysteine could be expressed. The selA, selB and selC genes were deleted in C321.ΔA (designated strain RTΔA), and cells were transformed with the amber-containing NMC-A reporter and accessory plasmids. β-lactamase activity was dramatically increased in RF1-deficient cells compared to prfA+ DHΔabc cells that still contain RF1. In addition, in a RF1-deficient background tRNASecUx could now support the formation of a functional diselenide bond (via amber-mediated incorporation of two selenocysteine residues, U69 and U238).

To further enhance the efficiency of selenocysteine incorporation, a number of steps were taken to improve the levels of Sec-tRNASec relative to Ser-tRNASec, including increasing the level of SelA, decreasing the gene dose of tRNASecUx, and co-expressing a phosphoseryl-tRNASec kinase. To monitor the efficiency of selenocysteine incorporation and demonstrate the possibilities for protein engineering, E. coli dihydrofolate reductase (DHFR) was produced containing an engineered non-essential selenyl-sulfhydryl bond. Top down mass spectrometry showed close to 100% selenocysteine incorporation with no detectable background corresponding to DHFR containing serine. The rationally designed tRNAUTu chimera was also observed to incorporate selenocysteine in DHFR containing a P39X substitution, but resulted in a much lower level of selenocysteine incorporation (38%) and significant serine incorporation (62%). No masses corresponding to the incorporation of other standard amino acids were observed in the mass spectra. In order to further validate selenocysteine incorporation, the *Pseudomonas aeruginosa* metalloprotein azurin was also expressed with its essential cysteine (C112) replaced by selenocysteine and the human selenoprotein cellular glutathione peroxidase (GPx-1). For azurin, this chemical change had previously proven possible only through expressed protein ligation, the essential cysteine could now be biologically replaced with selenocysteine with good efficiency as measured by mass spectrometry of the intact protein.

Example 5—Methods

Strain Construction

The se1AB and se1C genes were deleted from *E. coli* DH10B using the lambda Red system adapted from Datsenko and Wanner (2000). Antibiotic resistance cassettes were excised using FLP recombinase to generate strain DHAabc. Deletion of the entire fdhF open reading frame yielded strain DHAabcF.

*E. coli* C321.ΔA was obtained from Addgene. A ~12 kb genomic region containing lambda phage genes and the TEM-1 3-lactamase inserted during development of the strain was removed to facilitate stable growth at 37° C. and restore sensitivity to 3-lactam antibiotics. Subsequent deletion of the se1AB and se1C genes and excision of antibiotic resistance cassettes generated strain RTΔA. To improve recombinant protein production, deletion of the lon gene encoding the Lon protease and truncation of the rne gene to remove 477 amino acids from the C-terminal of RNase E was performed, resulting in RTΔA.2.

Reporter Plasmids

All reporter plasmids were derived from pcat-pheS. A 3281 bp fragment from pcat-pheS containing the 15A origin of replication and tetA gene conferring tetracycline resistance was ligated to an 1158 bp synthetic DNA fragment containing the b1aSME-1 gene from *Serratia marcescens* encoding the SME-1 3-lactamase flanked by endogenous promoter and terminator sequences. This plasmid (pSME-1) was found to be highly toxic to *E. coli* host cells and was poorly maintained. Replacement of the b1aSME-1 open reading frame with b1aNMC-A from *Enterobacter cloacae* encoding the NMC-A β-lactamase which shares nearly 70% sequence identity with SME-1 generated plasmid pNMC-A which did not exhibit any toxicity. pNMC-A variants with serine or amber codons at residues 69 and 238 were generated by QuikChange site directed mutagenesis.

p15A-fdhF was constructed by ligating the pcat-pheS derived fragment with a 2886 bp fragment amplified from *E. coli* DH10B genomic DNA containing the fdhF gene, the endogenous promoter and terminator sequences and the upstream formate response elements. U140S and U140TAG variants were generated by QuikChange site directed mutagenesis.

Accessory Plasmids

The RSF1030 origin of replication and kan cassette were amplified by PCR as a 1563 bp fragment from pRSFDuet-1 (Novagen). A 1562 bp fragment containing the *E. coli* se1A gene and 5' region covering the endogenous promoter was amplified from *E. coli* DH10B genomic DNA. Assembly of the two fragments yielded plasmid pRSF-Se1A. Replacement of the endogenous weakly active promoter with the strong constitutively active EM7 promoter and a canonical Shine-Dalgarno sequence resulted in plasmid pRSF-eSe1A. Se1A expression plasmids were validated by complementing *E. coli* DH10B deleted for se1A (DHΔa) measured by benzyl viologen assay. Compared to pRSF-Se1A, pRSF-eSe1A induced a strong color change and this variant was used for all further experiments.

pRSF-U-eSe1A was constructed by the addition of NotI and NcoI restriction sites between the RSF1030 origin and se1A promoter and subcloning of the NotI/NcoI fragment containing the se1C gene from pMB1-ZU. pRSF-U-eSe1A variants containing mutant tRNASec genes were constructed by enzymatic inverse PCR. Plasmid pRSF-U-ΔSe1A containing a truncated se1A gene was generated by QuikChange site directed mutagenesis introducing TGA and TAA stop codons at positions 167 and 168 respectively.

Variant tRNA Sequences tRNASecCUA-
(SEQ ID NO: 17)
GGAAGATCGTCGTCTCCGGTGAGGCGGCTGGACTCTAAATCCAGTTGG

GGCCGCCAGCGGTCCCGGGCAGGTTCGACTCCTGTGATCTTCCGCCA.

tRNASecUx-
(SEQ ID NO: 18)
GGAAGATGGTCGTCTCCGGTGAGGCGGCTGGACTCTAAATCCAGTTGG

GGCCGCCAGCGGTCCCGGTCAGGTTCGACTCCTTGCATCTTCCGCCA.

tRNASecUG-
(SEQ ID NO: 19)
GGAAGATGGTCGTCTCCGGTGAGGCGGCTGGACTCTAAATCCAGTTGG

GGCCGCCAGCGGTCCCGGCGAGGTTCGACTCCTCGTATCTTCCGCCA.

tRNAUTu-
(SEQ ID NO: 20)
GGAAGATGTGGCCGAGCGGTTGAAGGCACCGGTCTCTAAAACCGGCGA

CCCGAAAGGGTTCCAGAGTTCGAATCTCTGCATCTTCCGCCA.

Plasmid pRSF-eSe1AK for constitutive expression of both Se1A and PSTK was constructed by insertion of a synthetic DNA fragment between the se1A gene and the kan cassette adding a luxI terminator 3' of se1A and the *Methanocaldococcus jannaschii* pstK gene encoding O-phosphoseryl-tRNASec kinase (PSTK) codon optimized for expression in *E. coli* and flanked by the EM7 promoter and luxI terminator.

Expression Plasmids

Some expression plasmids were derived from pRST.11. For pDHFR-P39X-AU, the wrs1 gene was replaced with an operon controlled by the constitutive EM7 promoter containing the *E. coli* fo1A gene (amplified from DH10B genomic DNA) encoding dihydrofolate reductase with a C-terminal Strep II tag joined by a serine/alanine linker and the se1A gene separated by the sequence TAGGAGGCAGATC (SEQ ID NO: 21) to provide a canonical Shine-Dalgarno sequence. Sc-tRNATrpAmb was replaced by tRNASecUx and tRNAUTu to express the tRNASec variants from the strong leuP promoter. TAG and AGC codons were introduced at position 39 by QuikChange site directed mutagenesis. pAz-C112X-AU was constructed similarly replacing the fo1A gene with a synthetic DNA fragment containing the azu gene from *Pseudomonas aeruginosa* encoding azurin codon optimized for expression in *E. coli* with a C-terminal His6-tag. TAG and AGC codons were introduced at position 112 by QuikChange site directed mutagenesis. pGPx-U49-AU was constructed by replacing the fo1A gene with a synthetic DNA fragment containing the human gpx1 gene encoding cellular glutathione peroxidase (GPx-1) codon optimized for expression in *E. coli* with an N-terminal His6-tag.

Library Construction and Selection

A 1518 bp fragment encompassing the MB1 origin of replication and rop gene was amplified from pETDuet-1 (Novagen). This was assembled with a synthetic DNA fragment containing a codon optimized ble gene from *Streptoalloteichus hindustans* conferring Zeocin resistance flanked by the EM7 promoter and the endogenous terminator sequence and a MCS including NotI and NcoI sites to generate plasmid pMB1-Z. A 410 bp fragment including the selC gene and its promoter was amplified from *E. coli* DH10B genomic DNA with flanking NotI and NcoI sites and ligated into pMB1-Z to construct pMB1-ZU. Functionality of the selC gene was confirmed by complementing *E. coli* DH10B deleted for selC (DHAc) as measured by benzyl viologen assay.

The tRNASec antideterminant library was generated by enzymatic inverse PCR using oligonucleotide primers to randomize the six positions identified as the main antideterminant for EF-Tu binding. Following self ligation for 16 hours, DNA was ethanol precipitated with GlycoBlue (Ambion) and transformed by electroporation into *E. coli* DHAabc containing the plasmids pNMC-A C69X and pRSF-eSe1A. Transformants were diluted in 200 ml LB medium containing 12.5 µg/mL Zeocin, 6.25 µg/mL tetracycline and 25 µg/mL kanamycin and incubated overnight. Following overnight growth, cells were diluted 1/50 in LB medium containing 6.25 µg/mL Zeocin, 3.75 µg/mL tetracycline, 12.5 µg/mL kanamycin, 1 µM Na2SeO3 and 20 µg/mL L-cysteine and incubated for one hour. A series of 250 µl aliquots of cells were plated on LB agar containing 6.25 µg/mL Zeocin, 3.75 µg/mL tetracycline, 12.5 µg/mL kanamycin, 1 µM Na2SeO3 and 20 µg/mL L-cysteine and 50-300 µg/mL ampicillin in 50 µg/mL increments. After 20 hours at 37° C. individual colonies were observed on plates containing 50-200 µg/mL ampicillin. Plasmid DNA was isolated from a selection of colonies from all plates and tRNASec mutations determined by Sanger sequencing.

Primer Sequences—Oligonucleotide Primers for Library Construction.

selClibfwd-
(SEQ ID NO: 22)
TGGACTGGTCTCCCAGTTGGGGCCGCCAGCGGTCCCGGNNAGGTTCGACT

CCTNNNATCTTCCGCCAAAATGC.

selClibrev-
(SEQ ID NO: 23)
GCTGGCGGTCTCaACTGGATTTAGAGTCCAGCCGCCTCACCGGAGACGAC

NATCTTCCGCGCCTCG.

Rephenotyping

NotI/NcoI fragments containing tRNASecUx were subcloned into pRSF-eSe1A to generate pRSF-UX-eSe1A. pRSF-U-eSe1A variants were transformed into *E. coli* DHAabc containing the reporter plasmid pNMC-A C69TAG. DHAabc cells containing pNMC-A and pRSF-Duet-1 were used as a positive control. DHAabc cells harboring pNMC-A C69S and pRSF-UX-eSe1A, and pNMC-A C69TAG and pRSF-UX-ASe1A were used as controls for selenocysteine dependent f1-lactamase activity. Transformants were cultured overnight in LB medium containing 6.25 pg/mL tetracycline, 25 pg/mL kanamycin, 1 pM Na2SeO3 and 20 pg/mL L-cysteine. Following overnight growth, cells were diluted 1/10 in LB medium containing antibiotics, selenite and L-cysteine and incubated for three hours. Cultures were normalized to OD600=0.1 and 5 pl aliquots plated in triplicate on LB agar containing 3.75 pg/mL tetracycline, 12.5 pg/mL kanamycin, 1 pM Na2SeO3, 20 pg/mL L-cysteine and a gradient of ampicillin spanning 0, 10, 25, 50, 75, 100, 150, 200, 250, 300, 350, 400, 450 and 500 pg/mL. Plates were incubated at 37° C. overnight. Identical assay conditions were used to repeat this experiment with *E. coli* RTΔA.

Benzyl Viologen Assay

*E. coli* DH10B cells containing pRSFDuet-1 and pcat-pheS were used as a positive control. DHAabcF cells harboring p15A-fdhF U140S and pRSF-UX-eSe1A, and p15A-fdhF U140X and pRSF-UX-ASe1A were used as controls for selenocysteine dependent formate dehydrogenase activity. Transformants were grown overnight at 37° C. in LB medium supplemented with 12.5 pg/mL tetracycline and 50 pg/mL kanamycin. Overnight cultures were diluted 1/20 in a final volume of 2 ml and incubated for three hours. Cultures were normalized to OD600=0.5 and 5 pl aliquots were dotted on LB agar plates containing 3.75 pg/mL tetracycline, 12.5 pg/mL kanamycin, 5 mM sodium formate, 10 pM Na2MoO4, 1 pM Na2SeO3 and 20 pg/mL L-cysteine. Plates were incubated at 37° C. for 3 h under aerobic conditions and then transferred to anaerobic conditions at 37° C. for 60 h. Upon removal from the anaerobic chamber, plates were immediately overlaid with agar containing 1 mg/mL benzyl viologen, 250 mM sodium formate and 25 mM KH2PO4 at pH 7.0. Plates were photographed within 1 h of overlaying.

Modifications and Protein Purification

Initial attempts to produce selenoproteins in *E. coli* strain RTΔA.2 used an accessory plasmid derived from pRSF-UX-eSe1A in which the endogenous selC promoter was replaced with the highly active *E. coli* leuP promoter in combination with an expression plasmid containing the azu gene downstream of the strong tad promoter. Mass spectrometry of the initial selenoprotein samples revealed almost exclusive incorporation of serine at the amber codon and a number of optimizations were made to increase the ratio of Sec-tRNASec to Ser-tRNASec, thought to be the main driver of incorporation efficiency. To increase the Se1A to tRNASec ratio, expression of tRNASec variants was reduced by shifting the leuP cassette to the lower copy expression plasmid containing the MB1 origin of replication and adding a second selA gene downstream of the target selenoprotein. In addition, to prevent rapid depletion of the Sec-tRNASec pool following induction, the tacI promoter driving selenoprotein expression was replaced by the constitutive EM7 promoter. These changes generated expression plasmids pDHFR-P39X-AU and pAz-C112X-AU.

To further reduce the pool of Ser-tRNASec available to participate in canonical translation, the pstK gene encoding O-phosphoseryl-tRNASec kinase was added to the accessory plasmid pRSF-eSe1A to yield pRSF-eSe1AK. PSTK has previously been reported to increase selenocysteine incorporation with tRNAUTu by generating Sep-tRNASec, an efficient substrate for Se1A but poorly recognized by *E.*

*coli* EF-Tu. In conjunction, the selenium concentration in the medium was increased and L-cysteine omitted for selenoprotein production.

RTΔA.2 transformants containing pDHFR-P39X-AU and pRSF-eSe1AK were cultured O/N in LB medium containing 100 μg/mL ampicillin, 50 μg/mL kanamycin and 1 μM Na2SeO3. Overnight cultures were diluted 1/500 in a final volume of 2 L LB medium containing 50 μg/mL ampicillin, 25 μg/mL kanamycin and 5 μM Na2SeO3 and incubated with agitation for 24 hours at 37° C. Cells were harvested by centrifugation at 8000×g for 10 min and resuspended in 20 mL of wash buffer (100 mM Tris, 150 mM NaCl, 1 mM EDTA at pH 8.0) with protease inhibitor cocktail (cOmplete, mini EDTA free, Roche) and lysozyme at 1 mg/mL. Following a 20 min incubation at 4° C. cells were lysed by sonication (Model 500, Fisher Scientific) and clarified by three times by centrifugation at 35000×g for 30 min. Lysate was passed through a 0.2 μm filter and seleno-DHFR recovered using Strep-Tactin affinity chromatography following the manufacturer's instructions (GE Healthcare). Eluate was concentrated to 3 mL and dialyzed against 50 mM NH4Ac pH 6.5 prior to the isolation of seleno-DHFR by size exclusion FPLC (ÄKTA, GE Healthcare). Seleno-DHFR was produced using tRNASecUx with a yield of 68 μg/L and 100% incorporation efficiency. Seleno-DHFR was produced using tRNAUTu with a yield of 131 μg/L and 38.1% incorporation efficiency. DHFR containing serine at position 39 was produced with a yield of 225 μg/L.

RTΔA.2 transformants containing pAz-C112X-AU and pRSF-eSe1AK were cultured as described previously with the exception that 20 μM Na2SeO3 was added for the 24 hour incubation. Cells were harvested by centrifugation and the periplasmic fraction isolated. Briefly, cell pellets were resuspended in 50 mL of 100 mM Tris and 0.75 M sucrose at pH 7.5. Following addition of lysozyme to 1 mg/mL and protease inhibitor cocktail cells were gently agitated for 20 min at 4° C. 50 mL of 1 mM EDTA was added and samples incubated again for 20 minutes. EDTA was neutralized by addition of 3.5 mL 0.5M MgCl2 during a further 20 min incubation. Spheroblasts were removed by centrifugation at 35000×g for 30 min, the periplasmic fraction passed through a 0.2 μm filter and mixed with imidazole stock solution to a final concentration of 20 mM. Seleno-azurin was recovered by IMAC using Ni-NTA resin and gravity flow columns. Eluate was concentrated and dialyzed against 50 mM NH4Ac pH 6.5 prior to the isolation of seleno-azurin by size exclusion FPLC. Seleno-azurin was produced using tRNASecUx with a yield of 50 μg/L and greater than 76% incorporation efficiency. This value likely under represents the actual level of selenocysteine incorporation as seleno-azurin was observed to form higher molecular weight complexes during and after purification, resulting in loss during size exclusion chromatography. No aggregation was observed for azurin samples containing only serine.

RTΔA.2 transformants containing pGPx-U49-AU and pRSF-eSe1AK were cultured as described previously for azurin. Cells were harvested by centrifugation and resuspended in 50 mL of buffer (50 mM Potassium Phosphate, 150 mM NaCl, 10% glycerol, 1 mM DTT at pH 8.0) and lysozyme at 1 mg/mL. Cells were lysed by sonication and clarified prior to GPx-1 recovery by IMAC. Eluate was concentrated and dialyzed against 100 mM phosphate buffer pH 8.0, 0.1% Tween 20 and 1 mM DTT followed by isolation of GPx-1 by anion exchange chromatography (Q HP column). GPx-1 was produced with a yield of 500 μg/L and close to 100% selenocysteine incorporation efficiency.

Mass Spectrometry

Intact protein samples will be analyzed using methods described previously. Azurin, DHFR and GPx-1 samples were buffer exchanged into LC-MS grade water using 10 kDa molecular weight cutoff filters. Once the buffer exchange was complete the samples were diluted to 20 μM in a methanol/water/formic acid (50/49/1) solution. After dilution, protein solutions were infused into an Orbitrap Elite mass spectrometer (Thermo Fisher Scientific Instruments, Bremen, Germany) at a rate of 3 μL/min via electrospray ionization. In order to confirm the incorporation of selenocysteine, intact mass analysis was carried out at 240 k resolution and averaging 20 scans. Characterization of the protein sequences was undertaken by ultraviolet photodissociation (UVPD) using a 193 nm excimer laser (Coherent, Inc.) which was interfaced to the Orbitrap mass spectrometer as described previously. For each UVPD spectrum, two laser pulses of 2.5 mJ were used and 250 scans were averaged. MS1 spectra were deconvoluted using the Xtract deconvolution algorithm (Thermo Fisher Scientific). UVPD mass spectra were also deconvoluted using Xtract and then analyzed using ProsightPC 3.0. Proteins containing selenocysteine were searched by adding a modification of 62.9216 Da to the serine at position 112 for azurin or 61.9146 Da for the serine at position 39 for DHFR (with subtraction of one hydrogen atom from the DHFR modification because a selenyl-sulfhydryl bond is formed when selenocysteine is present). Incorporation efficiencies were calculated by dividing the area of the modified protein peak by the summed areas of the unmodified protein peak and the modified protein peak. The peak area used for each protein was the sum of the integrated areas of the five most abundant peaks from each isotope cluster.

Example 6—DNase I Activity

A fluorescently labeled probe as part of an assay for the DNase I activity is prepared by amplification. Amplification is performed in a reaction mixture containing plasmid DNA, DNA Polymerase, amplification Buffer, each type of deoxynucleoside triphosphate (dNTP), and primers. The amplification is performed under the following conditions: initial denaturation at 94° C. for 5 minutes, 35 cycles of 94° C. for 1 minute, 55° C. for 1 minute, and 72° C. for 1 minute, with the final elongation step at 72° C. for 10 minutes. The obtained PCR product is purified using the GeneJET PCR Purification Kit (ThermoFisher Scientific, Waltham, Mass.).

Activity of DNase I is determined by incubation of the samples with fluorescently labeled PCR fragments, followed by detection of fluorescently labeled products by capillary electrophoresis on an Applied Biosystems 3130 Genetic Analyzer (Applied Biosystems Corporation, Carlsbad, Calif.). The assay is performed in a reaction mixture containing PCR product and the sample 10× diluted in saline. The negative control contains only the labeled fragment, with no source of DNase I activity. The reaction mixture is incubated for 2 minutes at room temperature, after which the reaction is stopped by incubation at 75° C. for 10 minutes. The reaction mixtures are purified using the GeneJET PCR Purification Kit (ThermoFisher Scientific). Each sample subjected to fragment analysis. Capillary electrophoresis is performed with POP-7 Polymer (Applied Biosystems Corporation), using the default genotyping module for the G5 dye set. The results were analyzed using the GeneMapper Software, version 4.0 (Applied Biosystems Corporation). DNase activities of the samples are expressed as percentage differences of signal intensity compared with control material containing no DNase, which was assigned the value of 1 (100%).

Example 7—DNase I Activity 30 ng of seleno-DNase (GST-seleno-DNase I fusion) and equimolar disulfide DNase (wild-type DNase I purified from bovine pancreas, Sigma DN25) were incubated for 2 hours at 37° C. in reaction buffer (NEB B0303S) supplemented with either 0 mM DTT (−DTT) or 50 mM DTT (+DTT). 50 ng double stranded DNA was added to the mixture and digested for 30 min at 37 C followed by 10 min of heat inactivation at 75° C. Both enzymes digested the DNA in 0 mM DTT but only seleno-DNase digested the DNA in 50 mM DTT (FIG. 1).

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A composition comprising a deoxyribonuclease I (DNase I) polypeptide comprising at least 90% sequence identity to at least 225 contiguous amino acids of the polypeptide of SEQ ID NO: 1, wherein the DNase I polypeptide comprises from two to four selenocysteines, wherein at least two of said selenocysteines are located at positions selected from the group consisting of:
   (a) a position corresponding to position 102 of the polypeptide of SEQ ID NO:1,
   (b) a position corresponding to position 105 of the polypeptide of SEQ ID NO:1,
   (c) a position corresponding to position 174 of the polypeptide of SEQ ID NO:1, and
   (d) a position corresponding to position 210 of the polypeptide of SEQ ID NO:1; and
   wherein the DNase I polypeptide comprises a first pair of selenocysteines linked by a first diselenide bond.

2. The composition of claim 1, wherein the DNase I polypeptide further comprises a second pair of selenocysteines linked by a second diselenide bond.

3. The composition of claim 1, wherein the DNase I polypeptide comprises a sequence with at least 95% sequence identity to at least 225 contiguous amino acids of the polypeptide of SEQ ID NO: 1.

4. The composition of claim 1, wherein the DNase I polypeptide has at least 90% identity to the polypeptide of SEQ ID NO: 1.

5. The composition claim 1, wherein the DNase I polypeptide comprises four selenocysteines, wherein the four selenocysteines are located at the following positions:
   (a) a position corresponding to position 102 of the polypeptide of SEQ ID NO:1,
   (b) a position corresponding to position 105 of the polypeptide of SEQ ID NO:1,
   (c) a position corresponding to position 174 of the polypeptide of SEQ ID NO:1, and
   (d) a position corresponding to position 210 of the polypeptide of SEQ ID NO:1.

6. The composition of claim 1, wherein the DNase I polypeptide comprises a selenocysteine at a position corresponding to position 102 of the polypeptide of SEQ ID NO:1 linked by a diselenide bond to a selenocysteine at a position corresponding to position 105 of the polypeptide of SEQ ID NO:1.

7. The composition of claim 1, wherein the DNase I polypeptide comprises a selenocysteine at a position corresponding to position 174 of the polypeptide of SEQ ID NO:1 linked by a diselenide bond to a selenocysteine at a position corresponding to position 210 of the polypeptide of SEQ ID NO:1.

8. The composition of claim 1, wherein the DNase I polypeptide is recombinant.

9. The composition of claim 1, wherein the DNase I polypeptide is a modified bovine DNase I.

10. A bacterial cell comprising the composition of claim 1.

11. The composition of claim 3, wherein the DNase I polypeptide has at least 96% sequence identity to at least 225 contiguous amino acids of the polypeptide of SEQ ID NO:1.

12. The composition of claim 3, wherein the DNase I polypeptide has at least 97% sequence identity to at least 225 contiguous amino acids of the polypeptide of SEQ ID NO:1.

13. The composition of claim 3, wherein the DNase I polypeptide has at least 98% sequence identity to at least 225 contiguous amino acids of the polypeptide of SEQ ID NO:1.

14. The composition of claim 3, wherein the DNase I polypeptide has at least 99% sequence identity to at least 225 contiguous amino acids of the polypeptide of SEQ ID NO:1.

15. The composition of claim 4, wherein the DNase I polypeptide has at least 95% sequence identity to the polypeptide of SEQ ID NO:1.

16. The composition of claim 4, wherein the DNase I polypeptide has at least 97% sequence identity to the polypeptide of SEQ ID NO:1.

17. The composition of claim 4, wherein the DNase I polypeptide has at least 98% sequence identity to the polypeptide of SEQ ID NO:1.

18. The composition of claim 4, wherein the DNase I polypeptide has at least 99% sequence identity to the polypeptide of SEQ ID NO:1.

* * * * *

SEQUENCE LISTING

```
<160> NUMBER OF SEQ ID NOS: 27

<210> SEQ ID NO 1
<211> LENGTH: 261
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (102)..(102)
<223> OTHER INFORMATION: Non-standard amino acid
<220> FEATURE:
<221> NAME/KEY: MOD_RES
<222> LOCATION: (105)..(105)
<223> OTHER INFORMATION: Non-standard amino acid
<220> FEATURE:
<221> NAME/KEY: MOD_RES
<222> LOCATION: (174)..(174)
<223> OTHER INFORMATION: Non-standard amino acid
<220> FEATURE:
<221> NAME/KEY: MOD_RES
<222> LOCATION: (210)..(210)
<223> OTHER INFORMATION: Non-standard amino acid
<220> FEATURE:
<223> OTHER INFORMATION: See specification as filed for detailed
      description of substitutions and preferred embodiments

<400> SEQUENCE: 1

Ala Leu Lys Ile Ala Ala Phe Asn Ile Arg Thr Phe Gly Glu Thr Lys
1               5                   10                  15

Met Ser Asn Ala Thr Leu Ala Ser Tyr Ile Val Arg Ile Val Arg Arg
            20                  25                  30

Tyr Asp Ile Val Leu Ile Gln Glu Val Arg Asp Ser His Leu Val Ala
        35                  40                  45

Val Gly Lys Leu Leu Asp Tyr Leu Asn Gln Asp Pro Asn Thr Tyr
    50                  55                  60

His Tyr Val Val Ser Glu Pro Leu Gly Arg Asn Ser Tyr Lys Glu Arg
65                  70                  75                  80

Tyr Leu Phe Leu Phe Arg Pro Asn Lys Val Ser Val Leu Asp Thr Tyr
                85                  90                  95

Gln Tyr Asp Asp Gly Xaa Glu Ser Xaa Gly Asn Asp Ser Phe Ser Arg
            100                 105                 110

Glu Pro Ala Val Val Lys Phe Ser Ser His Ser Thr Lys Val Lys Glu
        115                 120                 125

Phe Ala Ile Val Ala Leu His Ser Ala Pro Ser Asp Ala Val Ala Glu
    130                 135                 140

Ile Asn Ser Leu Tyr Asp Val Tyr Leu Asp Val Gln Gln Lys Trp His
```

```
        145                 150                 155                 160
Leu Asn Asp Val Met Leu Met Gly Asp Phe Asn Ala Asp Xaa Ser Tyr
                165                 170                 175

Val Thr Ser Ser Gln Trp Ser Ser Ile Arg Leu Arg Thr Ser Ser Thr
                180                 185                 190

Phe Gln Trp Leu Ile Pro Asp Ser Ala Asp Thr Thr Ala Thr Ser Thr
                195                 200                 205

Asn Xaa Ala Tyr Asp Arg Ile Val Val Ala Gly Ser Leu Leu Gln Ser
            210                 215                 220

Ser Val Val Pro Gly Ser Ala Ala Pro Phe Asp Phe Gln Ala Ala Tyr
225                 230                 235                 240

Gly Leu Ser Asn Glu Met Ala Leu Ala Ile Ser Asp His Tyr Pro Val
                245                 250                 255

Glu Val Thr Leu Thr
            260

<210> SEQ ID NO 2
<211> LENGTH: 281
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Arg Gly Thr Arg Leu Met Gly Leu Leu Ala Leu Ala Gly Leu Leu
1               5                   10                  15

Gln Leu Gly Leu Ser Leu Lys Ile Ala Ala Phe Asn Ile Arg Thr Phe
                20                  25                  30

Gly Glu Thr Lys Met Ser Asn Ala Thr Leu Ala Ser Tyr Ile Val Arg
            35                  40                  45

Ile Val Arg Arg Tyr Asp Ile Val Leu Ile Gln Glu Val Arg Asp Ser
        50                  55                  60

His Leu Val Ala Val Gly Lys Leu Leu Asp Tyr Leu Asn Gln Asp Asp
65                  70                  75                  80

Pro Asn Thr Tyr His Tyr Val Val Ser Glu Pro Leu Gly Arg Asn Ser
                85                  90                  95

Tyr Lys Glu Arg Tyr Leu Phe Leu Phe Arg Pro Asn Lys Val Ser Val
            100                 105                 110

Leu Asp Thr Tyr Gln Tyr Asp Asp Gly Cys Glu Ser Cys Gly Asn Asp
        115                 120                 125

Ser Phe Ser Arg Glu Pro Ala Val Val Lys Phe Ser Ser His Ser Thr
130                 135                 140

Lys Val Lys Glu Phe Ala Ile Val Ala Leu His Ser Ala Pro Ser Asp
145                 150                 155                 160

Ala Val Ala Glu Ile Asn Ser Leu Tyr Asp Val Tyr Leu Asp Val Gln
                165                 170                 175

Gln Lys Trp His Leu Asn Asp Val Met Leu Met Gly Asp Phe Asn Ala
            180                 185                 190

Asp Cys Ser Tyr Val Thr Ser Ser Gln Trp Ser Ser Ile Arg Leu Arg
        195                 200                 205

Thr Ser Ser Thr Phe Gln Trp Leu Ile Pro Asp Ser Ala Asp Thr Thr
    210                 215                 220

Ala Thr Ser Thr Asn Cys Ala Tyr Asp Arg Ile Val Val Ala Gly Ser
225                 230                 235                 240
```

```
Leu Leu Gln Ser Ser Val Val Pro Gly Ser Ala Ala Pro Phe Asp Phe
                245                 250                 255

Gln Ala Ala Tyr Gly Leu Ser Asn Glu Met Ala Leu Ala Ile Ser Asp
            260                 265                 270

His Tyr Pro Val Glu Val Thr Leu Thr
        275                 280

<210> SEQ ID NO 3
<211> LENGTH: 487
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (328)..(328)
<223> OTHER INFORMATION: Non-standard amino acid
<220> FEATURE:
<221> NAME/KEY: MOD_RES
<222> LOCATION: (331)..(331)
<223> OTHER INFORMATION: Non-standard amino acid
<220> FEATURE:
<221> NAME/KEY: MOD_RES
<222> LOCATION: (400)..(400)
<223> OTHER INFORMATION: Non-standard amino acid
<220> FEATURE:
<221> NAME/KEY: MOD_RES
<222> LOCATION: (436)..(436)
<223> OTHER INFORMATION: Non-standard amino acid
<220> FEATURE:
<223> OTHER INFORMATION: See specification as filed for detailed
      description of substitutions and preferred embodiments

<400> SEQUENCE: 3

Met Ser Pro Ile Leu Gly Tyr Trp Lys Ile Lys Gly Leu Val Gln Pro
1               5                   10                  15

Thr Arg Leu Leu Leu Glu Tyr Leu Glu Glu Lys Tyr Glu Glu His Leu
            20                  25                  30

Tyr Glu Arg Asp Glu Gly Asp Lys Trp Arg Asn Lys Lys Phe Glu Leu
        35                  40                  45

Gly Leu Glu Phe Pro Asn Leu Pro Tyr Tyr Ile Asp Gly Asp Val Lys
    50                  55                  60

Leu Thr Gln Ser Met Ala Ile Ile Arg Tyr Ile Ala Asp Lys His Asn
65                  70                  75                  80

Met Leu Gly Gly Cys Pro Lys Glu Arg Ala Glu Ile Ser Met Leu Glu
                85                  90                  95

Gly Ala Val Leu Asp Ile Arg Tyr Gly Val Ser Arg Ile Ala Tyr Ser
            100                 105                 110

Lys Asp Phe Glu Thr Leu Lys Val Asp Phe Leu Ser Lys Leu Pro Glu
        115                 120                 125

Met Leu Lys Met Phe Glu Asp Arg Leu Cys His Lys Thr Tyr Leu Asn
    130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
            180                 185                 190

Leu Lys Ser Ser Lys Tyr Ile Ala Trp Pro Leu Gln Gly Trp Gln Ala
        195                 200                 205

Thr Phe Gly Gly Gly Asp His Pro Pro Lys Ser Asp Gly Gly Ser Gly
```

```
                210                 215                 220
Ser Ala Ala Leu Lys Ile Ala Ala Phe Asn Ile Arg Thr Phe Gly Glu
225                 230                 235                 240

Thr Lys Met Ser Asn Ala Thr Leu Ala Ser Tyr Ile Val Arg Ile Val
            245                 250                 255

Arg Arg Tyr Asp Ile Val Leu Ile Gln Glu Val Arg Asp Ser His Leu
        260                 265                 270

Val Ala Val Gly Lys Leu Leu Asp Tyr Leu Asn Gln Asp Asp Pro Asn
    275                 280                 285

Thr Tyr His Tyr Val Val Ser Glu Pro Leu Gly Arg Asn Ser Tyr Lys
290                 295                 300

Glu Arg Tyr Leu Phe Leu Phe Arg Pro Asn Lys Val Ser Val Leu Asp
305                 310                 315                 320

Thr Tyr Gln Tyr Asp Asp Gly Xaa Glu Ser Xaa Gly Asn Asp Ser Phe
            325                 330                 335

Ser Arg Glu Pro Ala Val Val Lys Phe Ser His Ser Thr Lys Val
        340                 345                 350

Lys Glu Phe Ala Ile Val Ala Leu His Ser Ala Pro Ser Asp Ala Val
    355                 360                 365

Ala Glu Ile Asn Ser Leu Tyr Asp Val Tyr Leu Asp Val Gln Gln Lys
370                 375                 380

Trp His Leu Asn Asp Val Met Leu Met Gly Asp Phe Asn Ala Asp Xaa
385                 390                 395                 400

Ser Tyr Val Thr Ser Ser Gln Trp Ser Ser Ile Arg Leu Arg Thr Ser
            405                 410                 415

Ser Thr Phe Gln Trp Leu Ile Pro Asp Ser Ala Asp Thr Thr Ala Thr
        420                 425                 430

Ser Thr Asn Xaa Ala Tyr Asp Arg Ile Val Val Ala Gly Ser Leu Leu
    435                 440                 445

Gln Ser Ser Val Val Pro Gly Ser Ala Ala Pro Phe Asp Phe Gln Ala
450                 455                 460

Ala Tyr Gly Leu Ser Asn Glu Met Ala Leu Ala Ile Ser Asp His Tyr
465                 470                 475                 480

Pro Val Glu Val Thr Leu Thr
            485

<210> SEQ ID NO 4
<211> LENGTH: 307
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (102)..(102)
<223> OTHER INFORMATION: Non-standard amino acid
<220> FEATURE:
<221> NAME/KEY: MOD_RES
<222> LOCATION: (105)..(105)
<223> OTHER INFORMATION: Non-standard amino acid
<220> FEATURE:
<221> NAME/KEY: MOD_RES
<222> LOCATION: (174)..(174)
<223> OTHER INFORMATION: Non-standard amino acid
<220> FEATURE:
<221> NAME/KEY: MOD_RES
<222> LOCATION: (210)..(210)
<223> OTHER INFORMATION: Non-standard amino acid
<220> FEATURE:
<223> OTHER INFORMATION: See specification as filed for detailed
``` description of substitutions and preferred embodiments

<400> SEQUENCE: 4

Ala Leu Lys Ile Ala Ala Phe Asn Ile Arg Thr Phe Gly Glu Thr Lys
1               5                   10                  15

Met Ser Asn Ala Thr Leu Ala Ser Tyr Ile Val Arg Ile Val Arg Arg
            20                  25                  30

Tyr Asp Ile Val Leu Ile Gln Glu Val Arg Asp Ser His Leu Val Ala
        35                  40                  45

Val Gly Lys Leu Leu Asp Tyr Leu Asn Gln Asp Pro Asn Thr Tyr
    50                  55                  60

His Tyr Val Val Ser Glu Pro Leu Gly Arg Asn Ser Tyr Lys Glu Arg
65                  70                  75                  80

Tyr Leu Phe Leu Phe Arg Pro Asn Lys Val Ser Val Leu Asp Thr Tyr
                85                  90                  95

Gln Tyr Asp Asp Gly Xaa Glu Ser Xaa Gly Asn Asp Ser Phe Ser Arg
            100                 105                 110

Glu Pro Ala Val Val Lys Phe Ser Ser His Ser Thr Lys Val Lys Glu
        115                 120                 125

Phe Ala Ile Val Ala Leu His Ser Ala Pro Ser Asp Ala Val Ala Glu
130                 135                 140

Ile Asn Ser Leu Tyr Asp Val Tyr Leu Asp Val Gln Gln Lys Trp His
145                 150                 155                 160

Leu Asn Asp Val Met Leu Met Gly Asp Phe Asn Ala Asp Xaa Ser Tyr
                165                 170                 175

Val Thr Ser Ser Gln Trp Ser Ser Ile Arg Leu Arg Thr Ser Ser Thr
            180                 185                 190

Phe Gln Trp Leu Ile Pro Asp Ser Ala Asp Thr Thr Ala Thr Ser Thr
        195                 200                 205

Asn Xaa Ala Tyr Asp Arg Ile Val Val Ala Gly Ser Leu Leu Gln Ser
    210                 215                 220

Ser Val Val Pro Gly Ser Ala Ala Pro Phe Asp Phe Gln Ala Ala Tyr
225                 230                 235                 240

Gly Leu Ser Asn Glu Met Ala Leu Ala Ile Ser Asp His Tyr Pro Val
                245                 250                 255

Glu Val Thr Leu Thr Gly Ser His His His His His Gly Ser Gly
            260                 265                 270

Gly Gly Ser Gly Gly Ser Ala Trp Ser His Pro Gln Phe Glu Lys Gly
        275                 280                 285

Gly Gly Ser Gly Gly Gly Ser Gly Gly Ser Ala Trp Ser His Pro Gln
    290                 295                 300

Phe Glu Lys
305

<210> SEQ ID NO 5
<211> LENGTH: 533
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (328)..(328)
<223> OTHER INFORMATION: Non-standard amino acid
<220> FEATURE:
<221> NAME/KEY: MOD_RES
<222> LOCATION: (331)..(331)

```
<223> OTHER INFORMATION: Non-standard amino acid
<220> FEATURE:
<221> NAME/KEY: MOD_RES
<222> LOCATION: (400)..(400)
<223> OTHER INFORMATION: Non-standard amino acid
<220> FEATURE:
<221> NAME/KEY: MOD_RES
<222> LOCATION: (436)..(436)
<223> OTHER INFORMATION: Non-standard amino acid
<220> FEATURE:
<223> OTHER INFORMATION: See specification as filed for detailed
      description of substitutions and preferred embodiments

<400> SEQUENCE: 5

Met Ser Pro Ile Leu Gly Tyr Trp Lys Ile Lys Gly Leu Val Gln Pro
1               5                   10                  15

Thr Arg Leu Leu Leu Glu Tyr Leu Glu Glu Lys Tyr Glu Glu His Leu
            20                  25                  30

Tyr Glu Arg Asp Glu Gly Asp Lys Trp Arg Asn Lys Lys Phe Glu Leu
        35                  40                  45

Gly Leu Glu Phe Pro Asn Leu Pro Tyr Tyr Ile Asp Gly Asp Val Lys
50                  55                  60

Leu Thr Gln Ser Met Ala Ile Ile Arg Tyr Ile Ala Asp Lys His Asn
65                  70                  75                  80

Met Leu Gly Gly Cys Pro Lys Glu Arg Ala Glu Ile Ser Met Leu Glu
                85                  90                  95

Gly Ala Val Leu Asp Ile Arg Tyr Gly Val Ser Arg Ile Ala Tyr Ser
            100                 105                 110

Lys Asp Phe Glu Thr Leu Lys Val Asp Phe Leu Ser Lys Leu Pro Glu
        115                 120                 125

Met Leu Lys Met Phe Glu Asp Arg Leu Cys His Lys Thr Tyr Leu Asn
130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
            180                 185                 190

Leu Lys Ser Ser Lys Tyr Ile Ala Trp Pro Leu Gln Gly Trp Gln Ala
        195                 200                 205

Thr Phe Gly Gly Gly Asp His Pro Pro Lys Ser Asp Gly Gly Ser Gly
210                 215                 220

Ser Ala Ala Leu Lys Ile Ala Ala Phe Asn Ile Arg Thr Phe Gly Glu
225                 230                 235                 240

Thr Lys Met Ser Asn Ala Thr Leu Ala Ser Tyr Ile Val Arg Ile Val
                245                 250                 255

Arg Arg Tyr Asp Ile Val Leu Ile Gln Glu Val Arg Asp Ser His Leu
            260                 265                 270

Val Ala Val Gly Lys Leu Leu Asp Tyr Leu Asn Gln Asp Asp Pro Asn
        275                 280                 285

Thr Tyr His Tyr Val Val Ser Glu Pro Leu Gly Arg Asn Ser Tyr Lys
290                 295                 300

Glu Arg Tyr Leu Phe Leu Phe Arg Pro Asn Lys Val Ser Val Leu Asp
305                 310                 315                 320

Thr Tyr Gln Tyr Asp Asp Gly Xaa Glu Ser Xaa Gly Asn Asp Ser Phe
            325                 330                 335

Ser Arg Glu Pro Ala Val Val Lys Phe Ser Ser His Ser Thr Lys Val
```

-continued

```
                  340                 345                 350
Lys Glu Phe Ala Ile Val Ala Leu His Ser Ala Pro Ser Asp Ala Val
            355                 360                 365

Ala Glu Ile Asn Ser Leu Tyr Asp Val Tyr Leu Asp Val Gln Gln Lys
        370                 375                 380

Trp His Leu Asn Asp Val Met Leu Met Gly Asp Phe Asn Ala Asp Xaa
385                 390                 395                 400

Ser Tyr Val Thr Ser Ser Gln Trp Ser Ser Ile Arg Leu Arg Thr Ser
                405                 410                 415

Ser Thr Phe Gln Trp Leu Ile Pro Asp Ser Ala Asp Thr Thr Ala Thr
            420                 425                 430

Ser Thr Asn Xaa Ala Tyr Asp Arg Ile Val Val Ala Gly Ser Leu Leu
        435                 440                 445

Gln Ser Ser Val Val Pro Gly Ser Ala Ala Pro Phe Asp Phe Gln Ala
    450                 455                 460

Ala Tyr Gly Leu Ser Asn Glu Met Ala Leu Ala Ile Ser Asp His Tyr
465                 470                 475                 480

Pro Val Glu Val Thr Leu Thr Gly Ser His His His His His His Gly
                485                 490                 495

Ser Gly Gly Gly Ser Gly Gly Ser Ala Trp Ser His Pro Gln Phe Glu
            500                 505                 510

Lys Gly Gly Gly Ser Gly Gly Ser Gly Gly Ser Ala Trp Ser His
        515                 520                 525

Pro Gln Phe Glu Lys
    530

<210> SEQ ID NO 6
<211> LENGTH: 220
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Met Ser Pro Ile Leu Gly Tyr Trp Lys Ile Lys Gly Leu Val Gln Pro
1               5                   10                  15

Thr Arg Leu Leu Leu Glu Tyr Leu Glu Glu Lys Tyr Glu Glu His Leu
            20                  25                  30

Tyr Glu Arg Asp Glu Gly Asp Lys Trp Arg Asn Lys Lys Phe Glu Leu
        35                  40                  45

Gly Leu Glu Phe Pro Asn Leu Pro Tyr Tyr Ile Asp Gly Asp Val Lys
    50                  55                  60

Leu Thr Gln Ser Met Ala Ile Ile Arg Tyr Ile Ala Asp Lys His Asn
65                  70                  75                  80

Met Leu Gly Gly Cys Pro Lys Glu Arg Ala Glu Ile Ser Met Leu Glu
                85                  90                  95

Gly Ala Val Leu Asp Ile Arg Tyr Gly Val Ser Arg Ile Ala Tyr Ser
            100                 105                 110

Lys Asp Phe Glu Thr Leu Lys Val Asp Phe Leu Ser Lys Leu Pro Glu
        115                 120                 125

Met Leu Lys Met Phe Glu Asp Arg Leu Cys His Lys Thr Tyr Leu Asn
    130                 135                 140

Gly Asp His Val Thr His Pro Asp Phe Met Leu Tyr Asp Ala Leu Asp
145                 150                 155                 160
```

```
Val Val Leu Tyr Met Asp Pro Met Cys Leu Asp Ala Phe Pro Lys Leu
            165                 170                 175

Val Cys Phe Lys Lys Arg Ile Glu Ala Ile Pro Gln Ile Asp Lys Tyr
        180                 185                 190

Leu Lys Ser Ser Lys Tyr Ile Ala Trp Pro Leu Gln Gly Trp Gln Ala
            195                 200                 205

Thr Phe Gly Gly Gly Asp His Pro Pro Lys Ser Asp
        210                 215                 220

<210> SEQ ID NO 7
<211> LENGTH: 46
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Gly Ser His His His His His His Gly Ser Gly Gly Ser Gly Gly
1               5                   10                  15

Ser Ala Trp Ser His Pro Gln Phe Glu Lys Gly Gly Gly Ser Gly Gly
            20                  25                  30

Gly Ser Gly Gly Ser Ala Trp Ser His Pro Gln Phe Glu Lys
        35                  40                  45

<210> SEQ ID NO 8
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 8

His His His His His His
1               5

<210> SEQ ID NO 9
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Ala Trp Ser His Pro Gln Phe Glu Lys
1               5

<210> SEQ ID NO 10
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Gly Ser Gly Gly Gly Ser Gly Gly Ser
1               5

<210> SEQ ID NO 11
<211> LENGTH: 11
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 11

Gly Gly Gly Ser Gly Gly Gly Ser Gly Gly Ser
1               5                   10

<210> SEQ ID NO 12
<211> LENGTH: 2
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Gly Ser
1

<210> SEQ ID NO 13
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Gly Gly Ser Gly Ser Ala
1               5

<210> SEQ ID NO 14
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Gly Gly Ser Gly Ser Ala Ala
1               5

<210> SEQ ID NO 15
<211> LENGTH: 95
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
ggaagatggt cgtctccggt gaggcggctg gactctaaat ccagttgggg ccgccagcgg      60
tcccggtcag gttcgactcc ttgcatcttc cgcca                                 95

<210> SEQ ID NO 16
<211> LENGTH: 95
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
ggaagatcgt cgtctccggt gaggcggctg gactctaaat ccagttgggg ccgccagcgg      60
```

-continued

```
tcccggtcag gttcgactcc ttggatcttc cgcca                            95
```

<210> SEQ ID NO 17
<211> LENGTH: 94
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17

```
ggaagatcgt cgtctccggt gaggcggctg gactctaaat ccagttgggg ccgccagcgg   60
tcccggtaag gttcgactcc tatatcttcc gcca                              94
```

<210> SEQ ID NO 18
<211> LENGTH: 95
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18

```
ggaagatggt cgtctccggt gaggcggctg gactctaaat ccagttgggg ccgccagcgg   60
tcccggtcag gttcgactcc ttgcatcttc cgcca                             95
```

<210> SEQ ID NO 19
<211> LENGTH: 95
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19

```
ggaagatggt cgtctccggt gaggcggctg gactctaaat ccagttgggg ccgccagcgg   60
tcccggcgag gttcgactcc tcgtatcttc cgcca                             95
```

<210> SEQ ID NO 20
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20

```
ggaagatgtg gccgagcggt tgaaggcacc ggtctctaaa accggcgacc cgaaagggtt   60
ccagagttcg aatctctgca tcttccgcca                                   90
```

<210> SEQ ID NO 21
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21

```
taggaggcag atc                                                    13
```

<210> SEQ ID NO 22
<211> LENGTH: 73
<212> TYPE: DNA

```
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (39)..(40)
<223> OTHER INFORMATION: a, c, t, g, unknown or other
<220> FEATURE:
<221> NAME/KEY: modified_base
<222> LOCATION: (54)..(56)
<223> OTHER INFORMATION: a, c, t, g, unknown or other

<400> SEQUENCE: 22
tggactggtc tcccagttgg ggccgccagc ggtcccggnn aggttcgact cctnnnatct        60
tccgccaaaa tgc                                                          73

<210> SEQ ID NO 23
<211> LENGTH: 66
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (51)..(51)
<223> OTHER INFORMATION: a, c, t, g, unknown or other

<400> SEQUENCE: 23
gctggcggtc tcaactggat ttagagtcca gccgcctcac cggagacgac natcttccgc        60
gcctcg                                                                  66

<210> SEQ ID NO 24
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(20)
<223> OTHER INFORMATION: This sequence may encompass 1-10 'Gly Ser'
      repeating units

<400> SEQUENCE: 24

Gly Ser Gly Ser Gly Ser Gly Ser Gly Ser Gly Ser Gly Ser Gly Ser
1               5                   10                  15

Gly Ser Gly Ser
            20

<210> SEQ ID NO 25
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (1)..(30)
<223> OTHER INFORMATION: This sequence may encompass 1-10 'Gly Gly Ser'
      repeating units

<400> SEQUENCE: 25

Gly Gly Ser Gly Gly Ser Gly Gly Ser Gly Gly Ser Gly Gly Ser Gly
1               5                   10                  15
```

-continued

```
Gly Ser Gly Gly Ser Gly Gly Ser Gly Gly Ser Gly Gly Ser
            20                  25                  30

<210> SEQ ID NO 26
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (1)..(40)
<223> OTHER INFORMATION: This sequence may encompass 1-10 'Gly Gly Gly
      Ser' repeating units

<400> SEQUENCE: 26

Gly Gly Gly Ser Gly Gly Gly Ser Gly Gly Gly Ser Gly Gly Gly Ser
1               5                   10                  15

Gly Gly Gly Ser Gly Gly Gly Ser Gly Gly Gly Ser Gly Gly Gly Ser
            20                  25                  30

Gly Gly Gly Ser Gly Gly Gly Ser
            35                  40

<210> SEQ ID NO 27
<211> LENGTH: 95
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 27
ggaagatcgt cgtctccggt gaggcggctg gactctaaat ccagttgggg ccgccagcgg     60
tcccgggcag gttcgactcc tgtgatcttc cgcca                               95
```